United States Patent
Kotton et al.

(10) Patent No.: US 10,975,357 B2
(45) Date of Patent: Apr. 13, 2021

(54) METHODS AND COMPOSITIONS RELATED TO DIFFERENTIATED LUNG CELLS

(71) Applicant: TRUSTEES OF BOSTON UNIVERSITY, Boston, MA (US)

(72) Inventors: Darrell N. Kotton, Newton, MA (US); Anjali Jacob, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 16/011,809

(22) Filed: Jun. 19, 2018

(65) Prior Publication Data
US 2018/0371421 A1   Dec. 27, 2018

Related U.S. Application Data

(60) Provisional application No. 62/525,400, filed on Jun. 27, 2017.

(51) Int. Cl.
C12N 5/071   (2010.01)
A61K 35/42   (2015.01)
A61P 11/00   (2006.01)

(52) U.S. Cl.
CPC ............ *C12N 5/0688* (2013.01); *A61K 35/42* (2013.01); *A61P 11/00* (2018.01); *C12N 5/0689* (2013.01); *C12N 2501/01* (2013.01); *C12N 2501/113* (2013.01); *C12N 2501/115* (2013.01); *C12N 2501/117* (2013.01); *C12N 2501/119* (2013.01); *C12N 2501/39* (2013.01); *C12N 2501/415* (2013.01); *C12N 2501/998* (2013.01); *C12N 2501/999* (2013.01); *C12N 2506/03* (2013.01); *C12N 2506/27* (2013.01)

(58) Field of Classification Search
CPC ........................... C12N 5/0688; C12N 5/0689; C12N 2506/27; C12N 2506/03
See application file for complete search history.

(56) References Cited

U.S. PATENT DOCUMENTS

| | | |
|---|---|---|
| 2004/0223952 A1 | 11/2004 | Have-Opbroek et al. |
| 2015/0247124 A1 | 9/2015 | Snoeck et al. |
| 2015/0290249 A1 | 10/2015 | Xu |
| 2016/0068816 A1 | 3/2016 | Osafune et al. |
| 2016/0237401 A1 | 8/2016 | Vallier et al. |
| 2016/0312190 A1 | 10/2016 | Ghaedi et al. |
| 2016/0312191 A1 | 10/2016 | Spence et al. |

FOREIGN PATENT DOCUMENTS

| | | |
|---|---|---|
| WO | 2016/143803 A1 | 9/2016 |
| WO | 2016/203477 A1 | 12/2016 |

OTHER PUBLICATIONS

Barkauskas et al. The Journal of Clinical Investigation 123(7)3025-3036, 2013 (Year: 2013).*
Longmire et al., "Efficient derivation of purified lung and thyroid progenitors from embryonic stem cells." Cell Stem Sell 10(4):398-411 (2012).
McCauley et al., "Efficient derivation of functional human airway epithelium from pluripotent stem cells via temporal regulation of Wnt signaling." Cell Stem Cell 20(6):844-857 (2017).
Ballard et al. "Regulated gene expression in cultured type II cells of adult human lung." American Journal of Physiology—Lung Cellular and Molecular Physiology 299(1):L36-L50 (2010).
Dye et al. "In vitro generation of human pluripotent stem cell derived lung organoids." eLife 4:1999 (2015).
Frank et al. "Emergence of a Wave of Wnt Signaling that Regulates Lung Alveologenesis by Controlling Epithelial Self-Renewal and Differentiation." CellReports 17(9):2312-2325 (2016).
Gonzales et al. "Differentiation of human pulmonary type II cells in vitro by glucocorticoid plus cAMP." American Journal of Physiology—Lung Cellular and Molecular Physiology 283(5):L940-L951 (2002).
Gotoh et al., "Generation of alveolar epithelial spheroids via isolated progenitor cells from human pluripotent stem cells." Stem Cell Reports 3(3):394-403 (2014).
Huang et al. "Efficient generation of lung and airway epithelial cells from human pluripotent stem cells." Nature Biotechnology 32(1):84-91 (2014).
Liu et al., "Differential gene expression in the distal tip endoderm of the embryonic mouse lung." Gene Expression Patterns 2(3):229-233 (2002).
Mucenski et al. "β-Catenin regulates differentiation of respiratory epithelial cells in vivo." American Journal of Physiology—Lung Cellular and Molecular Physiology 289(6):L971-L979 (2005).
Shu et al. "Wnt/beta-catenin signaling acts upstream of N-myc, BMP4, and FGF signaling to regulate proximal-distal patterning in the lung." Developmental Biology 283(1):226-239 (2005).
Han et al. "The role of surfactant in lung disease and host defense against pulmonary infections." Annals of the American Thoracic Society 12(5): 765-774 (2015).

* cited by examiner

*Primary Examiner* — Marcia S Noble
(74) *Attorney, Agent, or Firm* — Nixon Peabody LLP; Ronald I. Eisenstein; Nicole D. Kling

(57) ABSTRACT

Described herein are methods and compositions related to induced alveolar epithelial type 2 cells (iAEC2s), e.g., artificially-produced epithelial type 2 cells.

25 Claims, 63 Drawing Sheets

Specification includes a Sequence Listing.

C17 NGST, 46XY 20/20

RUES2 ST, 46XX 20/20

BU3 NGST, 46XY 20/20

| Up in Adult AEC2 v. Tomato + |
|---|
| HALLMARK_INTERFERON_GAMMA_RESPONSE |
| HALLMARK_INTERFERON_ALPHA_RESPONSE |
| HALLMARK_TNFA_SIGNALING_VIA_NFKB |
| HALLMARK_INFLAMMATORY_RESPONSE |
| HALLMARK_IL6_JAK_STAT3_SIGNALING |
| HALLMARK_ALLOGRAFT_REJECTION |
| HALLMARK_COMPLEMENT |
| HALLMARK_IL2_STAT5_SIGNALING |
| HALLMARK_KRAS_SIGNALING_UP |
| HALLMARK_APOPTOSIS |
| HALLMARK_REACTIVE_OXIGEN_SPECIES_PATHWAY |
| HALLMARK_ADIPOGENESIS |
| HALLMARK_HYPOXIA |
| HALLMARK_XENOBIOTIC_METABOLISM |
| HALLMARK_COAGULATION |
| HALLMARK_P53_PATHWAY |
| HALLMARK_HEME_METABOLISM |
| HALLMARK_FATTY_ACID_METABOLISM |

*FIG. 12A*

Up in Tomato+ v. Day 15 CD47+

| Gene Set | adj.P | Gene Number |
|---|---|---|
| HALLMARK_OXIDATIVE_PHOSPHORYLATION | 7.89E-13 | |
| HALLMARK_ADIPOGENESIS | 6.87E-06 | |
| HALLMARK_CHOLESTEROL_HOMEOSTASIS | 6.98E-06 | |
| HALLMARK_FATTY_ACID_METABOLISM | 9.28E-06 | |
| HALLMARK_INTERFERON_GAMMA_RESPONSE | 4.06E-04 | |
| HALLMARK_INTERFERON_ALPHA_RESPONSE | 4.52E-04 | |
| HALLMARK_PROTEIN_SECRETION | 1.26E-03 | |
| HALLMARK_TNFA_SIGNALING_VIA_NFKB | 4.78E-03 | 84/190 |
| HALLMARK_HEME_METABOLISM | 1.26E-02 | |
| HALLMARK_IL6_JAK_STAT3_SIGNALING | 1.26E-02 | 32/67 |
| HALLMARK_PEROXISOME | 1.51E-02 | |
| HALLMARK_XENOBIOTIC_METABOLISM | 3.42E-02 | |
| HALLMARK_BILE_ACID_METABOLISM | 3.64E-02 | |

FIG. 12C

Up in Tomato- v. Tomato+

| Gene Set | adj. P | Gene Number |
|---|---|---|
| HALLMARK_EPITHELIAL_MESENCHYMAL_TRANSITION | 4.24E-09 | 23/292 |
| HALLMARK_ANGIOGENESIS | 2.33E-05 | 4/32 |
| HALLMARK_PANCREAS_BETA_CELLS | 2.23E-04 | 6/25 |
| HALLMARK_WNT_BETA_CATENIN_SIGNALING | 5.23E-04 | 4/39 |
| HALLMARK_P53_PATHWAY | 8.06E-04 | 9/193 |
| HALLMARK_HEDGEHOG_SIGNALING | 9.01E-04 | 5/32 |
| HALLMARK_APICAL_JUNCTION | 1.61E-03 | 16/177 |
| HALLMARK_HYPOXIA | 3.39E-03 | 7/186 |
| HALLMARK_KRAS_SIGNALING_UP | 7.08E-03 | 14/170 |
| HALLMARK_MYOGENESIS | 8.92E-03 | 10/162 |
| HALLMARK_TNFA_SIGNALING_VIA_NFKB | 1.07E-02 | 7/190 |
| HALLMARK_ESTROGEN_RESPONSE_EARLY | 4.18E-02 | 9/191 |
| HALLMARK_UV_RESPONSE_DN | 4.32E-02 | 15/144 |

FIG. 12E

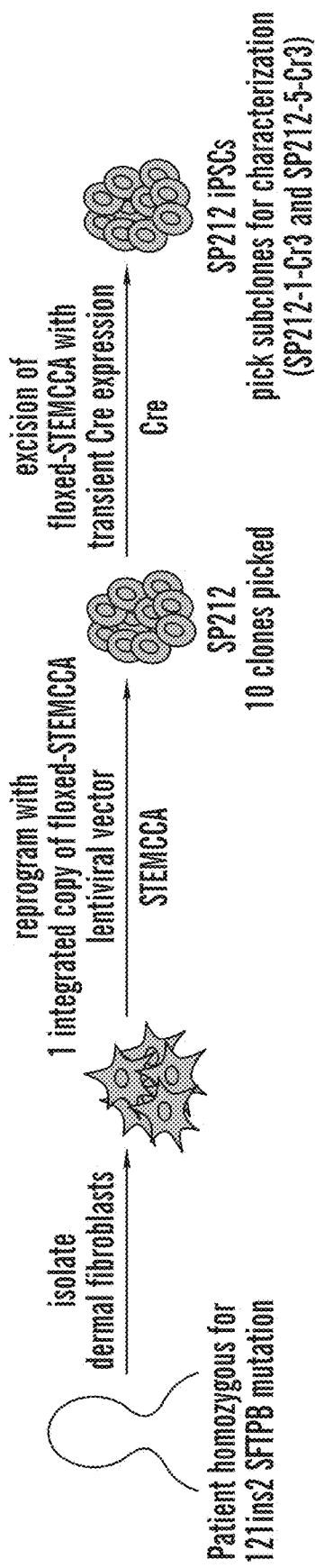

| Patient Characteristics | |
|---|---|
| Respiratory symptoms | respiratory distress and cyanosis within minutes of birth progressive respiratory failure at day of life 4 |
| Age at Diagnosis | 1 month |
| Biopsy | intersitital pneumonitis AEC2 hyperplasia |
| Genetic mutation | c.397delinsGAA (p.P133Efs*95), hg19 "SFTPB 121ins2" |
| Explant histology | Smooth muscle hypertrophy<br>AEC2 hyperplasia<br>Abnormal small air space development<br>Alveolar proteinosis<br>Vascular changes consistent with pulmonary hypertension |
| Treatment | bilateral lung transplantation |

FIG. 14A

Amp/Deletion Table

| Chr | Amp/Del | Start (bp) | Stop (bp) | Size (kb) | Chr Band | # Probes | Log2 Ratio | Genes[α] | Overlap Normal CNVs?[β] |
|---|---|---|---|---|---|---|---|---|---|
| 1 | Amp | 47,397,397 | 48,648,121 | 1,251 | p33 | 25 | 0.58751 | CYP4A11, CYP4X1, CYP4Z1, CYP4A22, LINC00853, PDZK1IP1, TAL1, STIL, CMPK1, LINC01389, FOXE3, FOXD2-AS1, FOXD2, TRABD2B, SKINT1L | No |
| 2 | Del | 242,886,386 | 243,007,359 | 121 | q37.3 | 5 | -0.94132 | LINC01237, LOC102723927 | Yes |

Total Amp/Del: 2

[α] Genes amplified or deleted are cross referenced against the Online Mendelian Inheritance in Man® (OMIM®) database. Genes well documented with disorders and morbidity are shown within an ellipse. Genes with some association with disease are shown within a rectangle. Genes shown within no shape have no known association with disease.

[β] Amplifications and deletions are cross referenced against the Database of Genomic Variants (DGV), which contains genomic variations observed in healthy individuals.

FIG. 20

Amp/Deletion Table

| Chr | Amp/Del | Start (bp) | Stop (bp) | Size (kb) | Chr Band | # Probes | Log2 Ratio | Genes[α] | Overlap Normal CNVs?[β] |
|---|---|---|---|---|---|---|---|---|---|
| 1 | Amp | 47,397,397 | 48,648,121 | 1,251 | p33 | 25 | 0.600945 | CYP4A11, CYP4X1, CYP4Z1, CYP4A22, LINC000853, PDZK1IP1, (TAL1), STIL, CMPK1, LINC01389, FOXE3, FOXD2-AS1, FOXD2, TRABD2B, SKINT1L | No |
| 2 | Del | 242,886,386 | 243,007,359 | 121 | q37.3 | 5 | -1.07809 | LINC01237, LOC102723927 | Yes |
| 6 | Del | 32,523,337 | 32,604,038 | 81 | p21.32 | 3 | -0.82506 | HLA-DRB6, HLA-DRB1 | Yes |
| 14 | Del | 20,253,739 | 20,517,545 | 264 | q11.2 | 5 | -0.58936 | OR4K14, OR4K13 | Yes |

Total Amp/Del: 4

[α] Genes amplified or deleted are cross referenced against the Online Mendelian Inheritance in Man® (OMIM®) database. Genes well documented with disorders and morbidity are shown within an ellipse. Genes with some association with disease are shown within a rectangle. Genes shown within no shape have no known association with disease.

[β] Amplifications and deletions are cross referenced against the Database of Genomic Variants (DGV), which contains genomic variations observed in healthy individuals.

METHODS AND COMPOSITIONS RELATED TO DIFFERENTIATED LUNG CELLS

CROSS-REFERENCE TO RELATED APPLICATIONS

This application claims benefit under 35 U.S.C. § 119(e) of U.S. Provisional Application No. 62/525,400 filed Jun. 27, 2017, the contents of which are incorporated herein by reference in their entirety.

GOVERNMENT SUPPORT

This invention was made with government support under Contract No. HL095993 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 19, 2018, is named 701586-089650-USPT_SL.txt and is 4,357 bytes in size.

TECHNICAL FIELD

The technology described herein relates to methods of differentiating lung cells and uses thereof.

BACKGROUND

Disease modeling and drug development are greatly assisted by the availability of relevant cell types ex vivo. In vitro-differentiated cells are a particularly powerful tool in such cases, but effective methods for conducting such differentiation remain unknown for many cell types.

One example is lung cells, particularly type II alveolar epithelial cells, which are involved in a number of lung diseases and comprise an important part of alveaolae in intact lungs. Attempts to differentiate progenitors into type II alveolar epithelial cells have been plagued by high rates of transdifferentiation and/or the need for mixed cultures.

SUMMARY

Described herein is the successful development of methods that provide large, highly pure, stable populations of induced type II alveolar epithelial cells. In some aspects of any of the embodiments, described herein is a method of making induced alveolar epithelial type 2 cells (iAEC2s), the method comprising: contacting a NKX2-1+ lung epithelial progenitor cell with: an agonist of Wnt/beta-catenin signaling; a corticosteroid; and an agonist of cyclicAMP or the cyclicAMP pathway.

In some embodiments of any of the aspects, the contacting step is continued for at least 3 days. In some embodiments of any of the aspects, the contacting step is continued for at least 15 days.

In some embodiments of any of the aspects, the method further comprises a culturing step after the contacting step, wherein the cells are cultured without being contacted with an agonist of Wnt/beta-catenin signaling. In some embodiments of any of the aspects, the culturing step is continued for at least 5 days. In some embodiments of any of the aspects, the culturing step is continued for at least 10 days.

In one aspect of any of the embodiments, described herein is a method of making iAEC2s, the method comprising: a first culturing step of culturing a population of NKX2-1+ lung epithelial progenitor cells in the presence of: an agonist of Wnt/beta-catenin signaling; a corticosteroid; and an agonist of cyclicAMP or the cyclicAMP pathway; for a period of about 2 weeks; a second culturing step of culturing the cells resulting from the first culturing step in the presence of a corticosteroid and an agonist of cyclicAMP or the cyclic AMP pathways but not an agonist of Wnt/beta-catenin signaling; for a period of about 1 week; and a third culturing step of culturing the cells resulting from the second culturing step in the presence of: an agonist of Wnt/beta-catenin signaling; a corticosteroid; and an agonist of cyclicAMP or the cyclicAMP pathway for a period of about 1 week.

In some embodiments of any of the aspects, the agonist of Wnt/beta catenin signaling is selected from the group consisting of: CHIR99021; a recombinant Wnt polypeptide; a Wnt polypeptide; an exogenous Wnt polypeptide; BIO; WAY-316606; a (hetero) arylpyrimidine; IQ1; QS11; SB-216763; DCA; R-spondin; and an inhibitor of Axin2 and/or APC. In some embodiments of any of the aspects, the corticosteroid is selected from the group consisting of: dexamethasone; hydrocortisone; cortisone; prednisone; prednisolone; methylprednisolone; triamncinolone; betamethasone; fludrocortisone acetate; and deoxycorticosterone acetate. In some embodiments of any of the aspects, the agonist of cyclicAMP or the cyclicAMP pathway is selected from the group consisting of: cyclicAMP; IBMX, cholera toxin, forskolin, caffeine, theophylline, bucaldesine, and pertussis toxin.

In some embodiments of any of the aspects, the NKX2-1+ lung epithelial progenitor cell is further contacted or cultured with an agonist of FGF signaling. In some embodiments of any of the aspects, the agonist of FGF signaling is a polypeptide selected from the group consisting of: KGF; a FGF receptor ligand; FGF1; FGF2; FGF3; FGF4; FGF6; FGF8; FGF9; FGF10; FGF17; FGF18; FGF22; and a small molecule agonist of FGF signaling. In some embodiments of any of the aspects, the agonist of FGF signaling is KGF polypeptide.

In some embodiments of any of the aspects, the culturing or contacting step comprising a corticosteroid and an agonist of cyclicAMP or the cyclicAMP pathway further comprises culturing or contacting with 3-isobutyl-1-methylxanthine (IMBX).

In some embodiments of any of the aspects, the NKX2-1+ lung epithelial progenitor cell is not contacted or cultured with a mesenchymal cell.

In some embodiments of any of the aspects, the NKX2-1+ lung epithelial progenitor cell is a CD47hi/CD26lo cell. In some embodiments of any of the aspects, the NKX2-1+ lung epithelial progenitor cell is provided by sorting lung epithelial progenitor cells to isolate a CD47hi/CD26lo population. In some embodiments of any of the aspects, the NKX2-1+ lung epithelial progenitor cell is derived from an induced pluripotent stem cell (iPSC). In some embodiments of any of the aspects, the NKX2-1+ lung epithelial progenitor cell is derived from a cell obtained from a subject. In some embodiments of any of the aspects, the method further comprises first genetically modifying the NKX2-1+ lung epithelial progenitor cell or the less differentiated cell the NKX2-1+ lung epithelial progenitor cell is derived from. In some embodiments of any of the aspects, the NKX2-1+ lung epithelial progenitor cell is derived from an less differentiated cell by contacting the less differentiated cell with CHIR, BMP4, and RA. In some embodiments of any of the aspects, the iAEC2 cell is a NKX2-1+/SFTPC+ cell.

In one aspect of any of the embodiments, described herein is an iAEC2 cell produced according to the methods described herein.

In one aspect of any of the embodiments, described herein is a method of treating a lung disease in a subject in need thereof, the method comprising administering to the subject an iAEC2 cell (e.g., produced according to a method as described herein). In one aspect of any of the embodiments, described herein is an iAEC2 cell (e.g., produced according to a method described herein), for administration to the subject in need of treatment for a lung disease. In some embodiments of any of the aspects, the lung disease is selected from the group consisting of: a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and emphsyema. In some embodiments of any of the aspects, the iAEC2 cell is derived from a cell obtained from the subject. In some embodiments of any of the aspects, the NKX2-1+ lung epithelial progenitor cell or the less differentiated cell the NKX2-1+ lung epithelial progenitor cell is derived from was genetically modified to correct a mutation that contributed to the lung disease.

In one aspect of any of the embodiments, described herein is a method of identifying a treatment as effective in treating lung disease, the method comprising: contacting an iAEC2 (e.g., produced according to a method described herein) with a candidate treatment agent; identifying the candidate treatment agent as effective if one or more of the following phenotypes is observed in the iAEC2 contacted with the candidate treatment agent as compared to an iAEC2 not contacted with the candidate treatment agent:
  i) increased cell survival;
  ii) increased cell survival in the presence of cellular stressors;
  iii) decreased release of toxic agents;
  iv) improved cellular pathology arising from a genetic mutation in the iAEC2;
  v) increased iAEC2 differentiation;
  vi) decreased iAEC2 proliferation in the presence of carcinogens; and/or
  vii) increased secretion of cytoprotective agents.

In some embodiments of any of the aspects, the iAEC2 is derived from a cell obtained from an individual subject and the treatment is identified as an effective treatment for that individual subject.

BRIEF DESCRIPTION OF THE DRAWINGS

FIG. 1A depicts schematics showing TALENs targeting strategy and edited NKX2-1GFP and SFTPCtdTomato loci post Cre-mediated antibiotic cassette excision. FIG. 1B depicts a schematic showing differentiation protocol from PSC to putative iAEC2s used in subsequent panels. FIG. 1C depict representative flow cytometry of SFTPCtdTomato expression in Day 30 RUES2. RT-qPCR of pre-sort, sorted tdTomato+(Tom+), and tdTomato−(Tom−) samples compared to primary Week 21 (Wk 21) human fetal distal lung control (85-90% SFTPC+). Bars represent mean fold change in expression (2-ΔΔCt) compared to undifferentiated (day 0) PSCs±S.D. in n=3 biological replicates from 3 differentiations separated at the day 0 stage. FIG. 1D depicts Day 21 representative flow cytometry analysis of C17 Day 15 unsorted, sorted NKX2-1GFP+, or sorted NKX2-1GFP− outgrowth. Bars represent mean±S.D., n=3 biological replicates from differentiations separated at the day 0 stage, ***p≤0.001 by unpaired, two-tailed Student's t-test.

FIG. 2A depicts representative flow cytometry analysis on day 21 of C17 iPSCs sorted based on NKX2-1GFP+ expression on Day 15 and replated for outgrowth from day 15-21 with or without addition of CHIR to K+DCI base media. Bars represent mean±S.D., n=6 biological replicates separated from the day 0 stage, ****p≤0.0001 by unpaired, two-tailed Student's t-test. FIG. 2B depicts Day 30 representative flow cytometry analysis of BU3 iPSCs sorted on Day 15 based on NKX2-1GFP+ expression, replated for outgrowth from days 15-30 and then sorted for analysis from each gate: NKX2-1GFP−SFTPCtdTomato−(NG−ST−), NKX2-1GFP+SFTPCtdTomato−(NG+ST−), and NKX2-1GFP+SFTPCtdTomato+ (NG+ST+). RT-qPCR of these populations, in addition to unsorted (Pre-Sort) Day 30 cells and Week 21 primary human fetal distal lung controls (21 Wk) is shown with bars representing mean fold change (2-ΔΔCt compared to day 0 iPSCs)±S.D., n=3 biological replicates differentiated separately from the day 15 stage. FIG. 2C depicts a schematic describing experiment in which Day 22 alveolospheres were dissociated for cell sorting and SFTPCtdTomato+ cells were sorted either into 3D culture in CK+DCI media or 2D culture (tissue culture-treated plastic) in 10% FBS media. Representative phase/brightfield and tdTomato fluorescence microscopy of live cells after 7 days in either culture condition, scale bars represent 50 μm, arrow indicates tdTomato expression in 2D cultured cells. RT-qPCR of 3D vs 2D cultured cells with bars representing mean fold change (2-ΔΔCt compared to day 0 PSCs)±S.D., n=3 biological replicates from differentiations separate from the day 0 stage, *p≤0.05, ***p≤0.001 by unpaired, two-tailed Student's t-test. FIG. 2D depicts representative confocal immunofluorescence microscopy of Edu and anti-tdTomato after 24 hour EdU incubation. Nuclei were stained with Hoechst. Representative flow cytometry analysis of Day 38 BU3 iPSC-derived alveolospheres shows co-expression of EPCAM and tdTomato proteins FIG. 2E depicts a graph showing cell number at consecutive passages of 1×104 BU3 SFTPCtdTomato+ sorted cells plated on Day 22 in 3D CK+DCI culture. Passages were 10 and 14 days apart, respectively. Representative flow cytometry and live cell imaging of Day 66 RUES2-derived alveolospheres from the outgrowth of SFTPCtdTomato+ cells sorted on Day 22 and passaged 3 times. Scale bars represent 100 μm.

FIG. 3A depicts a schematic describing temporal expression of NKX2-1 and SFTPC during human fetal lung development. FIG. 3B depicts a representative image of live Day 30 RUES2-derived alveolospheres (scale bar, 100 μm) and fixed plastic-section stained with toluidine blue. Arrows indicate cells with putative lamellar-body-like inclusions, gl=putative glycogen lake. FIG. 3C depicts transmission electron microscopy of Day 30 RUES2-derived alveolospheres. Lbl=lamellar body-like inclusion, desm=desmosome, gl=glycogen lake. Scale bars represent 800 nm, 1 μm and 2 μm, as indicated. FIG. 3D depicts immunogold labeling of mature SFTPB and SFTPC in Day 30 RUES2 alveolospheres. Scale bars represent 0.2 μm. Significance of relative labeling index was calculated by comparing observed counts in each cellular compartment with expected counts by $\chi^2$ statistics and contingency table analyses. *p-value<0.05, RLI>1, and compartment $\chi^2$ value>25% of the total $\chi^2$ value for this study.

FIG. 4A depicts a schematic showing cellular compartments in which proSFTPB processing into mature SFTPB occurs. FIG. 4B depicts a western blot of a timecourse of alveolosphere differentiation (Day 0, 16, 22, 29, and 36) and 6 day DCI-cultured primary week 21 human fetal distal lung (HFL DCI-D6) as a positive control. Top panel uses anti-N Flank antibody that binds to the N-pro region of pro-SFTPB (present in the 42, 25, and 10 kD intermediates), and bottom panel uses anti-mature SFTPB antibody (PT3) that binds all SFTPB forms, including the 8kD mature form. FIG. 4C depicts a schematic showing dissociation protocol for isolation of intracellular and extracellular components of alveolospheres. Both absolute (nmol lipid/µg DNA in cell samples) and relative (nmol lipid/nmol total diacyl phospatidylcholine) are shown for both surfactant-specific 32:0 DPPC and nonspecific 34:1 PC. Surfactant index was calculated as the sum of the surfactant-specific 30 and 32 PCs divided by the sum of non-surfactant specific 36 PCs. Bars represent mean±S.D. for each analysis, n=3 biological replicates from wells separate from the Day 15 sort stage, *p≤0.05, p≤0.01, *p≤0.001, ****p≤0.0001 by unpaired, two-tailed Student's t-test.

FIG. 5A depicts a schematic of timepoints in alveolosphere differentiation from which samples were taken for RNA-Sequencing. FIG. 5B depicts principal component analysis (PCA) of gene expression variance across all samples based on 30,000 transcripts. FIG. 5C depicts log 2 expression of SFTPC across all samples, with the dotted line representing "noise," since these levels of expression are not consistently detected by RT-qPCR. Lower right panel shows RT-qPCR of each sample, with mean fold change (2-ΔΔCt compared to day 0 PSCs)±S.D., n=3 biological replicates from separate differentiations (RUES2 samples), cells isolated for RNA separately (Wk 21), cells cultured for 4 days separately (Wk 21 DCI), and cells from separate lungs (Adult AEC2), *p≤0.05, **p≤0.01 by unpaired, two-tailed Student's t-test. FIG. 5D depicts a heatmap of row-normalized expression of selected lineage markers across PSC-derived and primary samples. FIG. 5E depicts a heatmap of top 10 genes upregulated in day 35 Tom+ cells vs day 15 progenitors (ranked by fold change, FDR≤0.05). Known AEC2 genes are in bold. FIG. 5F depicts a heatmap of top 50 genes differentially expressed in day 35 Tom+ cells vs day 15 cells (ranked by FDR, FDR≤0.01). Known AEC2 genes are in bold. FIG. 5G depicts a heatmap of supervised hierarchical clustering based on top 300 genes differentially expressed in day 35 Tom+vs day 15 cells (ranked by absolute fold change, FDR≤0.01). FIG. 5H depicts: Left panel shows experimental design, middle panel shows Western blot for IkB-alpha, phospho-Stat3 (Tyr705), and pan-actin. Bottom panels show RT-qPCR of each sample, with fold change (2-ΔΔCt compared to day 0)±S.D., n=3 biological replicates from differentiations separate from the day 35 passaging stage, *p≤0.05, **p≤0.01 by unpaired, two-tailed Student's t-test.

FIG. 6A depicts a heatmap of top 10 upregulated and top 10 downregulated genes in Day 35 Tom+vs Tom– populations (ranked by fold change, FDR≤0.05). FIG. 6B depicts a heatmap of selected differentially expressed genes downregulated in Tom+vs Tom– populations (FDR≤0.05) from the MSigDB v5.1 Hallmark Wnt/β-Catenin Signaling database. RT-qPCR of Day 15, Day 35 Tom- and Day 35 Tom+ samples, with fold change (2-ΔΔCt compared to day 0)±S.D., n=3 biological replicates. FIG. 6C depicts a schematic showing late CHIR withdrawal experiment. Representative flow cytometry analysis of Day 38 sort gates and Day 50 outgrowth of the BU3 NKX2-1GFP+/SFTPCtdTomato– population cultured with or without CHIR from Day 40-50. Bars show mean±S.D., n=3 biological replicates separate from the Day 38 sort stage. FIG. 6D depicts RT-qPCR of Day 50+/–CHIR populations and week 21 human fetal distal lung, with bars representing fold change (2-ΔΔCt compared to iPSCs)±S.D., n=3 biological replicates from differentiations separate from the Day 38 sort stage, *p≤0.05, p≤0.01, *p≤0.001 by unpaired, two-tailed Student's t-test. FIG. 6E depicts a schematic of CHIR addback experiment, representative images of live RUES2 alveolospheres (brightfield/tdTomato overlay; –CHIR week 4-5 (Day 32-39), +/–CHIR addback week 5-6 (Day 39-48). Bar graphs show percent SFTPCtdTomato+ and total cell number in Day 48 populations+/–CHIR withdrawal and +/–CHIR addback. Bars represent mean+/–SD of n=3 differentiations separate from the Day 32 passaging stage, *p≤0.05, p≤0.01, *p≤0.001 by unpaired, two-tailed Student's t-test. FIG. 6F depicts a schematic of putative effects of Wnt stimulation on lung epithelial differentiation.

FIG. 7A depicts chest radiograph of child from which iPSCs were generated, showing diffuse pulmonary infiltrates. Schematic showing the process of correcting both alleles carrying the homozygous 121ins2 SFTPB mutations in iPSCs derived from dermal fibroblasts, resulting in pre-correction (SP212) and post-correction (SP212Corr) iPSC lines. FIG. 7B depicts SFTPB exon4 genomic sequence, with 121ins2 C→GAA mutation, CRISPR guide RNA target sequence, PAM cutting site, oligo-based donor design with corrected base. Pre- and post– correction DNA sequencing chromatograms with boxes showing 121ins2 mutation site sequence. Figure discloses SEQ ID NOS 16-19, respectively, in order of appearance. FIG. 7C depicts RT-qPCR of Day 35 SP212 and SP212Corr alveolospheres, with bars representing fold change (2-ΔΔCt compared to day 0 iPSCs)±S.D., n=3 biological replicates differentiated separately from the day 0 stage, **p≤0.01 by unpaired, two-tailed Student's t-test. FIG. 7D depicts: Top panel shows a western blot for mature SFTPB (immunoblotted with PT3 antibody) on SP212 and SP212Corr alveolospheres (n=3), as well as RUES2 alveolospheres cultured separately from Day 15, 6 Day DCI cultured week 21 human fetal distal lung (HFL DCI-D6), and lung samples from a different patient with the same SFTPB121ins2 mutation. Bands showing mature 8kD SFTPB are present only in normal week 21 controls, RUES2 alveolospheres, and SP212Corr alveolospheres (closed arrowhead). Bottom panel shows western blots for mature SFTPB (PT3) and proSFTPC (NPRO-SFTPC) in 2 different alveolosphere samples of SP212, and 1 sample of SP212Corr, all differentiated separately from the day 0 stage, with ~6-10kD abnormal/misprocessed proSFTPC band (closed arrowhead) present only in the SP212 samples, and 8kD mature SFTPB (open arrowhead) present only in the cultured week 21 and SP212Corr samples. FIG. 7E depicts representative immunofluorescence microscopy of proSFTPB, NKX2-1 in SP212 and SP212Corr alveolospheres. Nuclei were stained with Hoechst dye; scale bars represent 50 μm. FIG. 7F depicts representative TEM images of SP212 and SP212Corr alveolospheres; scale bars represent 500 nm.

FIG. 8A demonstrates that C17 NKX2-1GFP; SFTPCtdTomato (NGST), RUES2 SFTPCtdTomato (ST), and BU3 NKX2-1GFP; SFTPCtdTomato (NGST) iPSC lines show normal karyotype in 20 out of 20 cells by G-banding analysis. FIG. 8B depicts a schematic of primer binding locations, gel showing PCR validation of tdTomato targeting (P3,P4; 906 bp); intact endogenous SFTPC in the non-targeted locus (P1,P2; 997 bp); and excision of the puromycin resistance cassette (P5,P6; 600 bp). Note: primers P1 and P3 bind in the endogenous genome outside of any targeting plasmids. First 4 lanes on each gel (1-4) are clones selected for screening, + indicates positive control for each expected PCR product, − indicates negative control, and W represents "water only" control. FIG. 8C depicts a schematic of published differentiation protocol with representative GFP/tdTomato/phase overlay images of C17 reporter line at anterior foregut endoderm stage, Day 15, Day 31, and Day 35 of differentiation. Arrows indicate emergence of a loop of epithelium co-expressing NKX2-1GFP and SFTPCtdTomato. Scale bar represents 1 mm. Table shows growth factor abbreviations and concentrations. FIG. 8D depicts representative flow cytometry from C17 Day 35 differentiation. RT-qPCR of presort and sorted (NG−ST−, NG+ST−, or NG+ST+) populations; bars represent fold change (2-ΔΔCt compared to day 0 iPSCs)±S.D., n=3 biological replicates from differentiations separate from the day 0 PSC stage.

FIG. 9A depicts a schematic of differentiation scheme and yield of SFTPC+ cells resulting from unsorted progenitors. Bars represent mean percent SFTPCtdTomato+ cells±S.D. in Day 30 RUES2 cultured from Day 15-30 in CFK+DCI media with one component removed in n=3 differentiations separate from the Day 0 stage. FIG. 9B depicts C17 iPSCs differentiated in a similar screening approach to that shown in FIG. 9A, except NKX2-1+ progenitors are sorted on day 15 for outgrowth in various media and analyzed at day 21 by flow cytometry. Bars represent mean percent SFTPCtdTomato+ cells±S.D. In the left graph, media consist of CFK+DCI with one indicated component added (abbreviations listed in the above table). In the middle graph, various components were removed from CFK+DCI media in n=3 differentiations separate from the Day 0 stage (*p≤0.05, p≤0.01 compared to the CFK+DCI condition by unpaired, two-tailed Student's t-test). In the right graph, CK+DCI media was supplemented with various components, in n=2 differentiations. No conditions other than CK+DCI showed a significant increase in Day 21 percent SFTPCtdTomato+ cells when compared to CFK+DCI media. FIG. 9C depicts representative flow cytometry of Day 15 CD47hi/CD26lo and CD47lo populations. Top panel shows intracellular NKX2-1 protein on day 15 in unsorted, CD47hi/CD26lo, and CD47lo sort gates, and bottom panel shows SFTPCtdTomato expression in the Day 21 outgrowth of each population, sorted on day 15 for replating and 3D outgrowth until day 21 analysis. Bars represent mean±S.D. of n=3 differentiations separated at the PSC stage (*p≤0.001, ****p≤0.0001 by unpaired, two-tailed Student's t-test).

FIG. 10A depicts representative flow cytometry of Day 30 BU3 iPSCs, sorted based on GFP expression on day 15 for replating and outgrowth until Day 30 differentiation. RT-qPCR of day 30 "presort" population vs cells sorted from each indicated quadrant (NG−ST−, NG+ST−, or NG+ST+); bars represent mean fold change (2-ΔΔCt compared to day 0 iPSCs)±S.D., n=3 biological replicates from differentiations separate from the Day 15 sort stage (p≤0.01, *p≤0.001 by unpaired, two-tailed Student's t-test). FIG. 10B depicts RT-qPCR of Day 66, passage 3 alveolospheres (unsorted outgrowth from Day 38 sorted SFTPCtdTomato+ cells); bars represent fold change (2-ΔΔCt compared to iPSCs)±S.D., n=3 biological replicates from differentiations separate from the Day 38 sort stage.

FIG. 11A depicts representative TEM images of Day 70 BU3 alveolospheres (outgrowth from cells sorted on day 30 for SFTPCtdTomato expression and passaged 3 times). Scale bar represents 500 nm. FIG. 11B depicts periodic acid-Schiff (PAS) stain of Day 30 RUES2 alveolospheres, with pink staining indicating glycogen positive cytoplasmic regions. FIG. 11C depicts additional TEM images of Day 30 RUES2 alveolospheres.

FIGS. 12A-12E demonstrate global transcriptomic profiling of iAEC2s compared to early timepoints in differentiation and primary AEC controls. FIG. 12A depicts a list of all Hallmark Gene Set Enrichment Analysis (GSEA) pathways upregulated in adult AEC2s vs Tom+ cells (ranked by FDR, FDR≤0.05), with pathways related to immune signaling highlighted and pathways related to oxidant stress highlighted. FIG. 12B: Left panel shows a Venn diagram of genes upregulated in Adult AEC2s vs Day 15 cells and genes upregulated in Tom+ cells vs Day 15 cells (FDR≤0.05), with selected AEC2 genes shown in the overlap region. In each non-overlapping region, the top 10 upregulated genes ranked by fold change are shown. Right panel shows a Venn diagram of genes upregulated in Tom+vs Day 15 cells and genes upregulated in Tom− cells vs Day 15 cells (FDR≤0.05). In each non-overlapping region, the top 10 upregulated genes ranked by fold change are shown. Note: the Tom+ and Tom− cells largely upregulate the same genes from Day 15-35, including many AEC2 genes. FIG. 12C depicts a list of all Hallmark Gene Set Enrichment Analysis (GSEA) pathways upregulated in Tom+ cells vs. day 15 cells (ranked by FDR, FDR≤0.05), with the TNFa signaling via NFkB and IL6/Jak/Stat3 pathways (the top signaling pathways differentially expressed) highlighted. FIG. 12D depicts a heatmap of log 2 expression of selected genes in Day 0, Day 15, Day 35 Tom−, Day 35 Tom+, week 21 AEC, and adult AEC2 populations. FIG. 12E depicts a list of all Hallmark Gene Set Enrichment Analysis (GSEA) pathways upregulated in Tom− cells vs. Tom+ cells (ranked by FDR, FDR≤0.05), with the Wnt/bCatenin signaling pathway (the top developmental signaling pathway differentially expressed) highlighted.

FIG. 13A depicts a schematic of CHIR addback protocol and representative RUES2 Day 48 flow cytometry. FIG. 13B depicts RT-qPCR of alveolar transcripts in Day 48 alveolospheres differentiated using the protocol in FIG. 13A compared to primary fetal alveolar epithelial control cells (week 21 gestation; "Wk 21"); bars represent mean fold change (2-ΔΔCt compared to iPSCs)±S.D., n=3 biological replicates from differentiations separate from the Day 15 sort stage.

FIGS. 14A-14E demonstrate reprogramming of dermal fibroblasts to generate patient-specific iPSCs carrying homozygous 121ins2 SFTPB mutations. FIG. 14A: Left panel shows reprogramming approach to generate iPSCs free of any residual exogenous reprogramming factors. Schematic indicates approach for reprogramming the subject's dermal fibroblasts using the hSTEMCCA-loxP lentiviral vector, encoding the 4 human factors, OCT4, KLF4, SOX2, and cMYC, with methods previously detailed (Somers et al., 2010). Right panel shows table with patient clinical information. FIGS. 14B-14D: Southern blotting of BamH1-digested gDNA from each iPSC clone was used to quantify the number of copies of integrated reprogramming vector per clone, detected as a single integrated STEMMCA copy visualized with a probe against the WPRE lentiviral element. This single floxed-STEMCCA copy was then excised by transient exposure to Cre recombinase with validation by both PCR (FIG. 14B) and Southern blotting (FIG. 14D) of gDNA. Ethidium bromide stained Southern blot indicates similar loading and BamH1 digestion of all clones. Each subclone after transient Cre exposure is indicated. Normal karyotype (FIG. 14C) was confirmed by G-banding analysis, and this analysis was repeated, confirming normal karyotype after correction of the 121ins2 mutation (SP212Corr). FIG. 14E depicts immunostaining characterization of stem cell marker expression was performed for each clone with expected positive staining for SSEA4, TRA1/81, and TRA1/60. SSEA1 staining (expected to be negative in human stem cells) was included as a negative control stain.

FIG. 20 depicts a table of aCGH Microarray results of BU3 NGST Alveolospheres. Cells were sorted SFTPC-tdTomato+ and replated on day 54 of differentiation and passaged 3 times prior to analysis.

FIG. 21 depicts a table of aCGH Microarray results of BU3 NGST iPSCs.

DETAILED DESCRIPTION

Figure 1A:
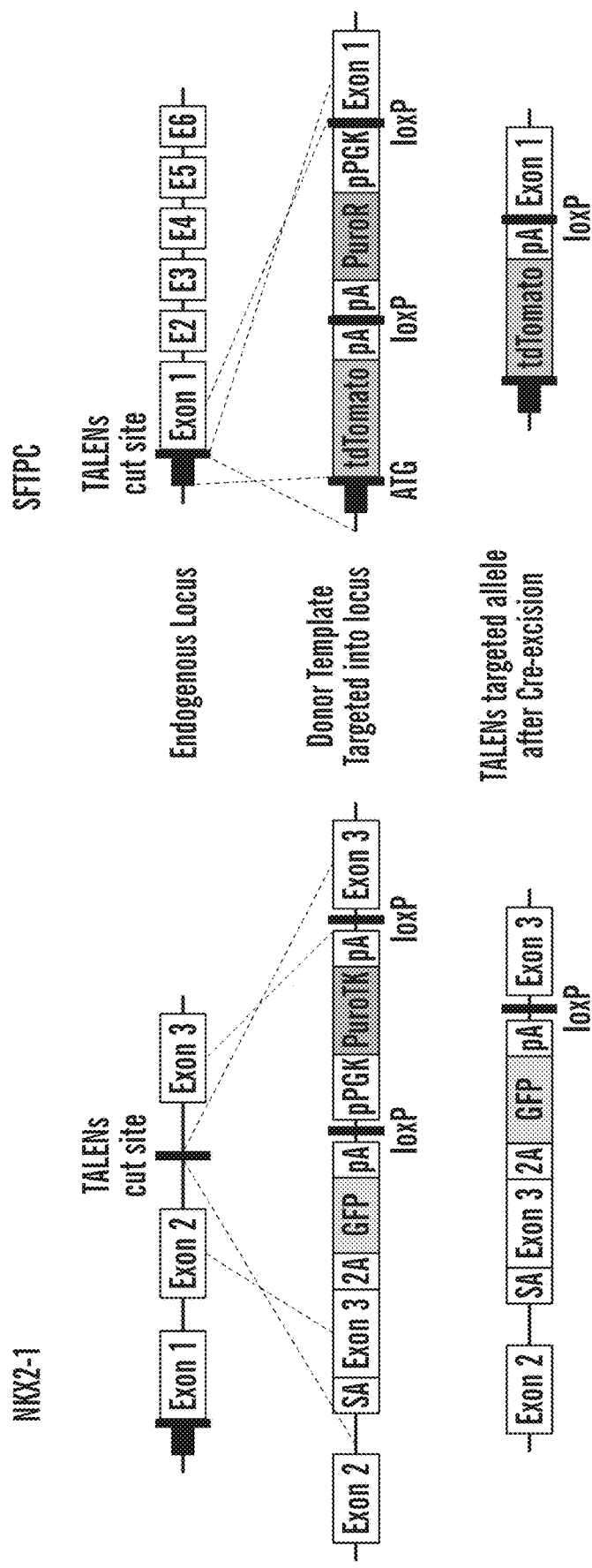
FIGS. 1A-1D demonstrate that NKX2-1GFP and SFTPCtdTomato reporters allow visualization of distal lung differentiation and isolation of putative iAEC2s.

For both therapeutic and research purposes, sources of differentiated cells are highly desireable. Means of in vitro differentiation are of particular interest in order to provide customized and/or personalized populations of differentiated cells. However, the conditions necessary to effectively differentiate many cells types remain unknown. An example of a cell type which could not previously be reliably differentiated in vitro was type II alveolar epithelial cells. Previous attempts to provide pure cultures of type II alveolar epithelial cells have failed, resulting in transdifferentiation to other cell types or the need for mixed cultures (Foster et al. 2007); (Borok et al. 1998); (Barkauskas et al. 2013).

Pulmonary alveolar epithelial type II cell (AEC2) dysfunction has been implicated as a primary cause of pathogenesis in many poorly understood lung diseases that lack effective therapies, including interstitial lung disease (ILD) and emphysema. The methods and compositions described herein permit generation of alveolar cell types, particularly type II alveolar epithelial cells, from stem and/or progenitor cells of any origin. Accordingly, the methods described herein can relate to patient-derived cells for, e.g., disease modeling, drug screening, and cell-based therapy.

Briefly, the methods described herein relate to induction of a combination of FGF signaling, WNT signaling activator modulation, and steroid treatment to generate alveolar spheroids and/or type II alveolar epithelial cells. The surfactant-producing cells produced according to the methods described herein are referred to as induced alveolar epithelial type 2 cells (iAEC2s). In one aspect, described herein is a method of making induced alveolar epithelial type 2 cells (iAEC2s), the method comprising contacting a NKX2-1+ lung epithelial progenitor cell with: i) an agonist of Wnt/beta-catenin signaling; ii) a corticosteroid; and iii) an agonist of cyclicAMP or the cyclicAMP pathway. In some embodiments of any of the aspects, the iAEC2s can be produced as individual cells or as part of alveolar spheroids.

In some embodiments of any of the aspects, a plurality of agonists of Wnt/beta-catenin signaling; a plurality of corticosteroids; and/or a plurality agonists of cyclicAMP or the cyclicAMP pathway can be utilized. In some embodiments of any of the aspects, a single agonist of Wnt/beta-catenin signaling; a single corticosteroid; and/or a single agonist of cyclicAMP or the cyclicAMP pathway can be utilized.

In some embodiments of any of the aspects, the step of contacting the NKX2-1+ lung epithelial progenitor cell with: i) an agonist of Wnt/beta-catenin signaling; ii) a corticosteroid; and iii) an agonist of cyclicAMP or the cyclicAMP pathway is continued for at least about 2 days, at least about 3 days, at least about 5 days, at least about 10 days, or at least about 15 days. In some embodiments of any of the aspects, the NKX2-1+ lung epithelial progenitor cell is kept in contact with i) an agonist of Wnt/beta-catenin signaling; ii) a corticosteroid; and iii) an agonist of cyclicAMP or the cyclicAMP pathway for at least about 2 days, at least about 3 days, at least about 5 days, at least about 10 days, or at least about 15 days, e.g., by repeated addition/provision of the agents and/or by not removing media comprising the agents. In some embodiments of any of the aspects, the step of contacting the NKX2-1+ lung epithelial progenitor cell with: i) an agonist of Wnt/beta-catenin signaling; ii) a corticosteroid; and iii) an agonist of cyclicAMP or the cyclicAMP pathway is continued for at least 2 days, at least 3 days, at least 5 days, at least 10 days, or at least 15 days. In some embodiments of any of the aspects, the NKX2-1+ lung epithelial progenitor cell is kept in contact with i) an agonist of Wnt/beta-catenin signaling; ii) a corticosteroid; and iii) an agonist of cyclicAMP or the cyclicAMP pathway for at least 2 days, at least 3 days, at least 5 days, at least 10 days, or at least 15 days, e.g., by repeated addition/provision of the agents and/or by not removing media comprising the agents.

In some embodiments of any of the aspects, the step of contacting the NKX2-1+ lung epithelial progenitor cell with: i) an agonist of Wnt/beta-catenin signaling; ii) a corticosteroid; and iii) an agonist of cyclicAMP or the cyclicAMP pathway is continued for at least about 3 days. In some embodiments of any of the aspects, the NKX2-1+ lung epithelial progenitor cell is kept in contact with i) an agonist of Wnt/beta-catenin signaling; ii) a corticosteroid; and iii) an agonist of cyclicAMP or the cyclicAMP pathway for at least about 3 days, e.g., by repeated addition/provision of the agents and/or by not removing media comprising the agents. In some embodiments of any of the aspects, the step of contacting the NKX2-1+ lung epithelial progenitor cell with: i) an agonist of Wnt/beta-catenin signaling; ii) a corticosteroid; and iii) an agonist of cyclicAMP or the cyclicAMP pathway is continued for at least 3 days. In some embodiments of any of the aspects, the NKX2-1+ lung epithelial progenitor cell is kept in contact with i) an agonist of Wnt/beta-catenin signaling; ii) a corticosteroid; and iii) an agonist of cyclicAMP or the cyclicAMP pathway for at least 3 days, e.g., by repeated addition/provision of the agents and/or by not removing media comprising the agents.

In one aspect, described herein is a method of making induced alveolar epithelial type 2 cells (iAEC2s), the method comprising a) contacting a NKX2-1+ lung epithelial progenitor cell with: i) an agonist of Wnt/beta-catenin signaling; ii) a corticosteroid; and iii) an agonist of cyclicAMP or the cyclicAMP pathway; and b) culturing the cell resulting from step a) wherein the cell resulting from step a) is not contacted with an agonist of Wnt/beta-catenin signaling during step b). In some embodiments of any of the aspects, the step of culturing the cell resulting from step a) in the absence of an agonist of Wnt/beta-catenin signaling is continued for at least about 3 days, e.g., about 3 days, about 5 days, about 10 days, or more. In some embodiments of any of the aspects, the step of culturing the cell resulting from step a) in the absence of an agonist of Wnt/beta-catenin signaling is continued for at least about 5 days. In some embodiments of any of the aspects, the step of culturing the cell resulting from step a) in the absence of an agonist of Wnt/beta-catenin signaling is continued for at least about 10 days. In some embodiments of any of the aspects, the step of culturing the cell resulting from step a) in the absence of an agonist of Wnt/beta-catenin signaling is continued for at least 3 days, e.g., 3 days, 5 days, 10 days, or more. In some embodiments of any of the aspects, the step of culturing the cell resulting from step a) in the absence of an agonist of Wnt/beta-catenin signaling is continued for at least 5 days. In some embodiments of any of the aspects, the step of culturing the cell resulting from step a) in the absence of an agonist of Wnt/beta-catenin signaling is continued for at least 10 days. The agonist of Wnt/beta-catenin signaling present in step a) can be removed by a number of means known in the art, e.g., by washing the cells, transferring the cells to new media, or providing continuous flow of media lacking the agonist of Wnt/beta-catenin signaling.

In one aspect of any of the embodiments, described herein is a method of making iAEC2s, the method comprising: a) a first culturing step of culturing a population of NKX2-1+ lung epithelial progenitor cells in the presence of: i) an agonist of Wnt/beta-catenin signaling; ii) a corticosteroid; and iii) an agonist of cyclicAMP or the cyclicAMP pathway for a period of at least about 2 weeks; b) a second culturing step of culturing the cells resulting from the first culturing step in the presence of i) a corticosteroid and ii) an agonist of cyclicAMP or the cyclicAMP pathway but not an agonist of Wnt signaling; for a period of at least about 1 week; and c) a third culturing step of culturing the cells resulting from the second culturing step in the presence of: i) an agonist of Wnt/beta-catenin signaling; ii) a corticosteroid; and iii) an agonist of cyclicAMP or the cyclicAMP pathway for a period of at least about 1 week.

In one aspect of any of the embodiments, described herein is a method of making iAEC2s, the method comprising: a) a first culturing step of culturing a population of NKX2-1+ lung epithelial progenitor cells in the presence of: i) an agonist of Wnt/beta-catenin signaling; ii) a corticosteroid; and iii) an agonist of cyclicAMP or the cyclicAMP pathway for a period of at least 2 weeks; b) a second culturing step of culturing the cells resulting from the first culturing step in the presence of i) a corticosteroid and ii) an agonist of cyclicAMP or the cyclicAMP pathway but not an agonist of Wnt signaling; for a period of at least 1 week; and c) a third culturing step of culturing the cells resulting from the second culturing step in the presence of: i) an agonist of Wnt/beta-catenin signaling; ii) a corticosteroid; and iii) an agonist of cyclicAMP or the cyclicAMP pathway for a period of at least 1 week.

In one aspect of any of the embodiments, described herein is a method of making iAEC2s, the method comprising: a) a first culturing step of culturing a population of NKX2-1+ lung epithelial progenitor cells in the presence of: i) an agonist of Wnt/beta-catenin signaling; ii) a corticosteroid; and iii) an agonist of cyclicAMP or the cyclicAMP pathway for a period of at least 3 days; b) a second culturing step of culturing the cells resulting from the first culturing step in the presence of i) a corticosteroid and ii) an agonist of cyclicAMP or the cyclicAMP pathway but not an agonist of Wnt signaling; for a period of at least 5 days; and c) a third culturing step of culturing the cells resulting from the second culturing step in the presence of: i) an agonist of Wnt/beta-catenin signaling; ii) a corticosteroid; and iii) an agonist of cyclicAMP or the cyclicAMP pathway for a period of at least 3 days.

In some embodiments of any of the aspects, one or more agents are used to activate or enhance the Wnt pathway, herein termed "agonists of Wnt/beta-catenin signaling" or "wnt activating agents" or "activating agents" or "Wnt activators". As used herein, "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, Wnt/beta-catenin signaling, e.g. its ability to increase the level and/or activity of Wnt/beta-catenin signaling can be determined, e.g. by measuring the level of an expression product of Wnt/beta-catenin signaling pathway and/or the activity of Wnt/beta-catenin signaling. Methods for measuring the level of a given mRNA and/or polypeptide are known to one of skill in the art, e.g. RTPCR with primers can be used to determine the level of RNA, and Western blotting with an antibody can be used to determine the level of a polypeptide. Antibodies to Wnt/beta-catenin signaling pathway proteins are commercially available. Assays for measuring the activity of Wnt/beta-catenin signaling are known in the art, e.g., WNT Signaling Pathway RT2 Profiler PCR Array Cat. No. PAHS-043Z from Qiagen; Hilden Germany or Wnt/β-Catenin Activated Targets Antibody Sampler Kit Cat No. 8655 from Cell Signaling Technologies Danvers, Mass.

In some embodiments of any of the aspects, Wnt activating agents activate the Wnt/β-catenin pathway directly, for example Wnt activating agents include Wnt or Wnt3a or homologues and variants thereof, as well as β-catenin and components of the Wnt/β-catenin signaling pathway. In other embodiments, Wnt activating agents activate Wnt/β-catenin pathway by inhibiting negatively acting components of the Wnt/β-canetin-GSK3 pathway. For example, a Wnt activating agent can suppress or inhibit the activity and/or expression of Wnt/β-catenin endogenous suppressors, for example a Wnt activating agent can be an inhibitor of GSK3β.

Wnt activating agents of the present invention include, but are not limited to polynucleotides, polypeptides, proteins, peptides, antibodies, small molecules, aptamers, nucleic acids, nucleic acid analogues and other compositions that are capable of activating or enhancing the Wnt/β-catenin pathway, or increasing the activity and/or expression of Wnt, Wnt-dependent genes/proteins and/or β-catenin. Alternatively, Wnt activating agents of the present invention are agents that inhibit the activity and/or expression of genes and/or gene products that suppress the activity and/or expression of wnt or the Wnt/β-catenin pathway including, but not limited to, agents that inhibit GSK-3 or GSK-3β, or sFRP, DKK1, WIF-1 etc.

In some embodiments of any of the aspects, Wnt activating agents activate and/or increase the activity of Wnt homologues and/or Wnt/β-catenin signaling. In some embodiments of any of the aspects, Wnt activating agents are a Wnt gene and/or Wnt gene product, or homologues or genetically modified versions and fragments thereof having Wnt signaling activity. Wnt genes and proteins useful as Wnt activating agents in the present invention are well known to a person of ordinary skill in the art, and include, for example, human and mouse Wnt genes, Wnt homologues and fragments and genetically modified versions thereof that have Wnt signaling activity. Wnt genes include, but are not limited to human Wnt-1, 2A, 2B, 3, 3A, 4, 5A, 5B, 7A, 7B, 8A, 8B, 9A, 9B, 10A, 10B, 11A, and murine Wnt genes, Wnt-1, 2, 3A, 3B, 4, 5A, 5B, 6, 7A, 7B, 8A, 8B, 10B, 11 and 12. Gene or nucleic acid sequences encoding the polypeptides are disclosed in U.S. Pat. Nos. 5,851,984 and 6,159,462, which are incorporated herein by reference in their entireties. In some embodiments of any of the aspects, the Wnt activating agent comprises one or more Wnt gene and/or gene product as mentioned above. In some embodiments of any of the aspects, the Wnt activating agent is Wnt3A gene or Wnt3A gene product or a modified version, homologue or fragment thereof, that has Wnt signaling activity, including, but not limited to (GenBank accession #NM_009522), (GenBank accession #NM_030753); and/or (GenBank accession #NM_033131). Other Wnt activating agents that activate Wnt/β-catenin signaling can be used, for example compositions listed and discussed in U.S. Pat. Nos. 5,851,984 and 6,159,462 which are incorporated herein by reference in their entirety.

In alternative embodiments, Wnt activating agents include but are not limited to disheveled WLS/Evi, (dsh), LRP-5, LRP-6, Daily (division abnormally delayed), Dally-like, PAR1, β-catenin, TCF, lef-1 and Frodo or homologues or genetically modified versions thereof that retain wnt activating activity. In some embodiments of any of the aspects, Wnt activating agents are inhibitory molecules to endogenous extracellular inhibitors of Wnt/β-catenin signalling, for example inhibitors that inhibit their activity and/or expression, for example inhibitory nucleic acid of WIF-1, cerberus, Dickkopf-1 (DKK1), Dapper, pertussis toxin, disabled-2 (dab-2), naked cuticle (naked), Frzb-related proteins, FrzA, frzB, sizzled sFRP (secreted frizzled-related proteins), sRFP-1, sFRP-2, collagen 18 (XVIII), endostatin, carboxypeptidase Z, receptor tyrosine kinase, corin etc.

In further aspects, Wnt activating agents trigger Wnt/β-catenin signaling by activating and/or increasing the activity of β-catenin, for example, that stabilize and/or increase cytosolic accumulation of β-catenin and/or inhibit its phosphorylation. In some embodiments of any of the aspects, Wnt activating agents are β-catenin gene and/or β-catenin gene product, or homologues, genetically modified version or fragments thereof that retain wnt activating activity. β-catenin gene and gene product are known to persons of ordinary skill in the art, and include but are not limited to (GenBank accession #XM_208760). In some embodiments of any of the aspects, wnt activating agents are stabilized versions of β-catenin, for example versions where serine residues of the GSK-3β phosphorylation consensus motif of β-catenin have been substituted, resulting in inhibition of ubiquitination and stabilization of the protein. Examples of stabilized β-catenins include, but are not limited to those with the amino acid changes D32Y; D32G; S33F; S33Y; G34E; S37C; S37F; T41I; S45Y; and deletion of AA 1-173 relative to human β-catenin. A number of publications describe stabilized β-catenin mutations, for example, see Morin et al., 1997; Palacios et al., 1998; Muller et al., 1998; Miyoshi et al., 1998; Zurawel et al., 1998; Voeller et al., 1998; and U.S. Pat. No. 6,465,249, etc., which are incorporated herein in their entirety by reference. In alternative embodiments, other Wnt activating agents that activate β-catenin can be used, for example compositions discussed in U.S. Pat. No. 6,465,249, which is incorporated herein in its entirety by reference.

In some embodiments of any of the aspects, Wnt activating agents are any β-catenin binding partners that increase the stability of β-catenin and/or promote β-catenin localization in the nucleus. In alternative embodiments, Wnt activating agents include, but are not limited to Frodo, TCF, pitx2, Reptin 52, legless (lgs), pygopus (pygo), hyrax/parafbromin, LKBI/XEEK1 or homologues or modified versions or fragments thereof that retain Wnt activating activity. In alternative embodiments, Wnt activating agents are inhibitors of negative factors, for example inhibitory nucleic acids and/or peptides that inhibit the activity and/or gene expression of, for example but not limited to APC, Axin, dab-2, grucho, PP2A, chibby, pontin 52, Nemo/LNK kinases etc.

In some embodiments of any of the aspects, Wnt activating agents useful in the present invention are inhibitors of GSK-3 and/or GSK-3β. Examples of inhibitors of GSK-3 inhibitors include but are not limited to BIO (6-bromoindirubin-3'oxime), acetoxime analogue of BIO, 1-azakenpaullone or analogues or modified versions thereof. Any agent which inhibits GSK3β is potentially useful as a Wnt activating agent in the methods described herein, and includes, for example lithium, LiCl, Ro31-8220, as disclosed in International Patent Application No: PCT97/41854, which is incorporated herein in its entirety by reference, and retinoic acid.

In some embodiments of any of the aspects, other Wnt activating agents that inhibit GSK-3 can be used, for example compositions disclosed in U.S. Pat. No. 6,411,053, which is incorporated herein by reference in its entirety. The present invention also encompasses all GSK-3 inhibitors, including those discovered as GSK-3 inhibitors by the methods disclosed in International Patent Application No: PCT97/41854, which is incorporated herein in its entirety by reference.

It is encompassed in the present invention that Wnt activating agents activate or enhance Wnt/β-catenin signaling in the NKX2-1 lung epithelial progenitor cells. For example, Wnt activating agents can be delivered to the culture media of the NKX2-1 lung epithelial progenitor cells, and in some embodiments the wnt activating agent is delivered to the NKX2-1 lung epithelial progenitor cells as a polynucleotide and/or a polypeptide. The polynucleotide can be comprised in a vector, (i.e., a viral vector and/or non-viral vector). Examples of the viral vectors include, but are not limited to adenoviral vectors, adeno-associated vectors, retroviral vectors or lentiviral vectors. Alternatively, wnt activating agents may be delivered to a feeder layer, such that the Wnt/β-catenin signalling is promoted in the feeder layer. In one embodiment, the feeder layer may comprise 'Wnt activating agent-producing cells'. In alternative embodiments, Wnt activating agents are delivered to the NKX2-1 lung epithelial progenitor cells and/or the feeder layer. In some embodiments of any of the aspects, more than one Wnt activating agent is delivered to the NKX2-1 lung epithelial progenitor cells and/or feeder layer, and in some embodiments of any of the aspects, the Wnt activating agents delivered to the NKX2-1 lung epithelial progenitor cells are different from those delivered to the feeder cell layer. In some embodiments of any of the aspects, the Wnt activating agent can be encoded in a nucleic acid operatively linked to a promoter, and in some embodiments the promoter is, for example, a tissue-specific promoter or an inducible promoter.

Non-limiting examples of agonists of Wnt/beta-catenin signaling can include CHIR99021; a recombinant Wnt polypeptide; a Wnt polypeptide (e.g., a polypeptide expression product of human Wnt-1, 2A, 2B, 3, 3A, 4, 5A, 5B, 7A, 7B, 8A, 8B, 9A, 9B, 10A, 10B, and/or 11A); an exogenous Wnt polypeptide; BIO; WAY-316606; a (hetero) arylpyrimidine; IQ1; QS11; SB-216763; DCA; R-spondin; and an inhibitor of Axin2 (e.g., NCBI Gene ID: 8313 and orthologs thereof) and/or APC (e.g., NCBI Gene ID: 324 and orthologs thereof).

As used herein, the term "corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term "corticosteroid" can include, but is not limited to, the following generic and brand name corticosteroids: cortisone (CORTONE™ ACETATE™, ADRESON™, ALTESONA™, CORTELAN™, CORTISTAB™, CORTISYL™, CORTOGEN™, CORTONE™, SCHEROSON™); dexamethasone-oral (DECADRON-ORAL™, DEXAMETH™, DEXONE™, HEXADROL-ORAL™, DEXAMETHASONE™ INTENSOL™, DEXONE 0.5™, DEXONE 0.75™, DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™, DELTA-CORTEF™, PEDIAPRED™, ADNISOLONE™, CORTALONE™, DELTACORTRIL™, DELTASOLONE™, DELTASTAB™, DI-ADRESON F™ ENCORTOLONE™, HYDROCORTANCYL™, MEDISOLONE™, METICORTELONE™, OPREDSONE™, PANAAFCORTELONE™, PRECORTISYL™, PRENISOLONA™, SCHERISOLONA™, SCHERISOLONE™); prednisone (DELTASONE™, LIQUID PRED™, METICORTEN™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™, CORDROL™, CORTAN™, DACORTIN™, DECORTIN™, DECORTISYL™, DELCORTIN™, DELLACORT™, DELTADOME™, DELTACORTENE™, DELTISONA™, DIADRESON™ ECONOSONE™, ENCORTON™, FERNISONE™, NISONA™, NOVOPREDNISONE™, PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-D™, TRIMED™, TRIAMCOT™, TRISTOPLEX™, TRYLONE D™, U-TRI-LONE™). In some embodiments of any of the aspects, a corticosteroid can be a corticosteroid which is active when applied topically, including, but not limited to clobetasol propionate, betamethasone valerate, betamethasone dripropionate, and mometasone furoate. In some embodiments of any of the aspects, a corticosteroid can be dexamethasone (e.g. a compound having the structure of Formula I); prednisone (e.g. a compound having the structure of Formula II); prednisolone (e.g. a compound having the structure of Formula III); triamcinolone (e.g. a compound having the structure of Formula IV); clobetasol propionate; betamethasone valerate (e.g. a compound having the structure of Formula V); betamethasone dipropionate (e.g. a compound having the structure of Formula VI); or mometasone furoate. Methods of synthesizing corticosteroids are well known in the art and such compounds are also commercially available, e.g. dexamethasone (Cat. No. D4902, Sigma-Aldrich; St. Louis, Mo.) and predinsone (Cat. No. P6254, Sigma-Aldrich; St. Louis, Mo.).

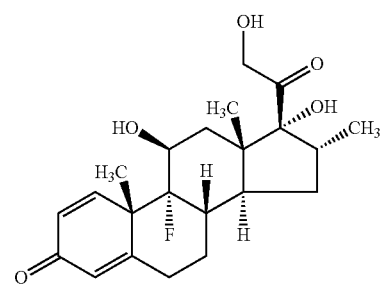

Formula I

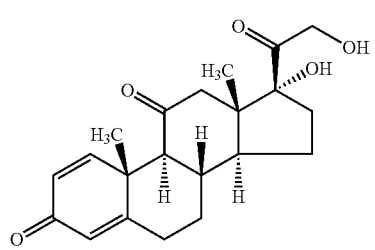

Formula II

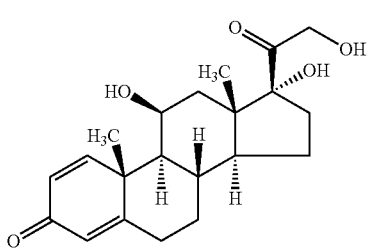

Formula III

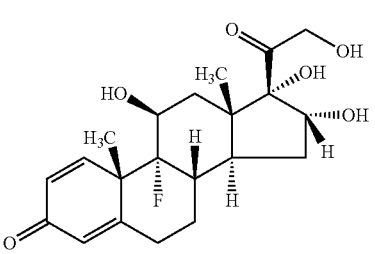

Formula IV

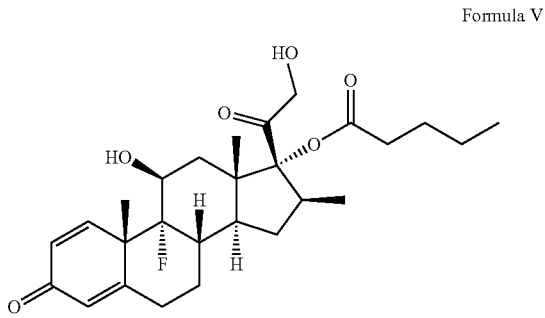

Formula V

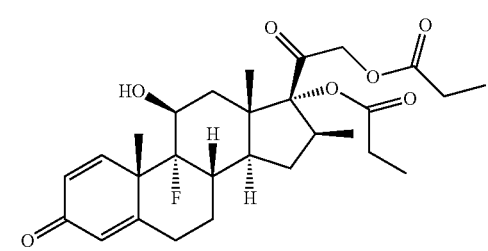

Formula VI

Non-limiting examples of corticosteroids can include dexamethasone; hydrocortisone; cortisone; prednisone; prednisolone; methylprednisolone; triamncinolone; betamethasone; fludrocortisone acetate; and deoxycorticosterone acetate. In some embodiments of any of the aspects, the corticosteroid is dexamethasone.

As used herein, "cyclicAMP pathway" refers to the adenyl cyclase pathway, in which an activated GPCR binds to and activated adenylyl cyclase, converting ATP to cAMP. Increased levels of cAMP can activate ion channels, exchange proteins (e.g., RAPGEF3), popeye domain proteins (Popdc), and/or protein kinase A (PKA). Methods for measuring the level of cAMP and/or a part of the cAMP pathway are known in the art, e.g., cAMP XP™ Chemiluminescent Assay Kit (Cat. No. 8019, Cell Signaling Technology, Danvers Mass.) and cAMP Calcium Signaling PathwayFinder RT2 Profiler PCR Array (Cat No. PAHS-066Z, Qiagen, Hilden Germany).

Non-limiting examples of agonists of cAMP and/or the cAMP pathway can include cAMP, IBMX, cholera toxin, forskolin, caffeine, bucaldesine, and pertussis toxin. Further non-limiting examples agonists of cAMP and/or the cAMP pathway can include cAMP mimetics, analogs, diburtyryl cAMP; 8-bromo-cAMP; phorbol ester; sclareline; aminophylline; 2,4 dinitrophenol (DNP); norepinephrine; epinephrine; isoproterenol; isobutylmethylxanthine (IBMX); theophylline (dimethylxanthine); dopamine; rolipram; iloprost; prostaglandin $E_1$; prostaglandin $E_2$; pituitary adenylate cyclase activating polypeptide (PACAP); vasoactive intestinal polypeptide (VIP); (S)-adenosine; cyclic 3',5'-(hydrogenphosphorothioate)triethyl ammonium; 8-bromoadenosine-3',5'-cyclic monophosphate; 8-chloroadenosine-3',5'-cyclic monophosphate; and N6,2'-O-dibutyryladenosine-3',5'-cyclic monophosphate.

In some embodiments of any of the aspects, the agonist of Wnt/beta-catenin signaling is CHIR99021, the corticosteroid is dexamethasone, and the agonist of cAMP is cAMP.

In some embodiments of any of the aspects, any cell described herein can be further contacted with or cultured with a second agonist of cyclicAMP or the cyclicAMP pathway, e.g., during any of the contacting or culturing steps described herein.

In some embodiments of any of the aspects, a NKX2-1+ lung epithelial progenitor cell, during the step of contacting the NKX2-1+ lung epithelial progenitor cell with i) an agonist of Wnt/beta-catenin signaling; ii) a corticosteroid; and iii) a first agonist of cyclicAMP or the cyclicAMP pathway, is further contacted with a second agonist of cyclicAMP or the cyclicAMP pathway.

In some embodiments of any of the aspects, a NKX2-1+ lung epithelial progenitor cell, during the first culturing step of contacting the NKX2-1+ lung epithelial progenitor cell with i) an agonist of Wnt/beta-catenin signaling; ii) a corticosteroid; and iii) a first agonist of cyclicAMP or the cyclicAMP pathway, is further contacted with a second agonist of cyclicAMP or the cyclicAMP pathway. In some embodiments of any of the aspects, a NKX2-1+ lung epithelial progenitor cell, during the second culturing step of contacting the cell with i) a corticosteroid; and ii) a first agonist of cyclicAMP or the cyclicAMP pathway, is further contacted with a second agonist of cyclicAMP or the cyclicAMP pathway. In some embodiments of any of the aspects, a cell, during the third culturing step of contacting the NKX2-1+ lung epithelial progenitor cell with i) an agonist of Wnt/beta-catenin signaling; ii) a corticosteroid; and iii) a first agonist of cyclicAMP or the cyclicAMP pathway, is further contacted with a second agonist of cyclicAMP or the cyclicAMP pathway.

In some embodiments of any of the aspects, the second agonist of cyclicAMP or the cyclicAMP pathway is IBMX.

In some embodiments of any of the aspects, any cell described herein can be further contacted with or cultured with 3-isobutyl-1-methylxanthine (IBMX), e.g., during any of the contacting or culturing steps described herein.

In some embodiments of any of the aspects, a NKX2-1+ lung epithelial progenitor cell, during the step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with 3-isobutyl-1-methylxanthine (IBMX).

In some embodiments of any of the aspects, a NKX2-1+ lung epithelial progenitor cell, during the first culturing step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with 3-isobutyl-1-methylxanthine (IBMX). In some embodiments of any of the aspects, a NKX2-1+ lung epithelial progenitor cell, during the second culturing step of contacting the cell with i) a corticosteroid; and ii) an agonist of cyclicAMP or the cyclicAMP pathway, is further contacted with 3-isobutyl-1-methylxanthine (IBMX). In some embodiments of any of the aspects, a cell, during the third culturing step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with 3-isobutyl-1-methylxanthine (IBMX).

In some embodiments of any of the aspects, any cell described herein can be further contacted with or cultured with an agonist of FGF signaling, e.g., during any of the contacting or culturing steps described herein.

In some embodiments of any of the aspects, a NKX2-1+ lung epithelial progenitor cell, during the step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with an agonist of FGF signaling.

In some embodiments of any of the aspects, a NKX2-1+ lung epithelial progenitor cell, during the first culturing step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with an agonist of FGF signaling. In some embodiments of any of the aspects, a NKX2-1+ lung epithelial progenitor cell, during the second culturing step of contacting the cell with i) a corticosteroid; and ii) an agonist of cyclicAMP or the cyclicAMP pathway, is further contacted with an agonist of FGF signaling. In some embodiments of any of the aspects, a cell, during the third culturing step of contacting the NKX2-1+ lung epithelial progenitor cell with i) an agonist of Wnt/beta-catenin signaling; ii) a corticosteroid; and iii) an agonist of cyclicAMP or the cyclicAMP pathway, is further contacted with an agonist of FGF signaling.

As used herein, "FGF signaling" refers to signaling activity mediated by the binding of a fibroblast growth factor receptor (FGFR) family member (e.g., FGFR1, FGFR2, FGFR3, or FGFR4) by a ligand and heparin sulfate, which can activate a number of downstream signaling cascades. FGFR ligands are known in the art and include the more than 20 fibroblast growth factors (FGFs). FGF signaling can promote growth and/or proliferation and is known to regulate development of numerous tissues. Methods for measuring FGF signaling activity are known in the art, e.g., the Qiagen Growth Factor PCR Array (Cat. No. PAHS-041Z; Hilden, Germany).

Exemplary agonists of FGF signaling can include, but are not limited to KGF (also referred to in the art as FGF7) polypeptides (e.g., polypeptides of NCBI Gene ID No: 2252 or orthologs thereof); FGF1 polypeptides (e.g., polypeptides of NCBI Gene ID No: 2246 or orthologs thereof); FGF2 polypeptides (e.g., polypeptides of NCBI Gene ID No: 2247 or orthologs thereof); FGF3 polypeptides (e.g., polypeptides of NCBI Gene ID No: 2248 or orthologs thereof); FGF4 polypeptides (e.g., polypeptides of NCBI Gene ID No: 2249 or orthologs thereof); FGF6 polypeptides (e.g., polypeptides of NCBI Gene ID No: 2251 or orthologs thereof); FGF8 polypeptides (e.g., polypeptides of NCBI Gene ID No: 2253 or orthologs thereof); FGF9 polypeptides (e.g., polypeptides of NCBI Gene ID No: 2254 or orthologs thereof); FGF10 polypeptides (e.g., polypeptides of NCBI Gene ID No: 2255 or orthologs thereof); FGF17 polypeptides (e.g., polypeptides of NCBI Gene ID No: 8822 or orthologs thereof); FGF18 polypeptides (e.g., polypeptides of NCBI Gene ID No: 8817 or orthologs thereof); FGF22 polypeptides (e.g., polypeptides of NCBI Gene ID No: 27006 or orthologs thereof); a FGF receptor ligand (e.g., dekafin-2; fragments of FGFs with receptor binding activity, a naturally-occurring FGF); and a small molecule agonist of FGF signaling (e.g., SUN11602). Further examples of small molecule agonists of FGF signaling can be found, e.g., in U.S. Pat. No. 9,034,898 which is incorporated by reference herein in its entirety. In some embodiments of any of the aspects, the agonist of FGF signaling is a KGF and/or FGF10 polypeptide. In some embodiments of any of the aspects, the agonist of FGF signaling is a KGF polypeptide.

As used herein, the term "a progenitor cell" refers to an immature or undifferentiated cell that has the potential later on to mature (differentiate) into a specific cell type, for example, a blood cell, a skin cell, a bone cell, or a hair cells. Progenitor cells have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. A progenitor cell also can proliferate to make more progenitor cells that are similarly immature or undifferentiated. Accordingly, as used herein, "lung epithelial progenitor cell" refers to a progenitor cell with the differentiation potential to form one or more types of lung epithelial cells. In some embodiments of any of the aspects, lung epithelial progenitor cells can be NKX2-1$^+$ FOXA2$^+$ cells. In some embodiments of any of the aspects, lung epithelial progenitor cells can be NKX2-1$^+$ FOXA2$^+$ epithelial cells. In some embodiments of any of the aspects, lung epithelial progenitor cells can be NKX2-1$^+$ FOXA2$^+$ epithelial cells that can give rise to cells that express mature lung epithelial markers (e.g., SFTPC, SCGB3A2, P63, SFTPB, HOPX, PDPN, SCGB1A1, FOXJ1). In some embodiments of any of the aspects, a lung epithelial progenitor cell is NKX2-1$^+$ and STPC$^-$. In some embodiments of any of the aspects, a lung epithelial progenitor cell is NKX2-1$^+$ FOXA2$^+$ and STPC$^-$.

As used herein, "NKX2-1", "NK2 homeobox 1", "or thyroid transcription factor 1 (TTF-1) refers to a transcription factor that controls gene expression specifically in the thyroid, lung, and diencephalon. It is also known as thyroid specific enhancer binding protein. Sequences are known for the sequence of NKX2-1 genes and polypeptides for a number of species, e.g., human NKX2-1 (NCBI Gene ID No: 7080) mRNA (e.g., NCBI Ref Seq: NM_001079668.2 and 2.NM_003317.3) and polypeptide (e.g., NCBI Ref Seq: NP_001073136.1 and NP_003308.1).

In some embodiments of any of the aspects, a NKX2-1+ cell is a cell expressing a detectable quantity of NKX2-1 polypeptide. In some embodiments of any of the aspects, a NKX2-1$^{Hi}$ cell belongs to a first subpopulation (NKX2-1$^{Hi}$) of cells expressing a relatively higher amount of NKX2-1 polypeptide as compared to a second subpopulation) (NKX2-1$^{Lo}$ of cells expressing a relatively lower amount of NKX2-1 polypeptide, wherein both subpopulations are part of the same total population (e.g. a population of cells obtained from the same source). In some embodiments of any of the aspects wherein a NKX2-1+ cell is referred to, a NKX2-1$^{Hi}$ cell can be used as an alternative embodiment.

In some embodiments of any of the aspects, the NKX2-1+ lung epithelial progenitor cell is a CD47hi/CD26lo cell, wherein CD47 is a polypeptide of NCBI Gene ID: 961 or an ortholog thereof and CD26 is a polypeptide of NCBI Gene ID: 1803 or an ortholog thereof. In some embodiments of any of the aspects, a CD47hi/CD26lo cell is a cell sorted from a population of cells for a CD47hi/CD26lo phenotype. In some embodiments of any of the aspects, the NKX2-1+ lung epithelial progenitor cell is provided by sorting lung epithelial progenitor cells to isolate a CD47hi/CD26lo population.

NKX2-1+ lung epithelial progenitor cells can be obtained from any source known in the art, e.g., by isolating such cells from a subject or tissue and/or by differentiating such cells from a less differentiated cell type, e.g., a stem cell or epithelial progenitor cell type. In some embodiments of any of the aspects, the NKX2-1+ lung epithelial progenitor cell is derived from a stem cell, an induced pluripotent stem cell (iPSC), an embryonic stem cell, and/or a somatic stem cell. In some embodiments, the NKX2-1+ lung epithelial progenitor cell is derived from a cell obtained from a subject, e.g., a subject having, diagnosed as having, or in need of treatment for a lung disease.

In some embodiments of any of the aspects, the NKX2-1+ lung epithelial progenitor cell is derived from a less differentiated cell by contacting the less differentiated cell with CHIR99021, BMP4 (e.g., a polypeptide of NCBI Gene ID: 652 or an ortholog thereof), and retinoic acid (RA).

In some embodiments of any of the aspects, the methods described herein can further comprise first genetically modifying the NKX2-1+ lung epithelial progenitor cell or a less differentiated cell the NKX2-1+ lung epithelial progenitor cell is derived from. Such genetic modifications can include, e.g., deletion or mutation of genes involved in lung pathologies, correction of mutations involved in lung pathologies, introduction of exogenous copies of genes involved in lung pathologies, introduction of markers and/or reporter constructs, and the like.

The methods described herein provide advantages and/or improvements over prior art methods in that the presence of mesenchymal cells is not necessary, thereby improving the purity of the iAEC2s populations that can be obtained by the presently described methods. In some embodiments of any of the aspects, the NKX2-1+ lung epithelial progenitor cell is not contacted or cultured with a mesenchymal cell. In some embodiments of any of the aspects, a mesenchymal cell is not present during any step of the methods described herein. In some embodiments of any of the aspects, a mesenchymal cell is not added or provided during any step of the methods described herein.

In some embodiments of any of the aspects, the NKX2-1+ lung epithelial progenitor cell is not contacted or cultured with a feeder cell layer. In some embodiments of any of the aspects, a feeder cell layer is not present during any step of the methods described herein. In some embodiments of any of the aspects, a feeder cell layer is not added or provided during any step of the methods described herein.

In some embodiments of any of the aspects described herein, cells can be sorted and/or selected before or after any contacting or culturing step described herein, e.g., lung epithelial progenitor cells can be sorted to increase the percentage of NKX2-1+ cells present in a population after differentiation from an iPSC and/or cells can be sorted after the contacting steps to increase the percentage of iAEC2s present in a population. Methods of sorting and selecting cells are known in the art, e.g., FACs, flow cytometry, magnetic bead based sorting, and microfluidic chip based sorting using cell fluorescence, or the like.

The NKX2-1+ lung epithelial progenitor cell can be provided as an isolated cell, as a member of a pure population of NKX2-1+ lung epithelial progenitor cells, or as a member of a mixed population of cells. In some embodiments of any of the aspects, the NKX2-1+ lung epithelial progenitor cell can be provided as a member of a population of cells which are at least 50% NKX2-1+ lung epithelial progenitor cells, e.g., at least 50%, at least 60%, at least 70%, at least 80%, at least 90% NKX2-1+ lung epithelial progenitor cells or more. In some embodiments of any of the aspects, the NKX2-1+ lung epithelial progenitor cell can be provided as a member of a population of cells which are at least 50% NKX2-1+ cells, e.g., at least 50%, at least 60%, at least 70%, at least 80%, at least 90% NKX2-1+ cells or more.

An iAEC2 obtained and/or produced according to the method described herein can be an isolated cell, a member of a pure population of iAEC2s, or as a member of a mixed population of cells. In some embodiments of any of the aspects, the iAEC2 can be provided as a member of a population of cells which are at least 50% iAEC2s, e.g., at least 50%, at least 60%, at least 70%, at least 80%, at least 90% iAEC2s or more.

The cells described herein can be eukaryotic cells, mammalian cells, or human cells. In some embodiments of any of the aspects, a cell described herein can be a human cell. In some embodiments of any of the aspects, a cell described herein can be a mammalian cell.

In some embodiments of any of the aspects, an iAEC2 cell is a NKX2-1+/SFTPC+ cell. In some embodiments of any of the aspects, an iAEC2 cell is a NKX2-1+/SFTPC$^{Hi}$ cell. As used herein "SFTPC" refers to pulmonary surfactant-associated protein C, a membrane protein which produces surfactant. Sequences for SFTPC genes, mRNA, and polypeptides are known for a number of species, e.g., human SFTPC (NCBI Gene ID No: 6440) mRNA (e.g., NCBI Ref Seq: NM_001172357.1; NM_001172410.1; NM_001317778.1; NM_001317779.1; NM_001317780.1; and NM_003018.3) and polypeptide (e.g., NCBI Ref Seq: NP_001165828.1; NP 001165881.1; NP 001304707.1; NP 001304708.1; NP 001304709.1; and NP 003009.2).

In one aspect of any of the embodiments, described herein is an iAEC2 cell produced according to a method described herein.

The iAEC2s produced by the methods described herein can be stable in culture (e.g., viable and consistent in an iAEC2 phenotype) for at least 1 month, e.g., at least 1 month, at least 2 months, at least 3 months, or more.

In some embodiments of any of the aspects, the iAEC2s described herein are karyotpically normal. In some embodiments of any of the aspects, the iAEC2s described herein are karyotpically normal in culture (e.g., viable and consistent in an iAEC2 phenotype) for at least 1 month, e.g., at least 1 month, at least 2 months, at least 3 months, or more. Karyotypically normal refers to having a set of chromosomes which have the wild-type number, size, and structure for a cell of that type and/or species. In some embodiments, karyotypically normal can refer to having a set of chromosomes with the same number, size, and structure as the progenitor cell the iAEC2 is produced from.

In one aspect of any of the embodiments, described herein is a method of treating a lung disease in a subject in need thereof, the method comprising administering to the subject an iAEC2 cell, e.g., a iAEC2 cell produced according to a method described herein. As used herein "lung disease" refers to any pathology or condition affecting and/or arising in the lungs (e.g., including the bronchi, aleveoli, pleura, muscles and/or nerves of the lung). In some embodiments of any of the aspects, the lung disease is not an infectious lung disease. In some embodiments of any of the aspects, a lung disease can be an alveolar disease, e.g., a disease characterized by damage to and/or dysfunction of the alveolae. In some embodiments of any of the aspects, a lung disease can be an AEC2-associated lung disease, e.g., a disease characterized by damage to and/or dysfunction of the alveolae and in particular, the AEC2 cells of the alveolae. In some embodiments of any of the aspects, the lung disease can be a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and/or emphsysema.

In some embodiments of any of the aspects, a therapeutically effective amount of iAEC2s are administered to the subject. In some embodiments of any of the aspects, the iAEC2 is derived from a cell obtained from the subject. In some embodiments of any of the aspects, the iAEC2 is autologous to the subject. In some embodiments of any of the aspects, the NKX2-1+ lung epithelial progenitor cell or the less differentiated cell the NKX2-1+ lung epithelial progenitor cell is derived from was genetically modified to correct a mutation that contributed to the lung disease. Such mutations are known in the art and readily identified by one of ordinary skill in the art and/or, e.g., by genetic testing of the subject.

In some embodiments of any of the aspects, the methods described herein relate to treating a subject having or diagnosed as having lung disease with an iAEC2. Subjects having lung disease can be identified by a physician using current methods of diagnosing lung diseases. Symptoms and/or complications of, e.g., interstitial lung disease (ILD) which characterize these conditions and aid in diagnosis are well known in the art and include but are not limited to, reduced lung function, trouble breathing, or shortness of breath. Tests that may aid in a diagnosis of, e.g. ILD include, but are not limited to, pulmonary function tests, biopsies, chest xrays, and/or chest CTs. A family history of ILD, or exposure to risk factors for ILD (e.g. lung infections) can also aid in determining if a subject is likely to have ILD or in making a diagnosis of ILD.

The compositions and methods described herein can be administered to a subject having or diagnosed as having a lung disease. In some embodiments of any of the aspects, the methods described herein comprise administering an effective amount of compositions described herein, e.g. an iAEC2 to a subject in order to alleviate a symptom of a lung disease. As used herein, "alleviating a symptom of a lung disease" is ameliorating any condition or symptom associated with the lung disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

In some embodiments of any of the aspects described herein, the administration of an iAEC2 can improve and/or increase surfactant production in the lung. In some embodiments of any of the aspects described herein, an iAEC2 is administered to a subject in need of improved and/or increased surfactant production in the lung.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for lung function and/or surfactant production, among others. The dosage can be determined by a physician and adjusted, as necessary, to suit observed effects of the treatment.

In some embodiments of any of the aspects, the technology described herein relates to a pharmaceutical composition comprising an iAEC2 and/or an iAEC2 produced by the methods described herein, and optionally a pharmaceutically acceptable carrier. In some embodiments of any of the aspects, the active ingredients of the pharmaceutical composition comprise an iAEC2 and/or an iAEC2 produced by the methods described herein as described herein. In some embodiments of any of the aspects, the active ingredients of the pharmaceutical composition consist essentially of an iAEC2 and/or an iAEC2 produced by the methods described herein as described herein. In some embodiments of any of the aspects, the active ingredients of the pharmaceutical composition consist of an iAEC2 and/or an iAEC2 produced by the methods described herein as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. an iAEC2 and/or an iAEC2 produced by the methods described herein as described herein.

In some embodiments of any of the aspects, the pharmaceutical composition comprising an iAEC2 and/or an iAEC2 produced by the methods described herein as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an iAEC2 and/or an iAEC2 produced by the methods described herein as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, a pharmaceutical composition comprising the cells, e.g., an iAEC2 and/or an iAEC2 produced by the methods described herein, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of cells can be apportioned into multiple infusions that cumulatively equal or exceed $10^5$, $10^6$, $10^7$, $10^8$, $10^9$, $10^{10}$, $10^{11}$, or $10^{12}$ cells.

In some embodiments of any of the aspects, the dosage can be from about $1\times10^5$ cells to about $1\times10^8$ cells per kg of body weight. In some embodiments of any of the aspects, the dosage can be from about $1\times10^6$ cells to about $1\times10^7$ cells per kg of body weight. In some embodiments of any of the aspects, the dosage can be about $1\times10^6$ cells per kg of body weight. In some embodiments of any of the aspects, one dose of cells can be administered. In some embodiments of any of the aspects, the dose of cells can be repeated, e.g., once, twice, or more. In some embodiments of any of the aspects, the dose of cells can be administered on, e.g., a daily, weekly, or monthly basis. iAEC2 compositions may be administered multiple times at dosages within these ranges. The cells may be allogeneic, syngeneic, xenogeneic, or autologous to the patient undergoing therapy.

In some embodiments of any of the aspects, the methods described herein can further comprise administering a second agent and/or treatment to the subject, e.g. as part of a combinatorial therapy.

In certain embodiments, an effective dose of a composition comprising an iAEC2 and/or an iAEC2 produced by the methods described herein as described herein can be administered to a patient once. In certain embodiments, an effective dose of a composition comprising an iAEC2 and/or an iAEC2 produced by the methods described herein can be administered to a patient repeatedly.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an iAEC2 and/or an iAEC2 produced by the methods described herein can be administered over a period of time, such as over a 5 minute, 10 minute, 15 minute, 20 minute, or 25 minute period.

The dosage ranges for the administration of an iAEC2 and/or an iAEC2 produced by the methods described herein, according to the methods described herein depend upon, for example, the form of the composition, its potency, and the extent to which symptoms, markers, or indicators of a condition described herein are desired to be reduced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of an iAEC2 and/or an iAEC2 produced by the methods described herein in, e.g. the treatment of a condition described herein, or to induce a response as described herein (e.g. lung function and/or surfactant production) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. surfactant production and/or lung function. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of a murine models of lung diseases described herein. When using an experimental animal model, efficacy of treatment is evidenced when a statistically significant change in a marker is observed, e.g. surfactant production and/or lung function.

In one aspect, described herein is a kit comprising a composition as described herein, e.g., an iAEC2 and/or an iAEC2 produced by the methods described herein. A kit is any manufacture (e.g., a package or container) comprising at least one reagent, e.g., a cell, the manufacture being promoted, distributed, or sold as a unit for performing the methods described herein. The kits described herein can optionally comprise additional components useful for performing the methods described herein. By way of example, the kit can comprise fluids (e.g., buffers) suitable for a composition comprising an iAEC2 and/or an iAEC2 produced by the methods described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

In one aspect of any of the embodiments, described herein is a method of identifying a treatment as effective in treating a lung disease, the method comprising: a) contacting an iAEC2 (e.g., an iAEC2 produced according to a method described herein) with a candidate treatment agent; and b) identifying the candidate treatment agent as effective if one or more of the following phenotypes is observed in the iAEC2 contacted with the candidate treatment agent as compared to an iAEC2 not contacted with the candidate treatment agent:

i) increased cell survival (e.g., an increase in the length of cell survival, average length of cell survival in population of iAEC2s, or rate of cell survival at a given time point in a population of iAEC2s);
  ii) increased cell survival in the presence of cellular stressors (e.g., wherein cellular stressors can be toxins, conditions that limit nutrients and/or function, conditions that mimic a lung disease pathology or etiology (e.g. excessive mucus levels), and/or stimuli that contribute to lung disease, e.g., cigarette smoke);
  iii) decreased release of toxic agents (e.g., inflammatory cytokines or chemokines, reactive oxygen species, or apoptotic factors);
  iv) improved cellular pathology arising from a genetic mutation in the iAEC2 (e.g., decreased signs or symptoms of a disease in an iAEC2 comprising a mutation associated with and/or causing a lung disease);
  v) increased iAEC2 differentiation (e.g., increased rate or speed of iAEC2 production in a method described herein);
  vi) decreased iAEC2 proliferation in the presence of carcinogens; and/or
  vii) increased secretion of cytoprotective agents (e.g., antiinflammtory cytokines or chemokines, antioxidant molecules or molecules involved in xenobiotic metabolism).

In some embodiments of any of the aspects, iAEC2 is derived from a cell obtained from an individual subject and the treatment is identified as an effective treatment for that individual subject.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

As used herein, the terms "candidate compound" or "candidate agent" refer to a compound or agent and/or compositions thereof that are to be screened for their ability to, e.g., treat a lung disease. Candidate compounds and/or agents can be produced recombinantly using methods well known to those of skill in the art (see Sambrook et al., Molecular Cloning: A Laboratory Manual (2 ed.), Cold Spring Harbor Laboratory Press, Cold Spring Harbor, N.Y., USA (1989)) or synthesized. Candidate compounds and agents can be screened for their ability treat a lung disease and/or alter iAEC2 phenotypes as described herein. In one embodiment, candidate agents are screened using the assays described above herein.

As used herein, the terms "compound" or "agent" are used interchangeably and refer to molecules and/or compositions including, but not limited to chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

Compounds can be tested at any concentration that can modulate expression or protein activity relative to a control over an appropriate time period. In some embodiments of any of the aspects, compounds are tested at concentrations in the range of about 0.1 nM to about 1000 mM. In one embodiment, the compound is tested in the range of about 0.1 µM to about 20 µM, about 0.1 µM to about 10 µM, or about 0.1 µM to about 5 µM. In one embodiment, compounds are tested at 1 µM. Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a lung disease. A subject can be male or female.

A subject can be one who has been previously diagnosed with or identified as suffering from or having a condition in need of treatment (e.g. a lung disease) or one or more complications related to such a condition, and optionally, have already undergone treatment for a lung disease or the one or more complications related to a lung disease. Alternatively, a subject can also be one who has not been previously diagnosed as having a lung disease or one or more complications related to a lung disease. For example, a subject can be one who exhibits one or more risk factors for a lung disease or one or more complications related to a lung disease or a subject who does not exhibit risk factors.

A "subject in need" of treatment for a particular condition can be a subject having that condition, diagnosed as having that condition, or at risk of developing that condition.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, Axin2, e.g. its ability to decrease the level and/or activity of Axin2, can be determined, e.g. by measuring the level of an expression product of Axin2 and/or the activity of Axin2. In some embodiments of any of the aspects, the inhibitor can be an inhibitory nucleic acid; an aptamer; an antibody reagent; an antibody; or a small molecule.

As used herein an "antibody" refers to IgG, IgM, IgA, IgD or IgE molecules or antigen-specific antibody fragments thereof (including, but not limited to, a Fab, F(ab')2, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to Axin2.

Inhibitors of the expression of a given gene can be an inhibitory nucleic acid. In some embodiments of any of the aspects, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an IRNA as described herein effects inhibition of the expression and/or activity of a target, e.g. Axin2. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments of any of the aspects, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Representative U.S. patents that teach the preparation of the above oligonucleosides include, but are not limited to, U.S. Pat. Nos. 5,034,506; 5,166,315; 5,185,444; 5,214,134; 5,216, 141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677, 439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —CH2-NH—CH2-, —CH2-N(CH3)-O—CH2- [known as a methylene (methylimino) or MMI backbone], —CH2-O—N (CH3)-CH2-, —CH2-N(CH3)-N(CH3)-CH2- and —N(CH3)-CH2-CH2- [wherein the native phosphodiester backbone is represented as —O—P—O—CH2-] of the above-referenced U.S. Pat. No. 5,489,677, and the amide backbones of the above-referenced U.S. Pat. No. 5,602,240. In some embodiments of any of the aspects, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2).nOCH3, O(CH2) nNH2, O(CH2) nCH3, O(CH2)nONH2, and O(CH2)nON [(CH2)nCH3)]2, where n and m are from 1 to about 10. In other embodiments, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an IRNA, and other substituents having similar properties. In some embodiments of any of the aspects, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

The term "aptamer" refers to a nucleic acid molecule that is capable of binding to a target molecule, such as a polypeptide. For example, an aptamer of the invention can specifically bind to a target molecule, or to a molecule in a signaling pathway that modulates the expression and/or activity of a target molecule. The generation and therapeutic use of aptamers are well established in the art. See, e.g., U.S. Pat. No. 5,475,096.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. agonist or inhibitor activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gin (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, (2) neutral hydrophilic: Cys, Ser, Thr, Asn, Gin; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments of any of the aspects, a polypeptide can be delivered and/or introduced into a cell (e.g., a means of contacting the cell with the polypeptide) by contacting the cell with a nucleic acid encoding the polypeptide, e.g., with a vector comprising a nucleic acid sequence encoding the polypeptide.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, a nucleic acid encoding a polypeptide as described herein is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. a lung disease. The term "treating" includes reducing or alleviating at least one adverse effect or symptom of a condition, disease or disorder associated with a lung disease. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "type II alveolar epithelial cell" refers to an epithelial cell found in the alveoli which produce pulmonary surfactant AEC2s are characterized by high expression of, e.g., SFTPC, SFTPB, and ABCA3. Mutations affecting genes highly expressed in AEC2s, such as SFTPC, SFTPB, and ABCA3, cause children's interstitial lung disease (chILD), which can result in neonatal respiratory distress or early-onset pulmonary fibrosis (reviewed in Whitsett et al. 2015). Mutations in genes that affect AEC2s have also been implicated in both familial adult-onset pulmonary fibrosis (Lawson et al. 2005); (van Moorsel et al. 2010); (Mulugeta et al. 2015) as well as in some sporadic variants (Brasch, et al. 2004).

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments of any of the aspects, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of making induced alveolar epithelial type 2 cells (iAEC2s), the method comprising:
    contacting a NKX2-1+ lung epithelial progenitor cell with:
        an agonist of Wnt/beta-catenin signaling;
        a corticosteroid; and
        an agonist of cyclicAMP or the cyclicAMP pathway.
2. The method of paragraph 1, wherein the contacting step is continued for at least 3 days.
3. The method of paragraph 1, wherein the contacting step is continued for at least 15 days.
4. The method of any of paragraphs 1-3, further comprising a culturing step after the contacting step, wherein the cells are cultured without being contacted with an agonist of Wnt/beta-catenin signaling.
5. The method of paragraph 4, wherein the culturing step is continued for at least 5 days.
6. The method of paragraph 4, wherein the culturing step is continued for at least 10 days.
7. A method of making iAEC2s, the method comprising:
    a first culturing step of culturing a population of NKX2-1+ lung epithelial progenitor cells in the presence of:
        an agonist of Wnt/beta-catenin signaling;
        a corticosteroid; and
        an agonist of cyclicAMP or the cyclicAMP pathway;
    for a period of about 2 weeks;
    a second culturing step of culturing the cells resulting from the first culturing step in the presence of
        a corticosteroid and an agonist of cyclicAMP or the cyclic AMP pathways but not an agonist of Wnt/beta-catenin signaling;
    for a period of about 1 week; and
    a third culturing step of culturing the cells resulting from the second culturing step in the presence of:
        an agonist of Wnt/beta-catenin signaling;
        a corticosteroid; and
        an agonist of cyclicAMP or the cyclicAMP pathway
    for a period of about 1 week.
8. The method of any of paragraphs 1-7, wherein the agonist of Wnt/beta catenin signaling is selected from the group consisting of:
    CHIR99021; a recombinant Wnt polypeptide; a Wnt polypeptide; an exogenous Wnt polypeptide; BIO; WAY-316606; a (hetero) arylpyrimidine; IQ1; QS11; SB-216763; DCA; R-spondin; and an inhibitor of Axin2 and/or APC.
9. The method of any of paragraphs 1-8, wherein the corticosteroid is selected from the group consisting of:
    dexamethasone; hydrocortisone; cortisone; prednisone; prednisolone; methylprednisolone; triamncinolone; betamethasone; fludrocortisone acetate; and deoxycorticosterone acetate.
10. The method of any of paragraphs 1-9, wherein the agonist of cyclicAMP or the cyclicAMP pathway is selected from the group consisting of:
    cyclicAMP; IBMX, cholera toxin, forskolin, caffeine, theophylline, bucaldesine, and pertussis toxin.
11. The method of any of paragraphs 1-10, wherein the NKX2-1+ lung epithelial progenitor cell is further contacted or cultured with an agonist of FGF signaling.
12. The method of paragraph 11, wherein the agonist of FGF signaling is a polypeptide selected from the group consisting of:
    KGF; a FGF receptor ligand; FGF1; FGF2; FGF3; FGF4; FGF6; FGF8; FGF9; FGF10; FGF17; FGF18; FGF22; and a small molecule agonist of FGF signaling.

13. The method of paragraph 11, wherein the agonist of FGF signaling is KGF polypeptide.
14. The method of any of paragraphs 1-13, wherein the culturing or contacting step comprising a corticosteroid and an agonist of cyclicAMP or the cyclicAMP pathway further comprises culturing or contacting the cell with 3-isobutyl-1-methylxanthine (IMBX).
15. The method of any of paragraphs 1-14, wherein the NKX2-1+ lung epithelial progenitor cell is not contacted or cultured with a mesenchymal cell.
16. The method of any of paragraphs 1-15, wherein the NKX2-1+ lung epithelial progenitor cell is a CD47hi/CD2610 cell.
17. The method of any of paragraphs 1-16, wherein the NKX2-1+ lung epithelial progenitor cell is provided by sorting lung epithelial progenitor cells to isolate a CD47hi/CD2610 population.
18. The method of any of paragraphs 1-17, wherein the NKX2-1+ lung epithelial progenitor cell is derived from an induced pluripotent stem cell (iPSC).
19. The method of any of paragraphs 1-18, wherein the NKX2-1+ lung epithelial progenitor cell is derived from a cell obtained from a subject.
20. The method of any of paragraphs 1-19, further comprising first genetically modifying the NKX2-1+ lung epithelial progenitor cell or the less differentiated cell the NKX2-1+ lung epithelial progenitor cell is derived from.
21. The method of any of paragraphs 1-20, wherein the NKX2-1+ lung epithelial progenitor cell is derived from an less differentiated cell by contacting the less differentiated cell with CHIR, BMP4, and RA.
22. The method of any of paragraphs 1-21, wherein the iAEC2 cell is a NKX2-1+/SFTPC+ cell.
23. An iAEC2 cell produced according to the method of any of paragraphs 1-22.
24. A method of treating a lung disease in a subject in need thereof, the method comprising administering to the subject an iAEC2 cell produced according to the method of any of paragraphs 1-20.
25. The method of paragraph 24, wherein the lung disease is selected from the group consisting of:
a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and emphysema.
26. The method of any of paragraphs 24-25, wherein the iAEC2 cell is derived from a cell obtained from the subject.
27. The method of any of paragraphs 24-26, wherein the NKX2-1+ lung epithelial progenitor cell or the less differentiated cell the NKX2-1+ lung epithelial progenitor cell is derived from was genetically modified to correct a mutation that contributed to the lung disease.
28. A method of identifying a treatment as effective in treating lung disease, the method comprising:
contacting an iAEC2 produced according to the method of any of paragraphs 1-22 with a candidate treatment agent;
identifying the candidate treatment agent as effective if one or more of the following phenotypes is observed in the iAEC2 contacted with the candidate treatment agent as compared to an iAEC2 not contacted with the candidate treatment agent:
i) increased cell survival;
ii) increased cell survival in the presence of cellular stressors;
iii) decreased release of toxic agents;
iv) improved cellular pathology arising from a genetic mutation in the iAEC2;
v) increased iAEC2 differentiation;
vi) decreased iAEC2 proliferation in the presence of carcinogens; and/or
vii) increased secretion of cytoprotective agents.
29. The method of paragraph 28, wherein the iAEC2 is derived from a cell obtained from an individual subject and the treatment is identified as an effective treatment for that individual subject.
30. A iAEC2 cell produced according to the method of any of paragraphs 1-20, for administration to the subject in need of treatment for a lung disease.
31. The cell of paragraph 30, wherein the lung disease is selected from the group consisting of:
a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and emphysema.
32. The cell of any of paragraphs 30-31, wherein the iAEC2 cell is derived from a cell obtained from the subject.
33. The cell of any of paragraphs 30-32, wherein the NKX2-1+ lung epithelial progenitor cell or the less differentiated cell the NKX2-1+ lung epithelial progenitor cell is derived from was genetically modified to correct a mutation that contributed to the lung disease.

Some embodiments of the technology described herein can be defined according to any of the following numbered paragraphs:

1. A method of making induced alveolar epithelial type 2 cells (iAEC2s), the method comprising:
contacting a NKX2-1+ lung epithelial progenitor cell with:
an agonist of Wnt/beta-catenin signaling;
a corticosteroid; and
an agonist of cyclicAMP or the cyclicAMP pathway.
2. The method of paragraph 1, wherein the contacting step is continued for at least 3 days.
3. The method of paragraph 1, wherein the contacting step is continued for at least 15 days.
4. The method of any of paragraphs 1-3, further comprising a culturing step after the contacting step, wherein the cells are cultured without being contacted with an agonist of Wnt/beta-catenin signaling.
5. The method of paragraph 4, wherein the culturing step is continued for at least 5 days.
6. The method of paragraph 4, wherein the culturing step is continued for at least 10 days.
7. A method of making iAEC2s, the method comprising:
a first culturing step of culturing a population of NKX2-1+ lung epithelial progenitor cells in the presence of:
an agonist of Wnt/beta-catenin signaling;
a corticosteroid; and
an agonist of cyclicAMP or the cyclicAMP pathway;
for a period of about 2 weeks;
a second culturing step of culturing the cells resulting from the first culturing step in the presence of
a corticosteroid and an agonist of cyclicAMP or the cyclic AMP pathways but not an agonist of Wnt/beta-catenin signaling;

for a period of about 1 week; and
a third culturing step of culturing the cells resulting from the second culturing step in the presence of:
an agonist of Wnt/beta-catenin signaling;
a corticosteroid; and
an agonist of cyclicAMP or the cyclicAMP pathway
for a period of about 1 week.

8. The method of any of paragraphs 1-7, wherein the agonist of Wnt/beta catenin signaling is selected from the group consisting of:
CHIR99021; a recombinant Wnt polypeptide; a Wnt polypeptide; an exogenous Wnt polypeptide; B10; WAY-316606; a (hetero) arylpyrimidine; IQ1; QS11; SB-216763; DCA; R-spondin; and an inhibitor of Axing and/or APC.

9. The method of any of paragraphs 1-8, wherein the corticosteroid is selected from the group consisting of:
dexamethasone; hydrocortisone; cortisone; prednisone; prednisolone; methylprednisolone; triamncinolone; betamethasone; fludrocortisone acetate; and deoxycorticosterone acetate.

10. The method of any of paragraphs 1-9, wherein the agonist of cyclicAMP or the cyclicAMP pathway is selected from the group consisting of:
cyclicAMP; IBMX, cholera toxin, forskolin, caffeine, theophylline, bucaldesine, and pertussis toxin.

11. The method of any of paragraphs 1-10, wherein the NKX2-1+ lung epithelial progenitor cell is further contacted or cultured with an agonist of FGF signaling.

12. The method of paragraph 11, wherein the agonist of FGF signaling is a polypeptide selected from the group consisting of:
KGF; a FGF receptor ligand; FGF1; FGF2; FGF3; FGF4; FGF6; FGF8; FGF9; FGF10; FGF17; FGF18; FGF22; and a small molecule agonist of FGF signaling.

13. The method of paragraph 11, wherein the agonist of FGF signaling is KGF polypeptide.

14. The method of any of paragraphs 1-13, wherein the culturing or contacting step comprising a corticosteroid and an agonist of cyclicAMP or the cyclicAMP pathway further comprises culturing or contacting the cell with 3-isobutyl-1-methylxanthine (IMBX).

15. The method of any of paragraphs 1-14, wherein the NKX2-1+ lung epithelial progenitor cell is not contacted or cultured with a mesenchymal cell.

16. The method of any of paragraphs 1-15, wherein the NKX2-1+ lung epithelial progenitor cell is a CD47hi/CD26lo cell.

17. The method of any of paragraphs 1-16, wherein the NKX2-1+ lung epithelial progenitor cell is provided by sorting lung epithelial progenitor cells to isolate a CD47hi/CD26lo population.

18. The method of any of paragraphs 1-17, wherein the NKX2-1+ lung epithelial progenitor cell is derived from an induced pluripotent stem cell (iPSC).

19. The method of any of paragraphs 1-18, wherein the NKX2-1+ lung epithelial progenitor cell is derived from a cell obtained from a subject.

20. The method of any of paragraphs 1-19, further comprising first genetically modifying the NKX2-1+ lung epithelial progenitor cell or the less differentiated cell the NKX2-1+ lung epithelial progenitor cell is derived from.

21. The method of any of paragraphs 1-20, wherein the NKX2-1+ lung epithelial progenitor cell is derived from a less differentiated cell by contacting the less differentiated cell with CHIR, BMP4, and RA.

22. The method of any of paragraphs 1-21, wherein the iAEC2 cell is a NKX2-1+/SFTPC+ cell.

23. The method of any of paragraphs 1-22, wherein the iAEC2 cell is karyotypically normal.

24. An iAEC2 cell produced according to the method of any of paragraphs 1-23.

25. A method of treating a lung disease in a subject in need thereof, the method comprising administering to the subject an iAEC2 cell produced according to the method of any of paragraphs 1-23.

26. The method of paragraph 25, wherein the lung disease is selected from the group consisting of:
a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and emphysema.

27. The method of any of paragraphs 25-26, wherein the iAEC2 cell is derived from a cell obtained from the subject.

28. The method of any of paragraphs 25-27, wherein the NKX2-1+ lung epithelial progenitor cell or the less differentiated cell the NKX2-1+ lung epithelial progenitor cell is derived from was genetically modified to correct a mutation that contributed to the lung disease.

29. A method of identifying a treatment as effective in treating lung disease, the method comprising:
contacting an iAEC2 produced according to the method of any of paragraphs 1-23 with a candidate treatment agent;
identifying the candidate treatment agent as effective if one or more of the following phenotypes is observed in the iAEC2 contacted with the candidate treatment agent as compared to an iAEC2 not contacted with the candidate treatment agent:
i) increased cell survival;
ii) increased cell survival in the presence of cellular stressors;
iii) decreased release of toxic agents;
iv) improved cellular pathology arising from a genetic mutation in the iAEC2;
v) increased iAEC2 differentiation;
vi) decreased iAEC2 proliferation in the presence of carcinogens; and/or
vii) increased secretion of cytoprotective agents.

30. The method of paragraph 29, wherein the iAEC2 is derived from a cell obtained from an individual subject and the treatment is identified as an effective treatment for that individual subject.

31. A iAEC2 cell produced according to the method of any of paragraphs 1-22, for administration to the subject in need of treatment for a lung disease.

32. The cell of paragraph 31, wherein the lung disease is selected from the group consisting of:
a surfactant deficiency; pulmonary fibrosis; interstitial lung disease (ILD); cystic fibrosis; alpha-1 antitrypsin deficiency; lung adenocarcinoma; pulmonary hypertension; cystic lung disease; chronic obstructive pulmonary disease; and emphysema.

33. The cell of any of paragraphs 31-32, wherein the iAEC2 cell is derived from a cell obtained from the subject.

34. The cell of any of paragraphs 31-33, wherein the NKX2-1+ lung epithelial progenitor cell or the less differentiated cell the NKX2-1+ lung epithelial progenitor cell is derived from was genetically modified to correct a mutation that contributed to the lung disease.

EXAMPLES

Example 1

Described herein are methods by which mature pulmonary alveolospheres can be derived from human pluripotent stem cells. These alveolospheres exhibit the full surfactant processing capabilities of naturally-occurring type II alveolar epithelial cells. The methods described herein permit the generation of inexhaustable supplies of alveolar cell types from patients with clinical alveolar disease, such as surfactant deficiency or pulmonary fibrosis, for use in disease modeling, drug screening, and cell-based therapy.

Described herein is a methodology for generating lung alveolar epithelial type II cells in the laboratory from human pluripotent stem cells (such as patient specific induced pluripotent stem cells; iPSCs). These methods permit drug development and cell therapy approaches by producing clinically relevant alveolar cells from stem cells. The generation of these stem cells is especially relevant in diseases of currently unknown etiology such as interstitial lung disease.

Briefly, the methods herein relate to a combination of FGF signaling, WNT signaling activator modulation, and steroid treatment to generate alveolar spheroids with a lineage specific reporter that can be used to model genetic lung disease. Demonstrated herein is the ability to drive purified lung progenitors to purified alveolar epithelial cell types using a lineage specific reporter. These cells have been characterized to an extent not previously reported and were shown to be functionally mature. The presently disclosed methods generate alveolar cells at an efficiency of 40-70%, which has never been reported by any other group. Alveolospheres produced according to the methods described herein were used in the first reporter iPSC based model of genetic alveolar disease, indicating their utility to the field.

It is contemplated that various sorting strategies, two- and three-dimensional replating conditions, manipulations to the base media ("cSFDM"), the use of different FGFs, EGFs, WNT agonists, or any other signaling pathway agonists or antagonists, omission of the FGF factors entirely, the withdrawal of cyclic AMP and/or IBMX, or changing the steroids used in the media can be applied to the methods described herein.

Example 2: Generation of Mature Lung Alveolar Epithelial Cells from Human Pluripotent Stem Cells Tissues arising late in evolutionary time, such as lung alveoli that are unique to air breathing organisms, have been challenging to generate in vitro from pluripotent stem cells (PSCs), in part because there are limited lower organism model systems available to provide the necessary developmental roadmaps to guide in vitro differentiation. Described herein is the successful directed differentiation in vitro of human PSCs into alveolar epithelial type 2 cells (AEC2s), the facultative progenitors of lung alveoli. Using gene editing to engineer multicolored fluorescent reporter PSC lines ($NKX2-1^{GFP}$; $SFTPC^{tdTomato}$)human SFTPC+ alveolar progenitors were tracked and purified as they emerge from NKX2-1+ endodermal developmental precursors in response to stimulation of Wnt and FGF signaling. Purified PSC-derived SFTPC+ cells are able to form monolayered epithelial spheres ("alveolospheres") in 3D cultures without the need for mesenchymal co-culture support, exhibit extensive self-renewal capacity, and display additional canonical AEC2 functional capacities, including innate immune responsiveness, the production of lamellar bodies able to package surfactant, and the ability to undergo squamous cell differentiation while upregulating type 1 alveolar cell markers. Guided by time-series global transcriptomic profiling it was found that AEC2 maturation involves downregulation of Wnt signaling activity, and the highest differentially expressed transcripts in the resulting SFTPC+ cells encode genes associated with lamellar body and surfactant biogenesis. Finally, this novel model system was used to generate patient-specific AEC2s from induced PSCs (iPSCs) carrying homozygous surfactant mutations ($SFTPB^{121in2}$), and footprint-free CRISPR-based gene editing was employed to observe that correction of this genetic lesion restores surfactant processing in the cells responsible for their disease. Thus, described herein is an approach for disease modeling and functional regeneration of a cell type unique to airbreathing organisms.

Pulmonary alveolar epithelial type II cell (AEC2) dysfunction has been implicated as a primary cause of pathogenesis in many poorly understood lung diseases that lack effective therapies, including interstitial lung disease (ILD) and emphysema. In particular, studies have shown that mutations affecting genes highly expressed in AEC2s, such as SFTPC, SFTPB, and ABCA3, cause children's interstitial lung disease (chILD), which can result in neonatal respiratory distress or early-onset pulmonary fibrosis (reviewed in Whitsett et al. 2015). Mutations in genes that affect AEC2s have also been implicated in both familial adult-onset pulmonary fibrosis (Lawson et al. 2005); (van Moorsel et al. 2010); (Mulugeta et al. 2015) as well as in some sporadic variants (Brasch, et al. 2004). Hence, studying AEC2s from patients with these mutations might provide insight into the mechanisms by which early AEC2 dysfunction can lead to a wide variety of lung diseases.

Despite the broadly acknowledged need for human AEC2 in primary cell culture, a pure source of expandable AEC2s has not been previously achieved. Reports have shown that AEC2s proliferate poorly ex-vivo and transdifferentiate into type I alveolar epithelial cells (AEC I s) when isolated from human lungs and cultured (Foster et al. 2007); (Borok et al. 1998). Methods that do show maintenance of the AEC2 phenotype in culture require addition of mesenchymal feeders (Barkauskas et al. 2013), complicating the study of AEC2-specific biology in vitro. Since AEC2s are also relatively inaccessible to study in the developing human embryo, it is difficult to correlate findings in mice with human lung development. These obstacles to AEC2 study have limited research in alveolar development and disease, and have prevented the engineering of approaches to correct the genetic lesions that cause AEC2-initiated lung diseases.

Using induced pluripotent stem cell (iPSC) technology and directed differentiation to generate AEC2s de novo would provide novel opportunities to study normal human AEC2 development and to understand the pathogenesis of monogenic alveolar diseases. Current technologies do not permit analysis of pure populations of iPSC-derived putative AEC2s (iAEC2s) in comparison to primary controls, assessment of the maturation state of iAEC2s relative to the developing human lung, and evaluation of the ability of iAEC2s to model human alveolar disease in vitro.

AEC2s have several critical roles in the distal lung. First, they are the facultative progenitors of the alveolus (Barkauskas et al. 2013); (Mason & Williams 1977); (Desai et. al., 2014), responding to lung parenchymal injury in mice by self-renewing or differentiating into AEC1s. AEC2s also function to synthesize and secrete surfactant, modulating alveolar surface tension (Kikkawa et al. 1975), and are able to respond to innate immune stimuli, protecting against infection (Juers et al. 1976); (O'Brien et al. 1998). Several surfactant proteins are expressed in AEC2s, but only one, surfactant protein C (SFTPC), is reported to be highly specific to the AEC2 in humans (Kalina et al. 1992); (Wohlford-Lenane et al. 1992). Even then, though SFTPC may be specific to the AEC2s in adults, it is expressed as early as week 12-15 in human development (Otto-Verberne et al. 1988); (Khoor et al. 1994) and E10.5 in mouse development in the distal lung bud (Wert et al. 1993). Mature AEC2s are characterized not only by expression of SFTPC, but also by the ability to assemble functional lamellar bodies (Mason & Williams 1977); (Sorokin 1966), the organelle in which surfactant proteins and phospholipids are processed, stored, and secreted, a benchmark that has not yet been evaluated in iPSC-derived lung epithelial cells.

Described herein is the engineering of human pluripotent stem cell (PSC) lines with fluorescent reporters (GFP and/or tdTomato) targeted to the endogenous NKX2-1 and SFTPC loci, respectively. These tools are employed to quantify the efficiency of alveolar directed differentiation in response to various inductive signals and isolate putative SFTPC+ alveolar cells for transcriptomic analysis compared to primary controls. Differentiating NKX2-1+ lung epithelial progenitor cells without mesenchymal co-culture in media containing activators of Wnt and FGF signaling promotes differentiation of epithelial spheres containing SFTPC+ cells ("alveolospheres"). These alveolospheres display canonical AEC2 functional capacities, including innate immune responsiveness and the production of lamellar bodies able to package surfactant. Guided by time-series global transcriptomic profiling of PSC-derivatives, it was found that AEC2 maturation involves downregulation of Wnt signaling activity and that the highest differentially expressed transcripts in iPSC-derived AEC2s encode genes associated with lamellar body and surfactant biogenesis.

Finally, iPSCs were generated from a patient with an SFTPB mutation known to cause children's interstitial lung disease (chILD). The mutation was using CRISPR-Cas9 technology and the pre- and post-corrected iPSCs were differentiated into alveolospheres. Pre-corrected iPSC-derived alveolospheres recapitulate key pathological features of SFTPB deficiency, while post-correction, these alveolospheres display reconstitution of surfactant processing. This human model system can therefore facilitate disease modeling, developmental studies, drug screening, and regenerative gene or cell therapies for a variety of adult and childhood lung diseases affecting lung alveoli.

Results

Figure 8A:
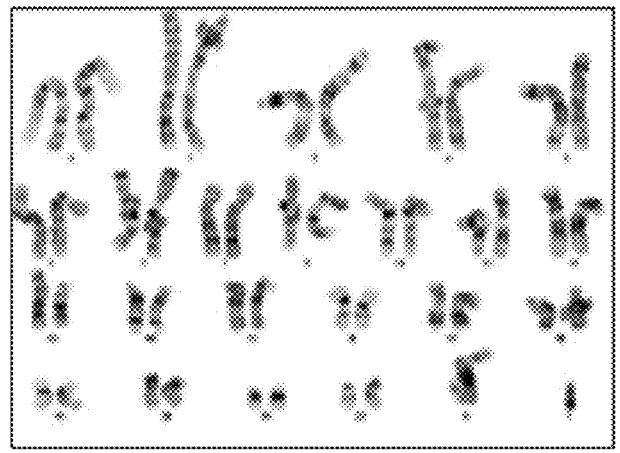
FIGS. 8A-8D demonstrate targeting and validation of NKX2-1GFP and SFTPCtdTomato reporter lines.
Figure 8A:
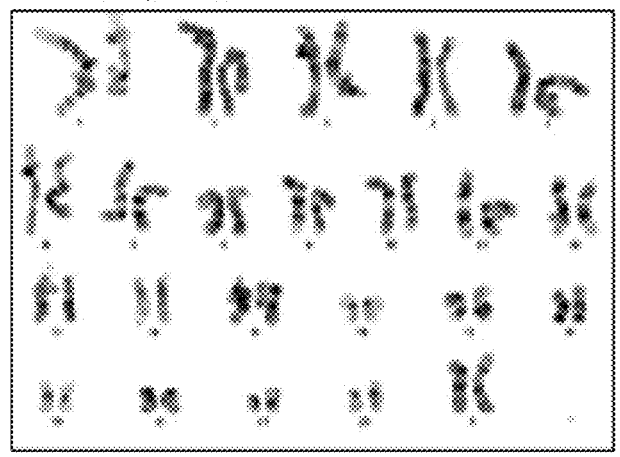
Figure 8A:
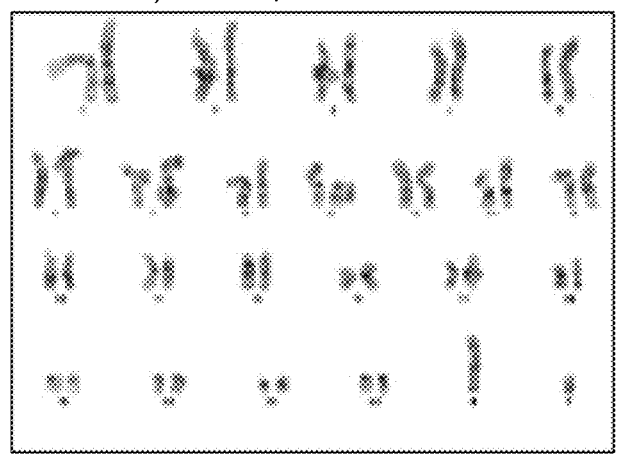
Figure 8B:
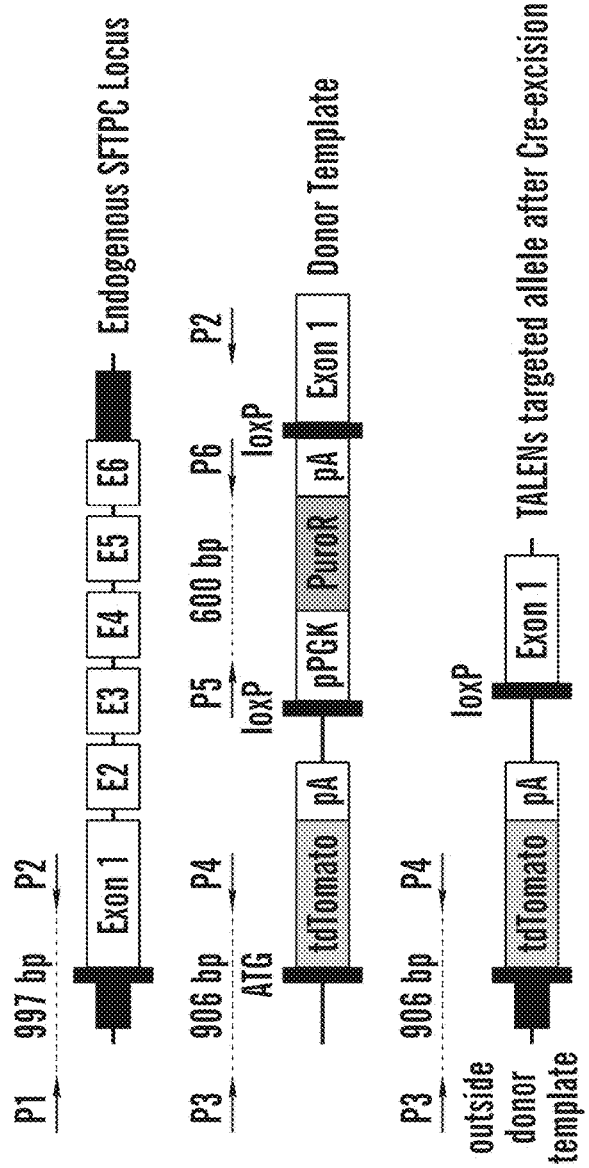
Figure 8B:
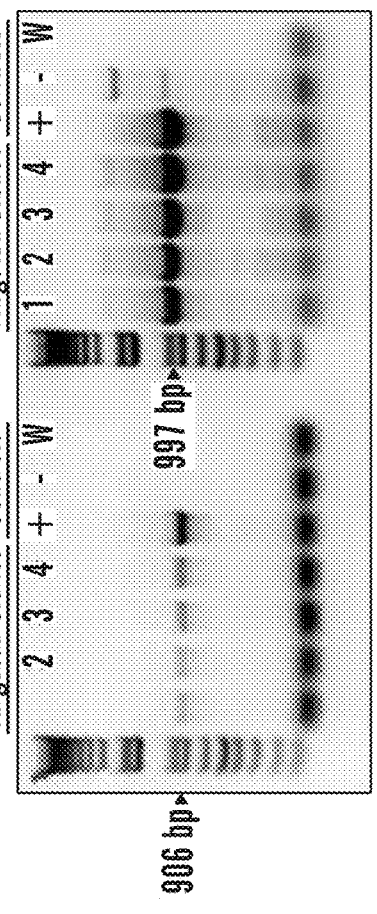
Figure 8C:
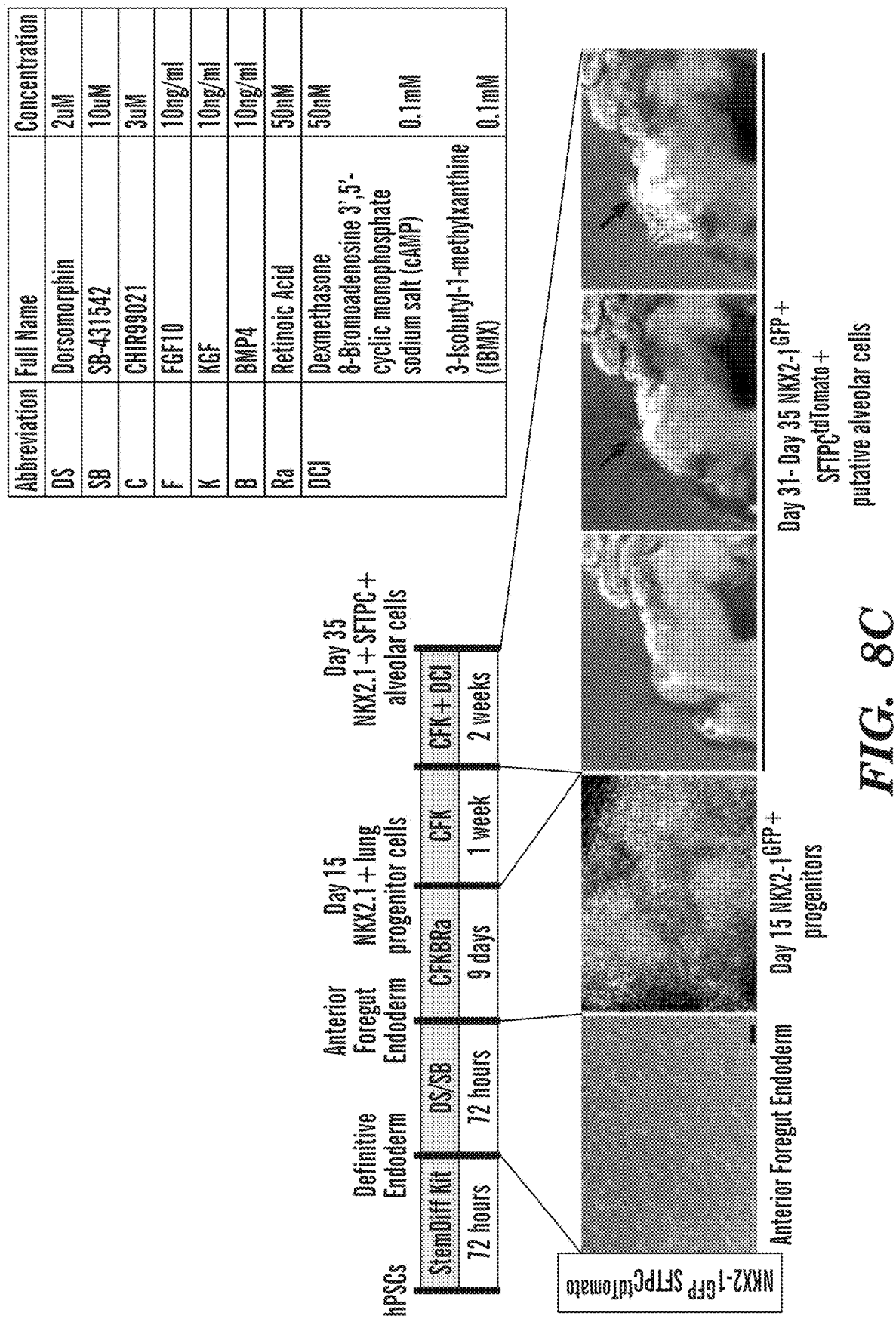
Figure 8D:
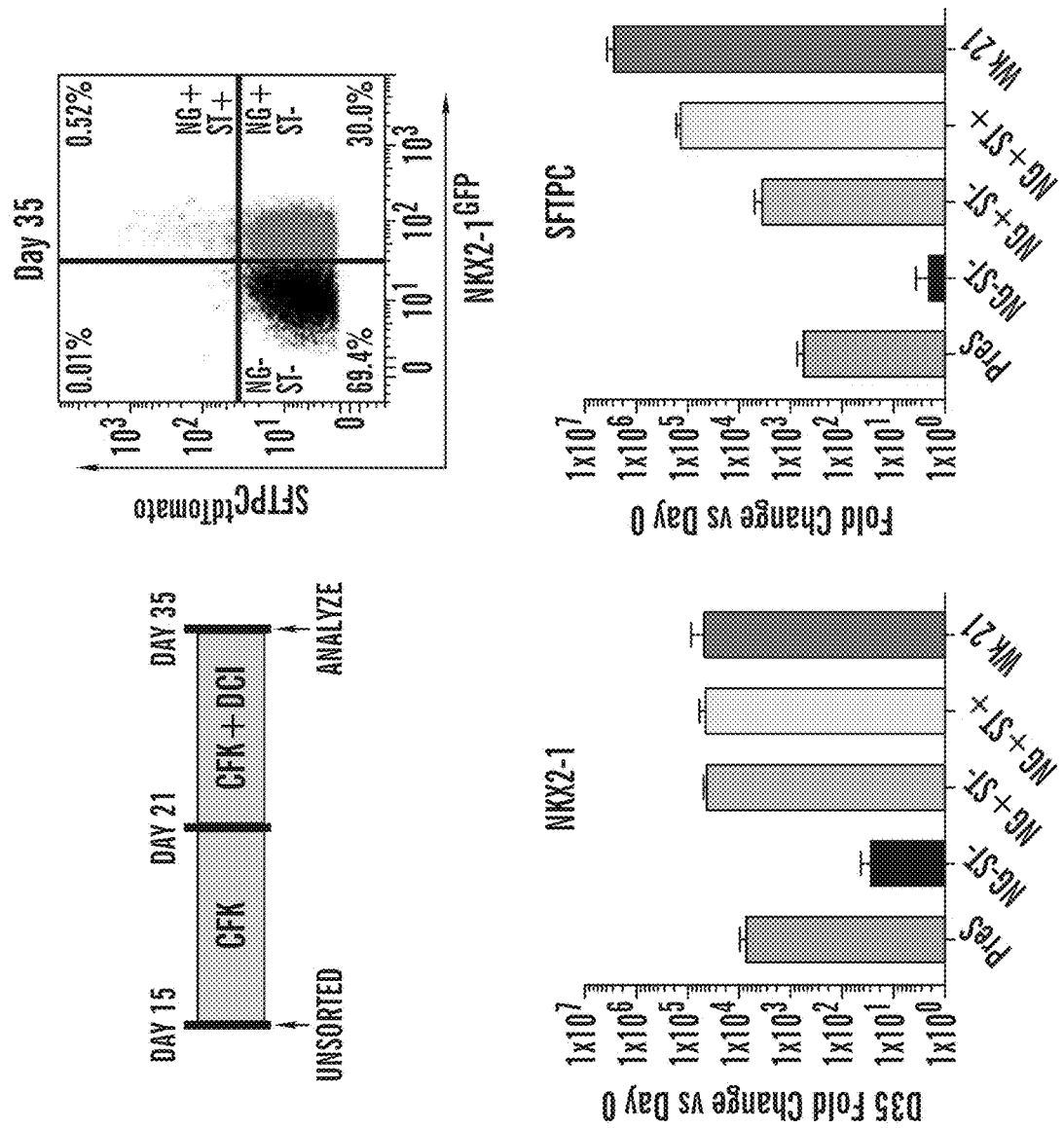

SFTPC reporter PSC lines allow visualization of distal lung differentiation and isolation of putative iAEC2s. During mouse lung development, AEC2s derive from SFTPC+ distal lung bud progenitors, which in turn arise from less differentiated NKX2-1+ foregut endoderm-derived lung epithelial precursors that do not yet express SFTPC. To observe in real-time this putative sequence of AEC2 development in human cells, gene editing was first used to target fluorochrome reporter constructs (GFP and tdTomato) to the endogenous NKX2-1 and SFTPC loci, respectively (FIGS. 1A, 8A, 8B). Using a published lung directed differentiation protocol (FIG. 8C) established by Snoeck and colleagues (Huang et al. 2013), sequential in vitro differentiation of dual-targeted iPSC lines (C17 and BU3) into uncolored foregut endoderm followed by NKX2-1GFP+/SFTPCtdTomato− putative primordial lung progenitors, and then NKX2-1GFP+/SFTPCtdTomato+ cells was observed (FIG. 8C). NKX2-1 is an essential transcription factor known to bind the SFTPC promoter, is required for SFTPC gene expression, and is expressed in all developing lung epithelia in vivo, including fetal and adult AEC2s (Minoo 1999); (Boggaram 2009). In keeping with these in vivo observations, all PSC-derived SFTPCtdTomato+ cells co-expressed the NKX2-1GFP reporter (FIG. 8D). Flow cytometry sorting of NKX2-1GFP+/SFTPCtdTomato+ cells enriched for expression of both NKX2-1 and SFTPC transcripts (FIG. 8D), however, both the efficiency of differentiation and SFTPC expression levels within the SFTPCtdTomato+ population when compared to primary fetal alveolar epithelial control cells were initially low. Similar findings were observed with this protocol in single color RUES2 SFTPCtdTomato+ cells (data not shown).

Figure 1B:
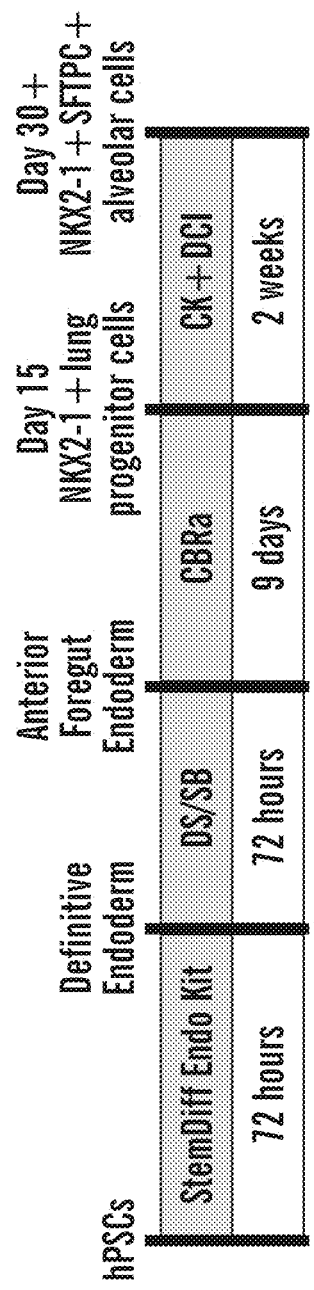
Figure 1C:
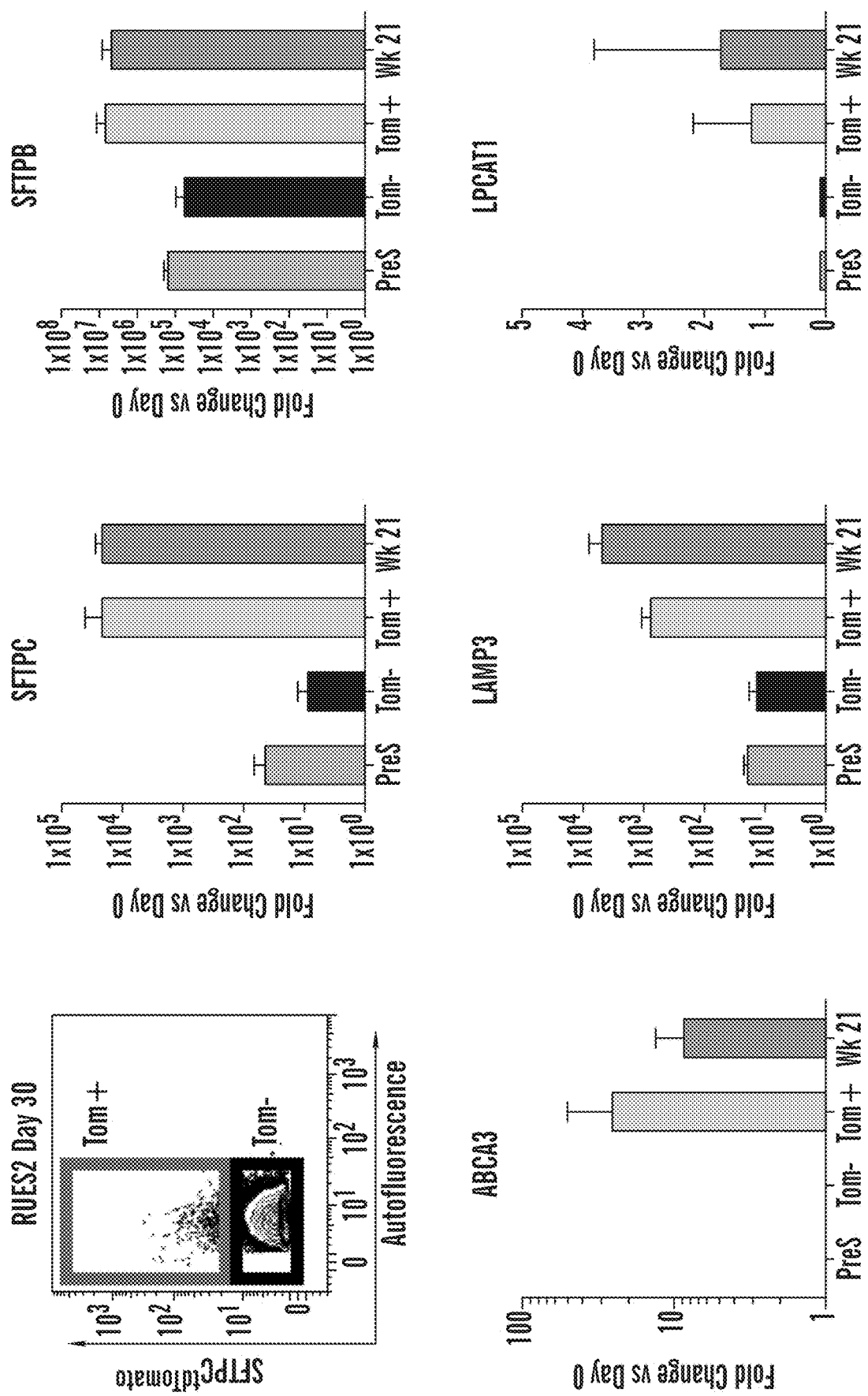
Figure 9A:
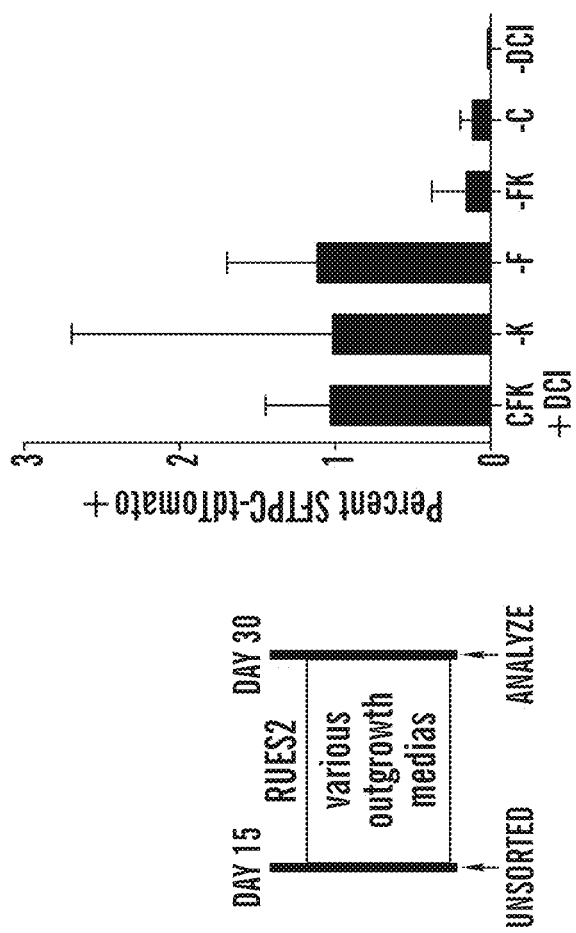
FIGS. 9A-9C demonstrate manipulation of signaling pathways and Day 15 surface marker-based sorting in iAEC generation.
Figure 9B:
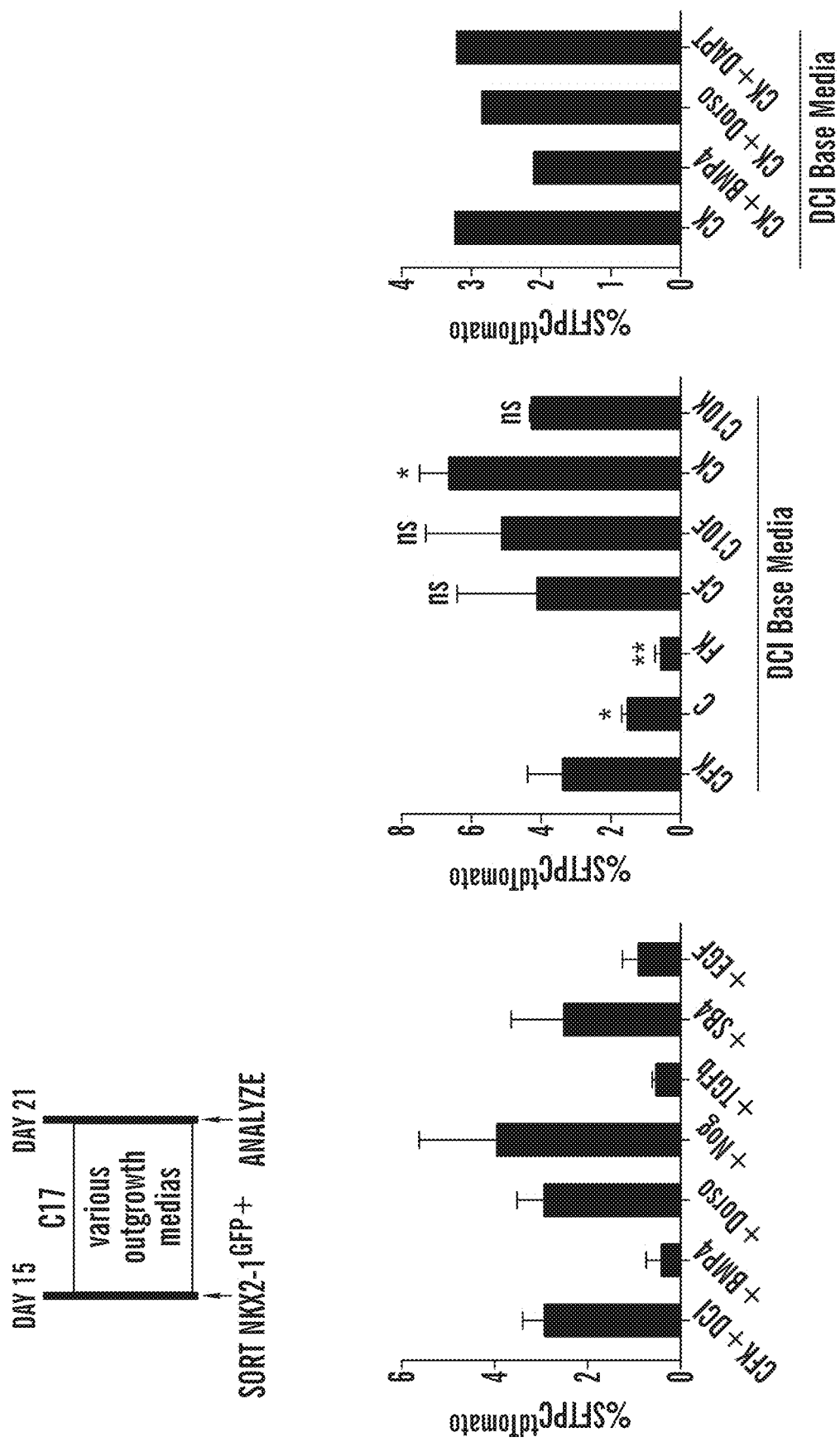

To optimize SFTPC differentiation efficiency we sequentially withdrew one factor at a time from each stage of differentiation (NKX2-1 progenitor induction stage vs SFTPC+ induction stage), observing that only three factors (CHIR, BMP4, and RA; hereafter CBRa) were sufficient for the specification of NKX2-1+ progenitors, as published previously (Gotoh et al., 2014); (Rankin et al. 2016). For subsequent SFTPC induction within this NKX2-1+ population, only two exogenous factors (CHIR and KGF; hereafter CK) were sufficient in the presence of previously published lung maturation additives (dexamethasone, cyclicAMP and IBMX; hereafter "DCI") (Gonzales et al. 2002) (FIGS. 9A, 9B). No consistent further SFTPC induction efficiency was found with the addition of other reported distalizing factors, such as BMP4, EGF, and FGF10 or with additional inhibitors of BMP, TGFβ, or Notch signaling (FIG. 9B and data not shown). Testing the optimized differentiation protocol (FIG. 1B) on our single-color RUES2 SFTPCtdTomato ESC line, efficient induction of endodermal NKX2-1 was observed with CBRa (50.67%+/−16.05) by day 15 and rapid emergence of SFTPCtdTomato+ cells within 3 to 7 days of subsequent exposure to CK+DCI (FIG. 1B, data not shown). tdTomato+ cells could be visualized scattered throughout epithelial spheres in 3D cultures of all targeted PSC lines (data not shown), and by day 30 of differentiation these tdTomato+ cells were highly enriched in transcripts encoding surfactant proteins as well as transcripts associated with lamellar body biogenesis, SFTPC, SFTPB, ABCA3, LAMP3, and LPCAT1 (FIG. 1C). Notably SFTPC, SFTPB, and ABCA3 were expressed at levels higher than primary fetal lung controls (week 21 gestation fetal alveolar epithelial cells ~85-90% SFPTC+). At the protein level, epithelial spheres that included tdTomato+ cells also expressed NKX2-1 nuclear protein, membranous EPCAM, punctate cytoplasmic ProSFTPC, and intracellular as well as secreted SFTPB protein (data not shown).

Figure 1D:
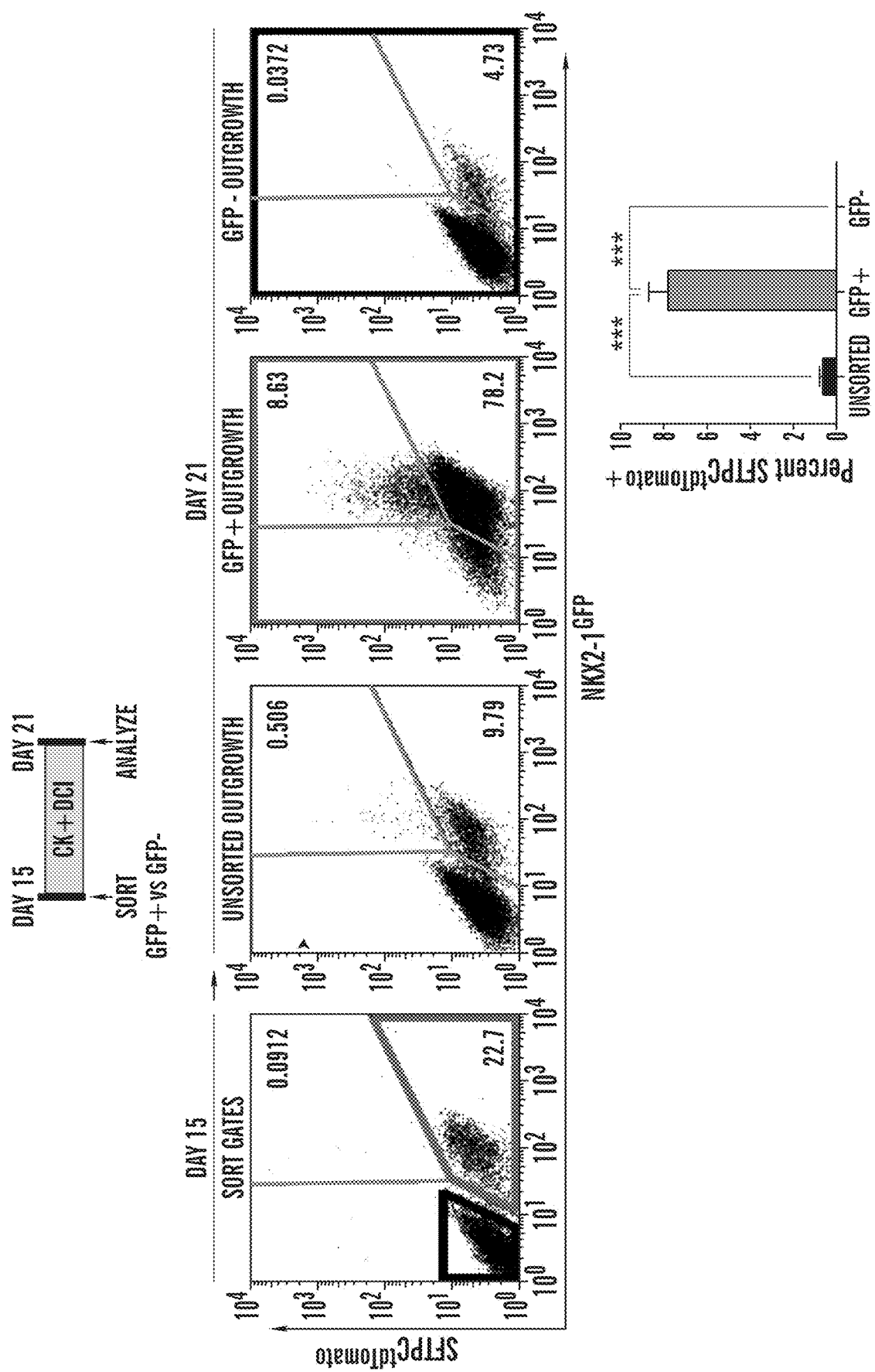
Figure 9C:
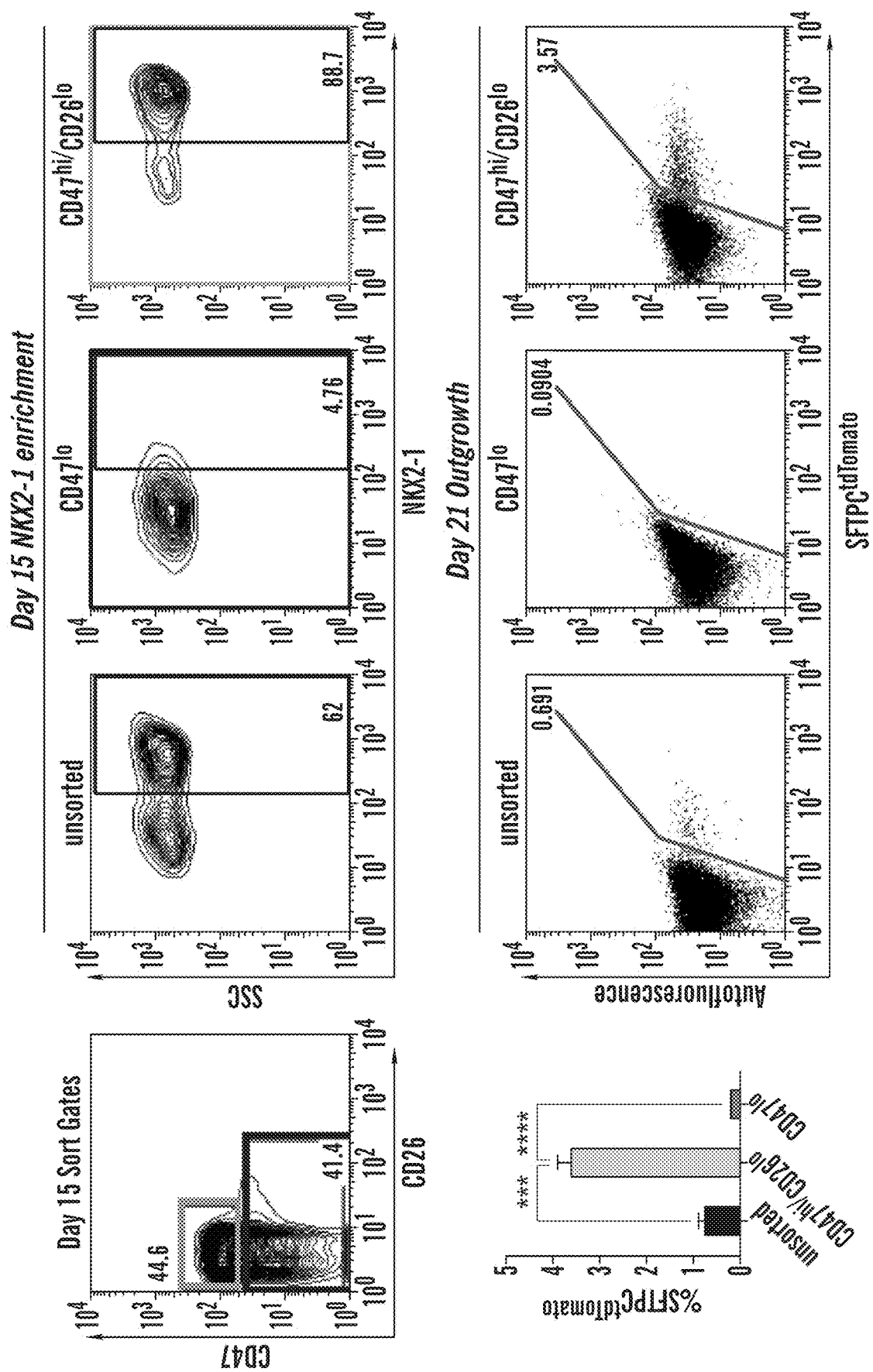

Human putative alveolar cells derive from an NKX2-1+ primordial progenitor. Next, it was asked whether the early NKX2-1+ population represented the entire pool of progenitors from which SFTPC+ alveolar cells might arise. To address this question, day 15 unsorted cells were differentiated and sorted NKX2-1GFP+vs NKX2-1GFP− cells in parallel (FIG. 1D). It was found that NKX2-1GFP+ sorted cells gave rise to SFTPC+ cells, whereas GFP− sorted cells were not competent to give rise to SFTPC+ progeny. The mixed (unsorted) population resulted in a lower efficiency of alveolar differentiation, indicating that the NKX2-1GFP− population does not detectably contain a lineage that promotes alveolar differentiation, such as lung-specific mesenchyme (FIG. 1D), findings consistent with previous profiling of the iPSC-derived GFP negative population (Hawkins et al,.). To extend this approach to PSCs that do not contain an NKX2-1 knock-in reporter, a strategy was developed to identify AEC2-competent NKX2-1+ progenitors in the RUES2 cell line, which has a single SFTPCtdTomato reporter. CD47hi/CD2610 day 15 cells are highly enriched in NKX2-1+ lung progenitors (Hawkins et al.,). In keeping with these findings, it was observed that sorting RUES2 Day 15 cells based on CD47hi/CD2610 gating (FIG. 9C) resulted in ~88% NKX2-1+ cells (compared to ~62% NKX2-1+ without sorting and ~5% in CD4710 cells), and that CD47hi/CD26lo sorting on day 15 identified the entirety of the SFTPC competent population, enriching the SFTPC+ yield in the day 21 population approximately 4 fold over unsorted cells (FIG. 9C).

Figure 2A:
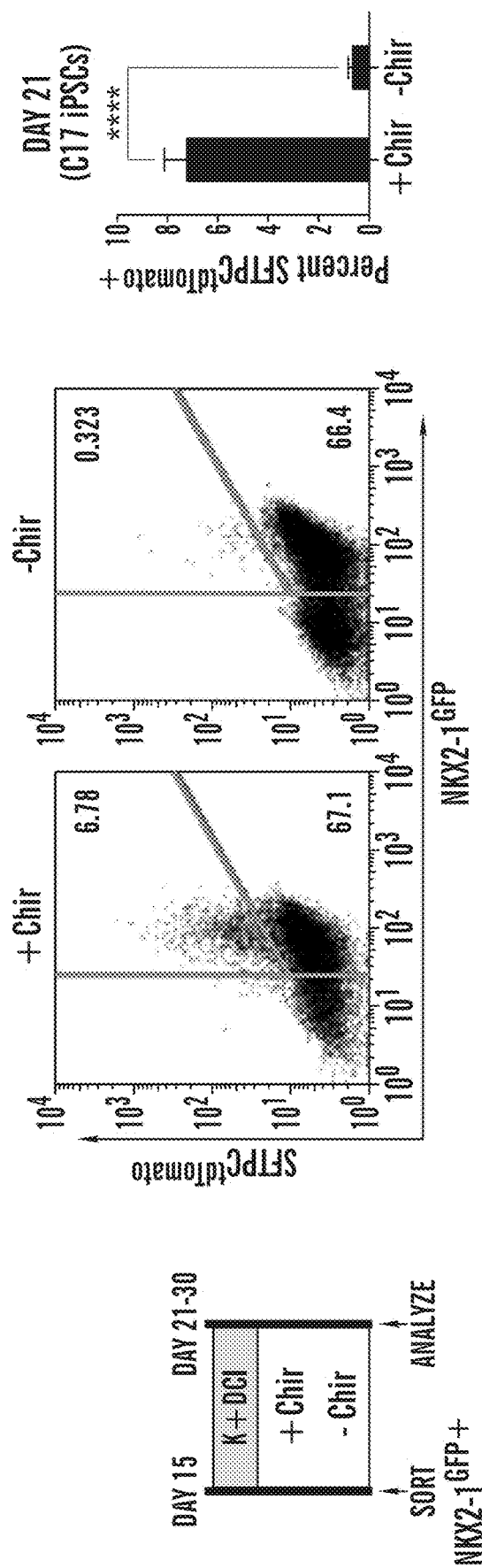
FIGS. 2A-2E demonstrate that putative iAEC2s proliferate and differentiate in long-term culture.

Having demonstrated that SFTPC+ cells derive via an NKX2-1+ progenitor intermediate, it was next sought to test whether Wnt activation was necessary and acting directly on these progenitors. Hence, NKX2-1GFP+ cells were purified on day 15 and the differentiation protocol in the presence or absence of CHIR (FIG. 2A, 9A). By day 21, induction of the SFTPCtdTomato reporter was evident in 7.17+/−0.89% of cells in the presence of CHIR, whereas only rare cells (0.64+/−0.34%) expressed the tdTomato reporter in the absence of CHIR, even when the cultures were maintained up to day 35. These findings are consistent with the observation (McCauley et al., in press) that CHIR distalizes NKX2-1+ human lung progenitors while suppressing proximal airway fates. Although KGF was dispensable for initial induction of the tdTomato reporter (FIG. 9A, 9B), it was found cells proliferated poorly in the absence of KGF or FGF10 (data not shown). In addition, KGF, when combined with CHIR, was more consistent in promoting the outgrowth of tdTomato+ cells by day 21 compared to FGF10+CHIR (FIG. 9B) (Liu & Hogan 2002).

Figure 2B:
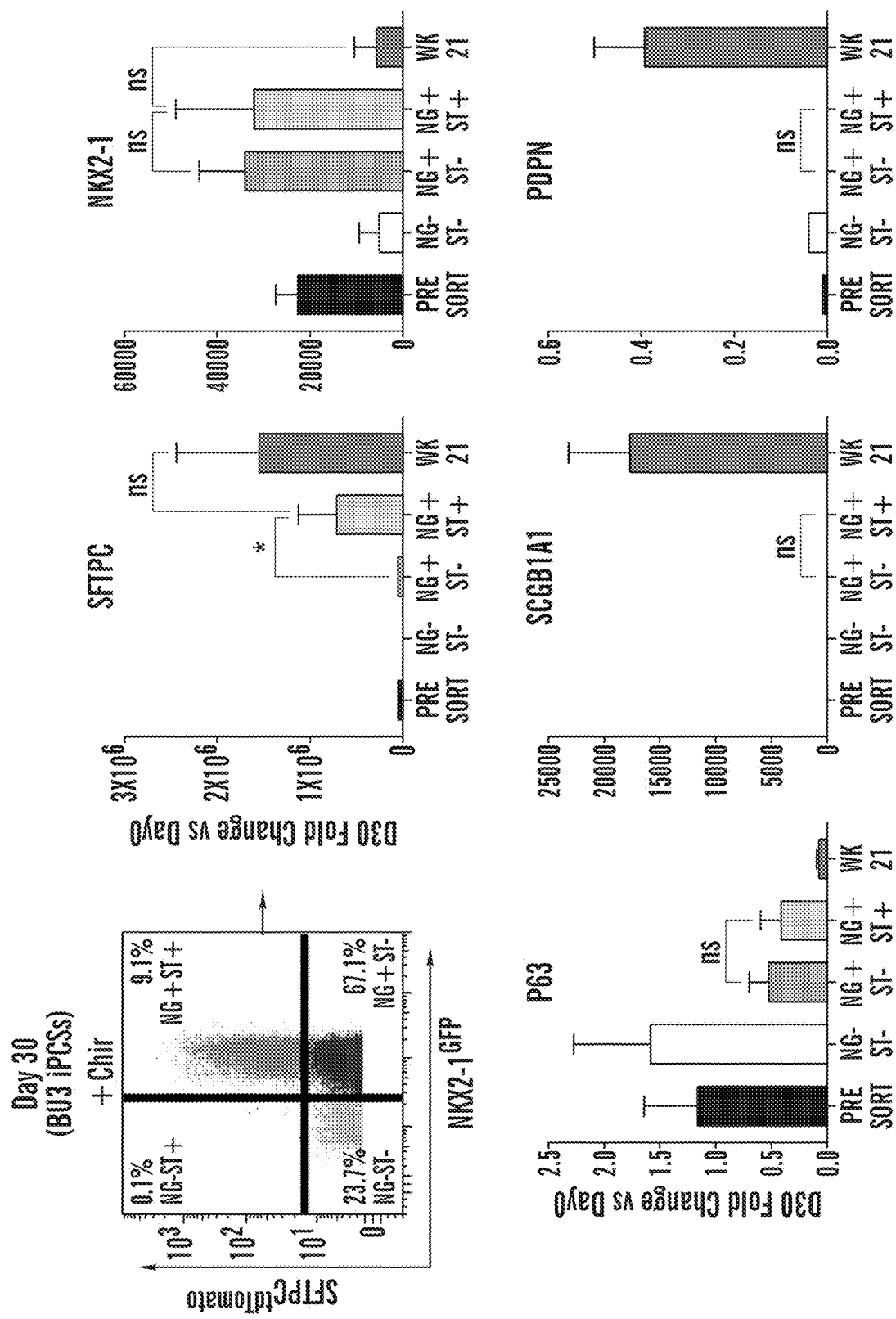

Having established a protocol for the derivation of SFTPC+ putative distal lung cells it was next sought to determine whether other lung lineages were co-developing in these cultures, focusing in particular on profiling the frequent NKX2-1+/SFTPC− cells that were present in these differentiations. Hence, each population was sorted for profiling on day 30 using each combination of the NKX2-1GFP and SFTPCtdTomato dual reporters present in the BU3 iPSC line (FIG. 2B). In the presence of CHIR and KGF, significant enrichment of SFTPC was observed in the NKX2-1GFP+/SFTPCtdTomato+ population (NG+ST+; FIG. 2B) whereas NKX2-1 was expressed equally in NKX2-1GFP+/SFTPCtdTomato+ cells compared to NKX2-1GFP+/SFTPCtdTomato−(NG+ST−) cells, as expected. In marked contrast no expression of the airway club cell marker, SCGB1A1 was observed in any population (FIG. 2B), and enriched expression of the basal cell marker P63 was observed in only the GFP− non-lung population, a finding in keeping with the observation that there is inefficient proximal airway patterning of iPSC-derived NKX2-1+ progenitors in the presence of high levels of CHIR-stimulated canonical Wnt signaling (McCauley et al, in press). When CHIR was withdrawn early (day 15-19) from sorted NKX2-1+ progenitors, the resulting cells in the presence of FGF stimulation demonstrated robust upregulation of proximal airway markers (SOX2, SCGB3A2, SCGB1A1, TP63, and MUC5B) without significant expression of SFTPC or other distal markers (McCauley et al., in press, and data not shown).

Figure 10A:
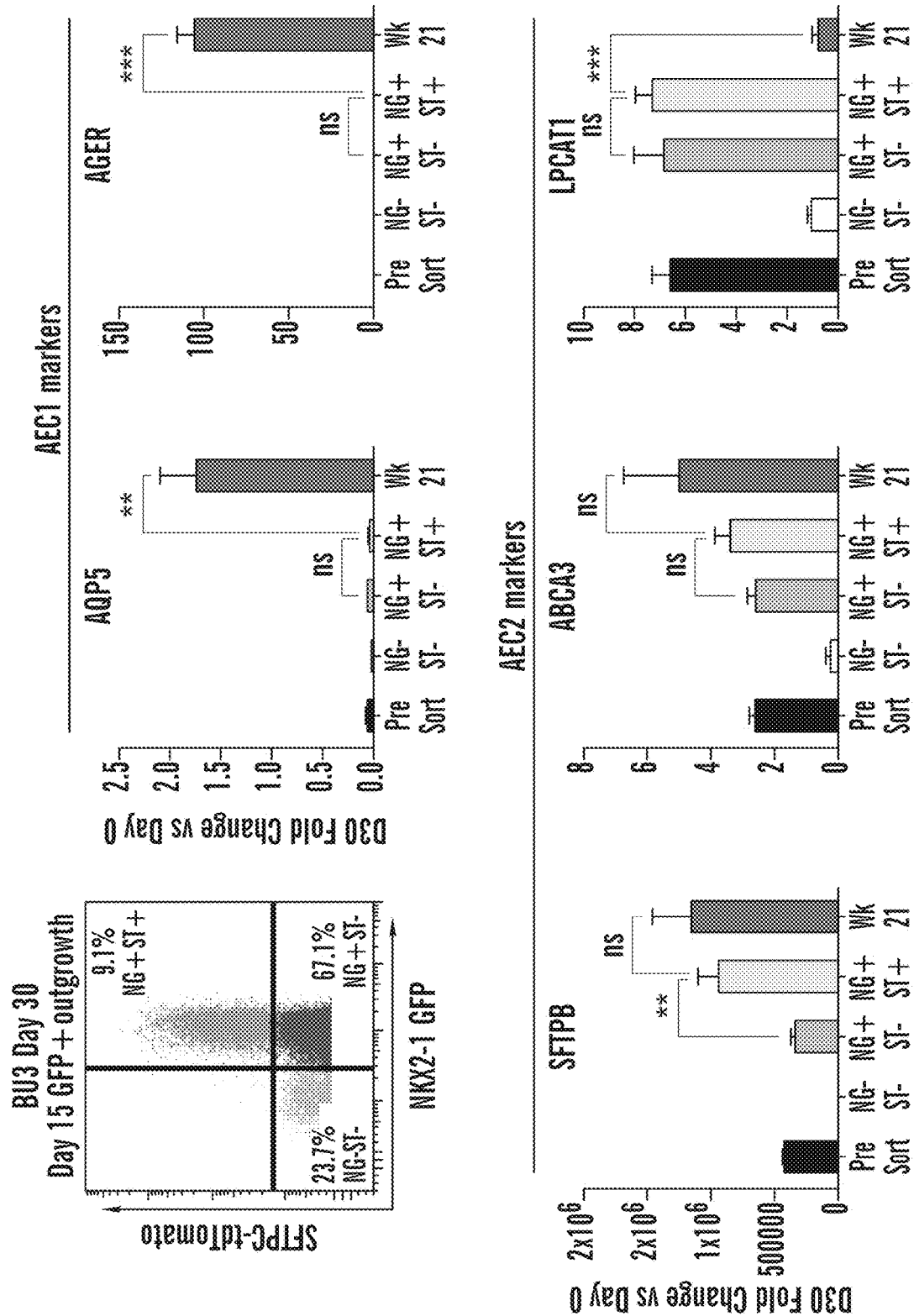
FIGS. 10A-10B demonstrate expression of alveolar transcripts pre- and post-alveolosphere passaging.

In the distalizing media (CK+DCI; FIGS. 1B and 2B) it was surprising to find little evidence of type 1 AEC (AEC1) differentiation in any population at the day 30 time point, as evidenced by low to undetectable levels of PDPN, AGER, and AQP5 (FIG. 2B, 10A). Similar findings were observed for later (day 35-50) time points (data not shown). Considering the finding that NKX2-1+SFTPC− cells in the day 30 population were not proximal lung cells or AEC1s, their expression of additional AEC2 markers was assessed and it was unexpectedly found that they expressed ABCA3, and LPCAT1 at high levels, similar to primary fetal AECs (FIG. 10A), raising the possibility that the NKX2-1+/SFTPC− population represents a less mature distal lung population compared to tdTomato+ cells which express significantly higher levels of SFTPC.

Figure 2C:
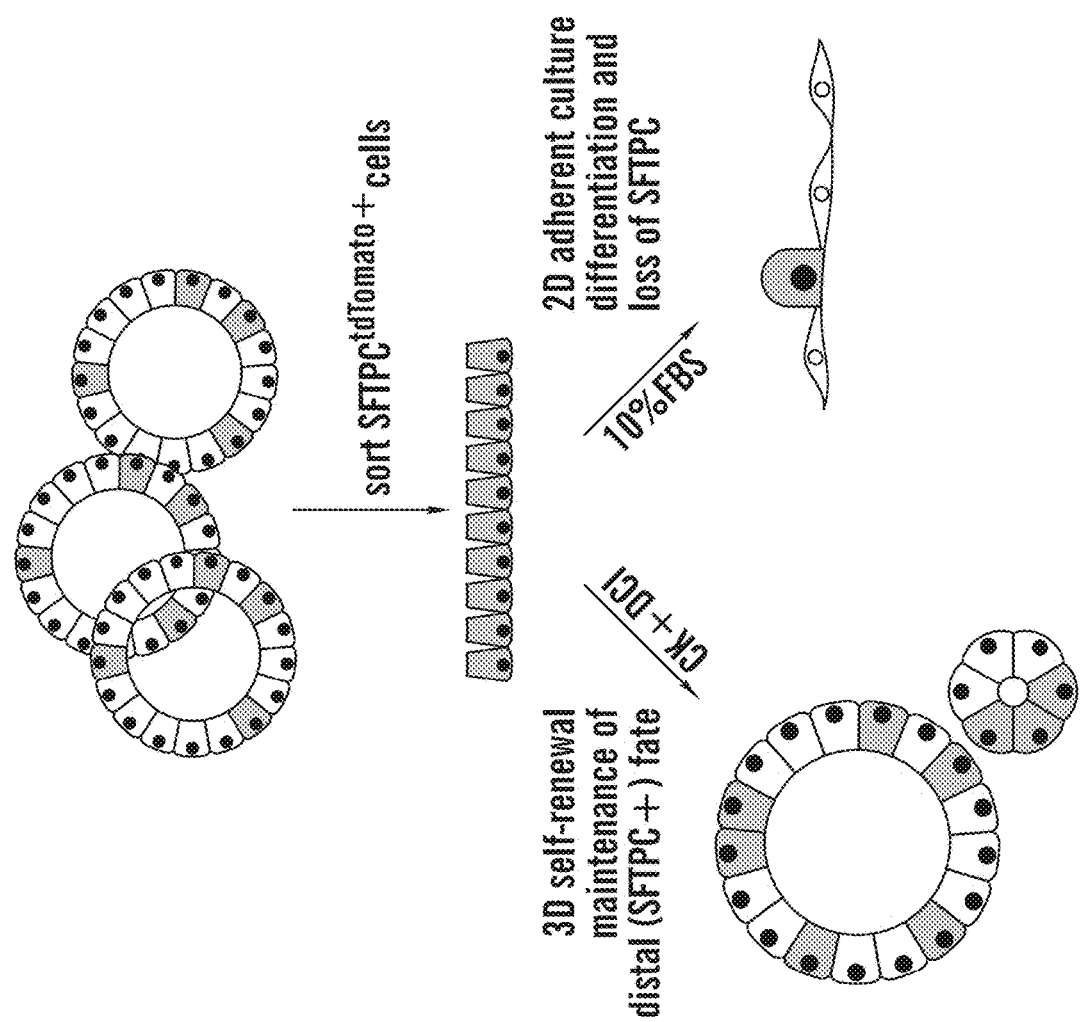
Figure 2C:
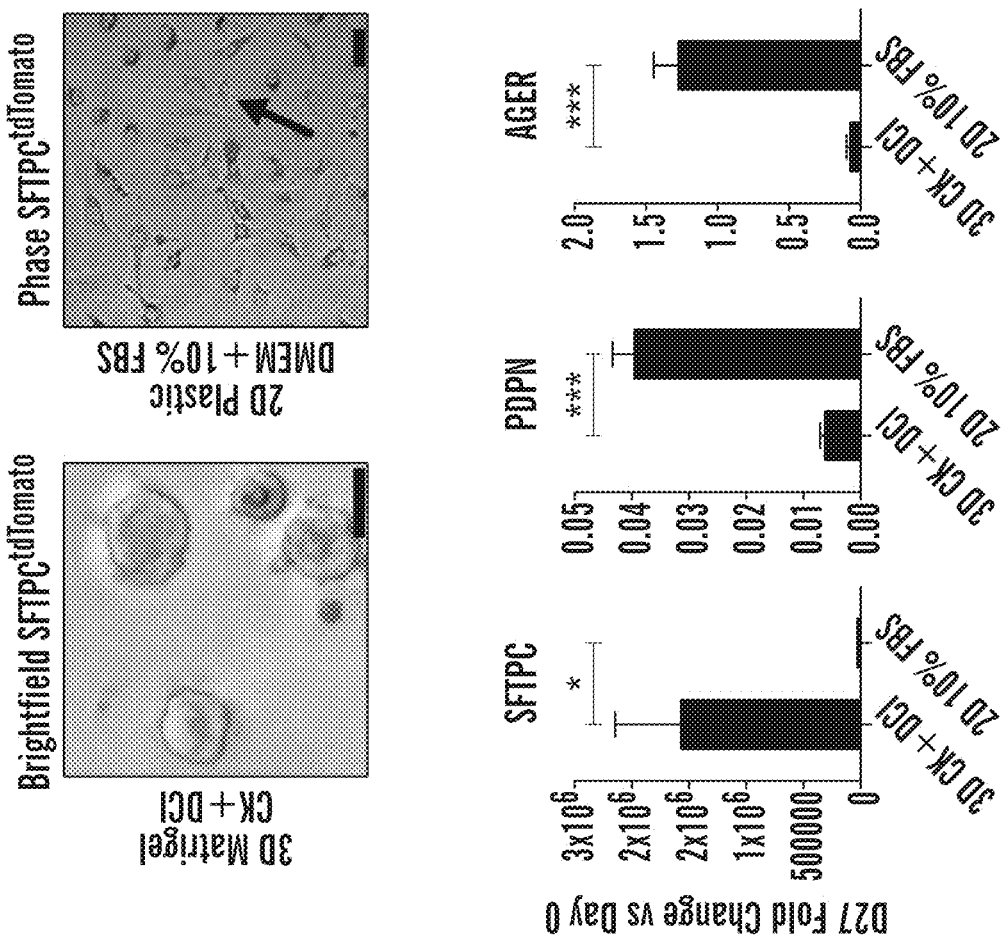

Putative iAEC2s display self-renewal and differentiation capacities. Given the absence of AEC1 differentiation in alveolospheres in distal 3D culture conditions, the capacity of PSC-derived SFTPC$^{tdTomato}$ sorted cells to differentiate when transferred to conditions that have been published as generating AEC I s from primary AEC2s was tested, such as 2D culture in serum-containing media without CK+DCI (Borok et al. 1998); (Dobbs et al. 1988). In contrast to parallel control SFTPC$^{tdTomato+}$ cells maintained in 3D distal conditions, it was observed that sorted PSC-derived SFTPC$^{tdTomato+}$ cells replated in these "AEC1 culture conditions" for 1 week rapidly flattened into squamous-like cells, significantly downregulated SFTPC, lost visible tdTomato reporter gene expression, and significantly upregulated PDPN and AGER (FIG. 2C).

Figure 2D:
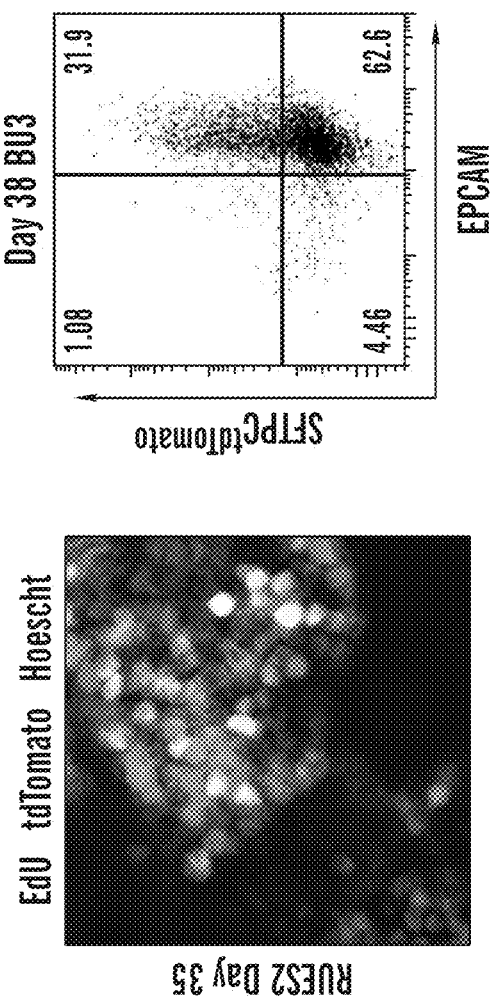
Figure 2E:
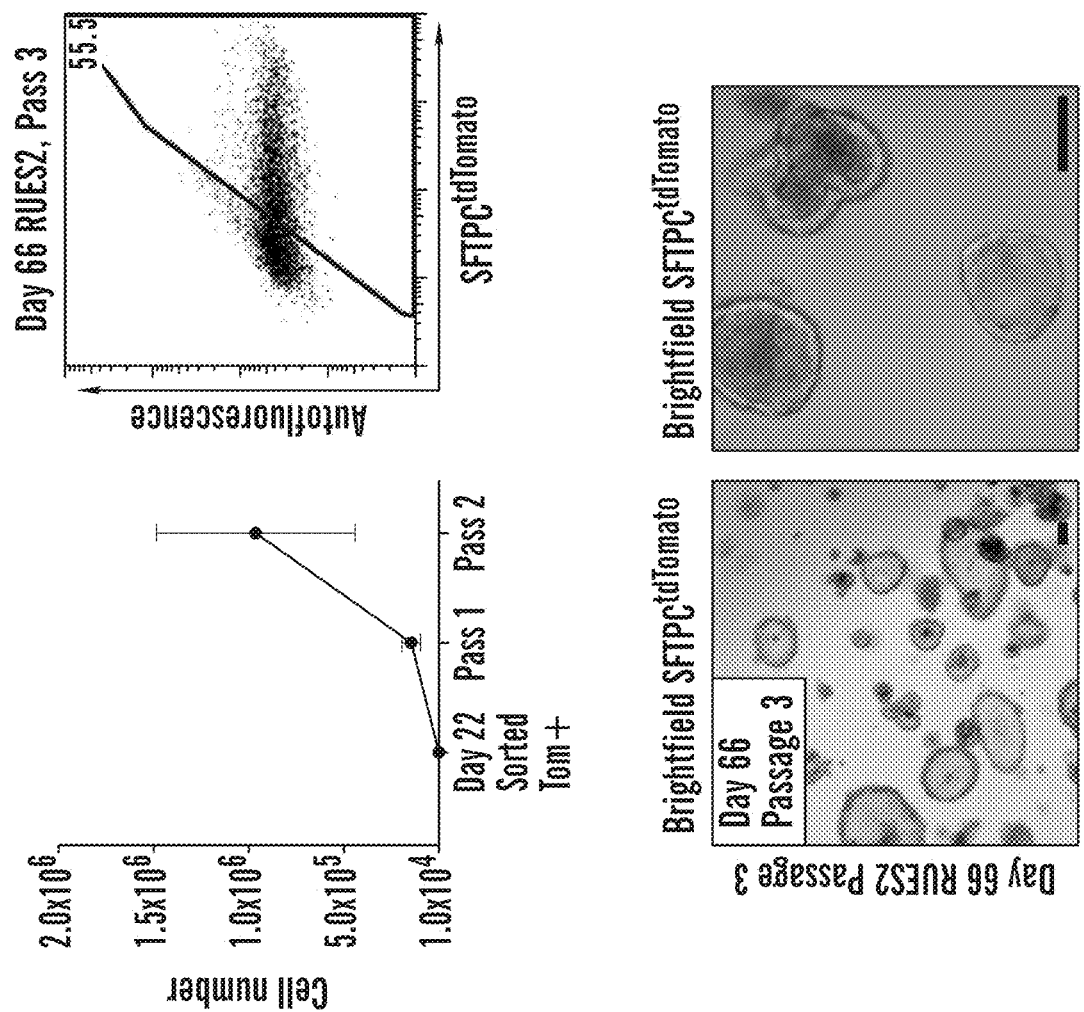
Figure 10B:
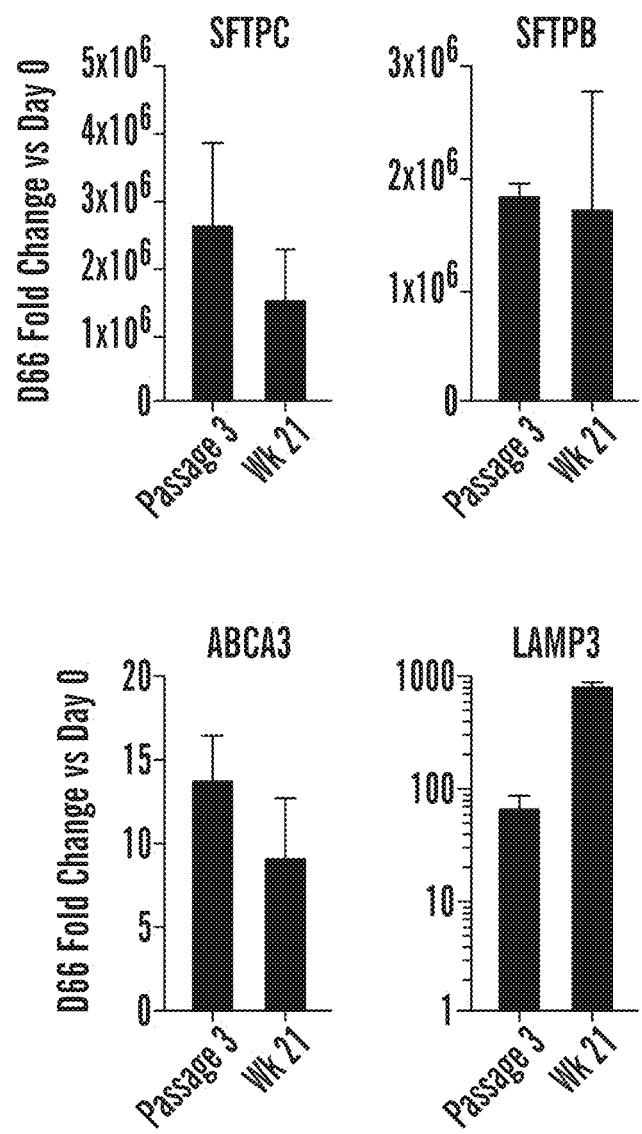

In addition to the capacity to differentiate, proliferation is a well-characterized property of both fetal and adult AEC2s (Barkauskas et al. 2013); (Desai et al. 2014), though long-term in vitro AEC2 proliferation has been shown to require mesenchymal feeders. It was found that in the absence of mesenchymal cells, with only the inductive signals provided in CK+DCI media, iPSC-derived SFTPCtdTomato+ cells within alveolospheres showed proliferative potential, as evidenced by their capacity to label with Edu (FIG. 2D). In addition, tdTomato+ cells sorted to purity on day 22 continued to increase in number during subsequent serial passaging and to re-form alveolospheres after each passage (FIG. 2E). After passaging, the resulting alveolospheres were composed of both tdTomato+ and tdTomato− cells providing direct evidence of a lineage relationship between the two populations. Both whole (unsorted) alveolar organoids and sorted SFTPCtdTomato+ cells maintained expression of the SFTPCtdTomato reporter in a subset of cells as well as mRNA expression of alveolar transcripts after multiple passages and freeze-thaw cycles (FIGS. 2E, 10B, and data not shown) further indicating significant self-renewal potential of PSC-derived SFTPC+ cells.

Figure 3A:
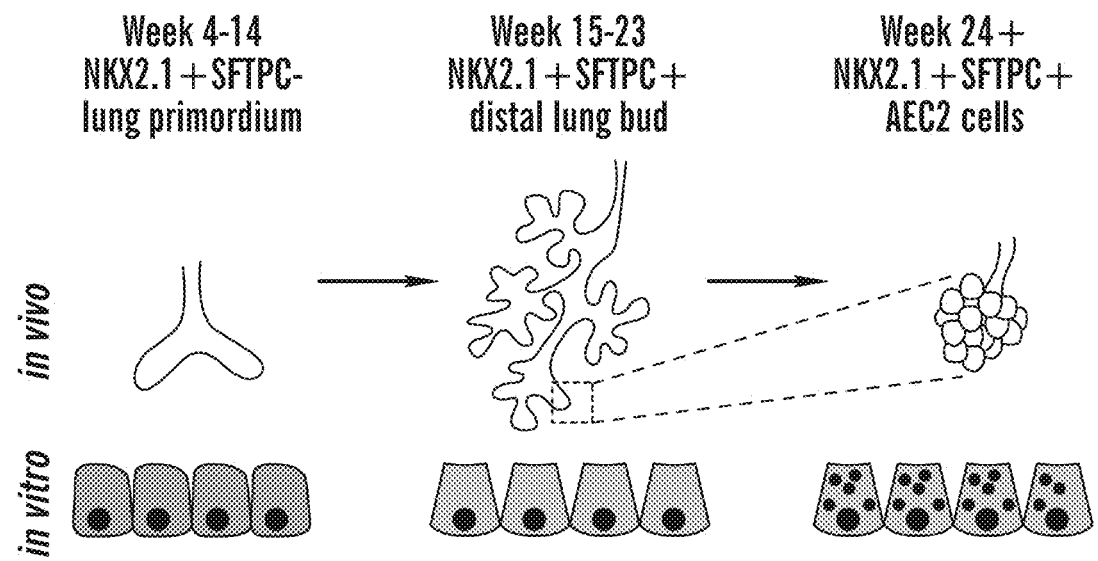
FIGS. 3A-3D demonstrate that putative iAEC2s express lamellar bodies that contain surfactant.
Figure 3B:
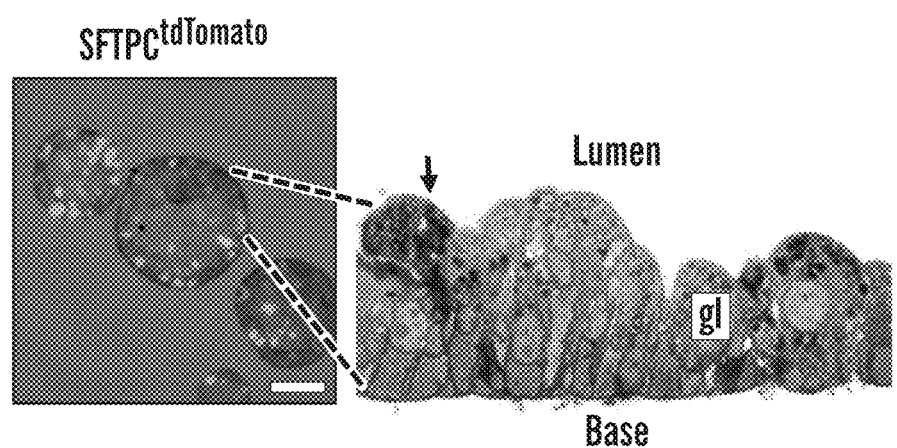
Figure 3C:
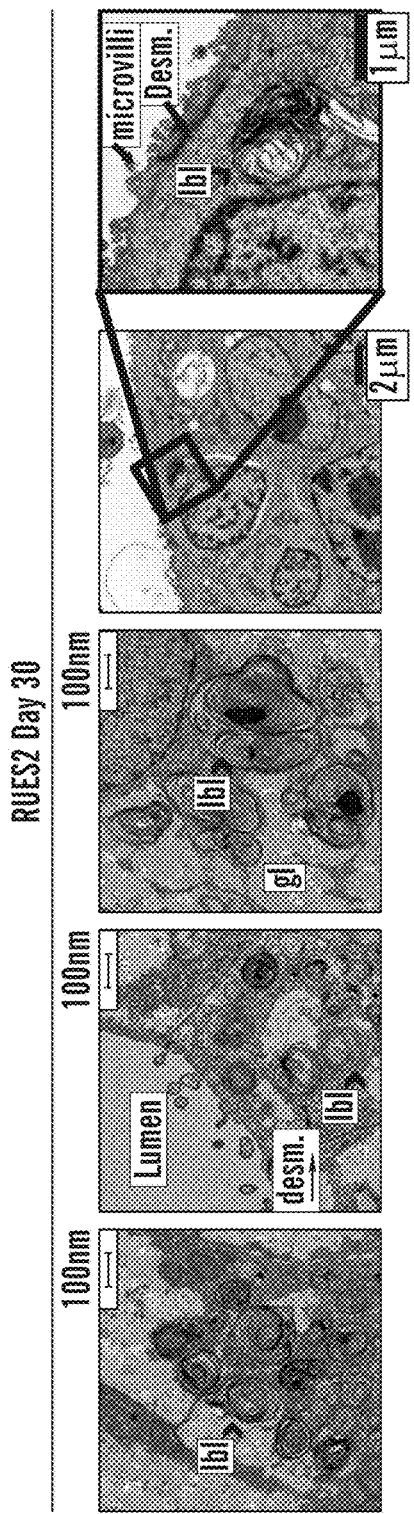
Figure 3D:
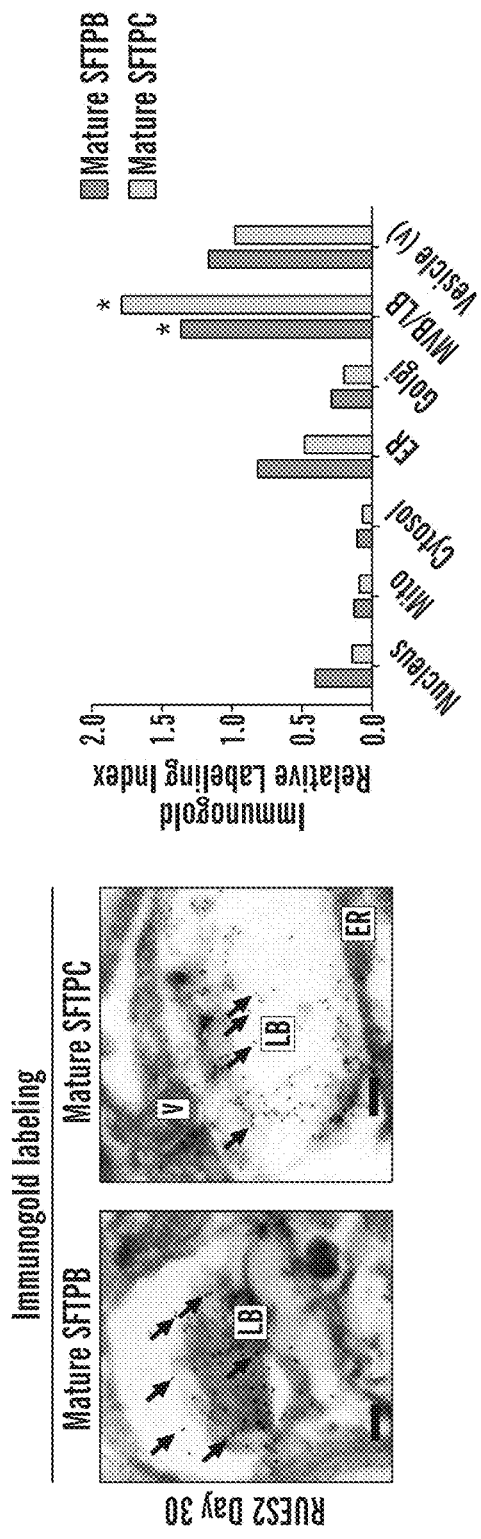
Figure 11A:
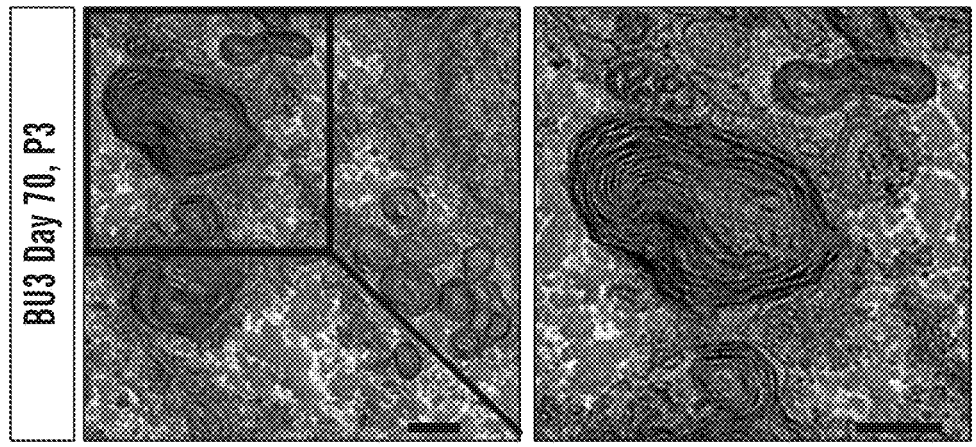
FIGS. 11A-11C demonstrate ultrastructural analysis of alveolospheres.

Putative iAEC2s express lamellar bodies that synthesize and secrete surfactant. The in vivo ultrastructural and biochemical characteristics of developing fetal and adult alveolar epithelia have been studied for more than 40 years, providing an extensive in vivo roadmap against which to compare iAEC2s (Williams & Mason 1977). Though alveolar progenitors express SFTPC or other surfactant markers in vivo as early as week 12-15 of human gestation (Otto-Verberne et al. 1988); (Khoor et al. 1994), they do not express functional lamellar bodies (LBs), the classic marker of AEC2 maturity, until after week 24 (FIG. 3A). Hence, it was assessed whether putative iAEC2s express these highly specialized organelles. Semi-thin plastic sections of PSC-derived alveolospheres revealed small inclusions clustering in the apical (luminal) side of the alveolosphere monolayer in a subset of cells (FIG. 3B), and ultrastructural analysis by transmission electron microscopy (TEM) showed these to be lamellar body-like inclusions (LBLs; FIGS. 3C and 11A-

Figure 11B:
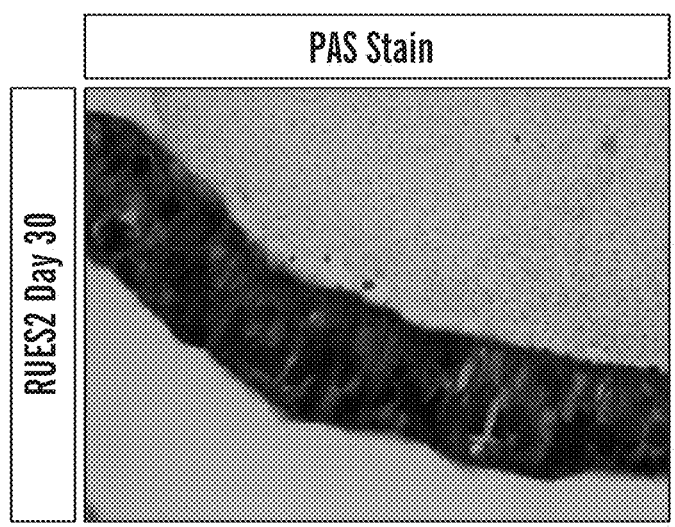
Figure 11C:
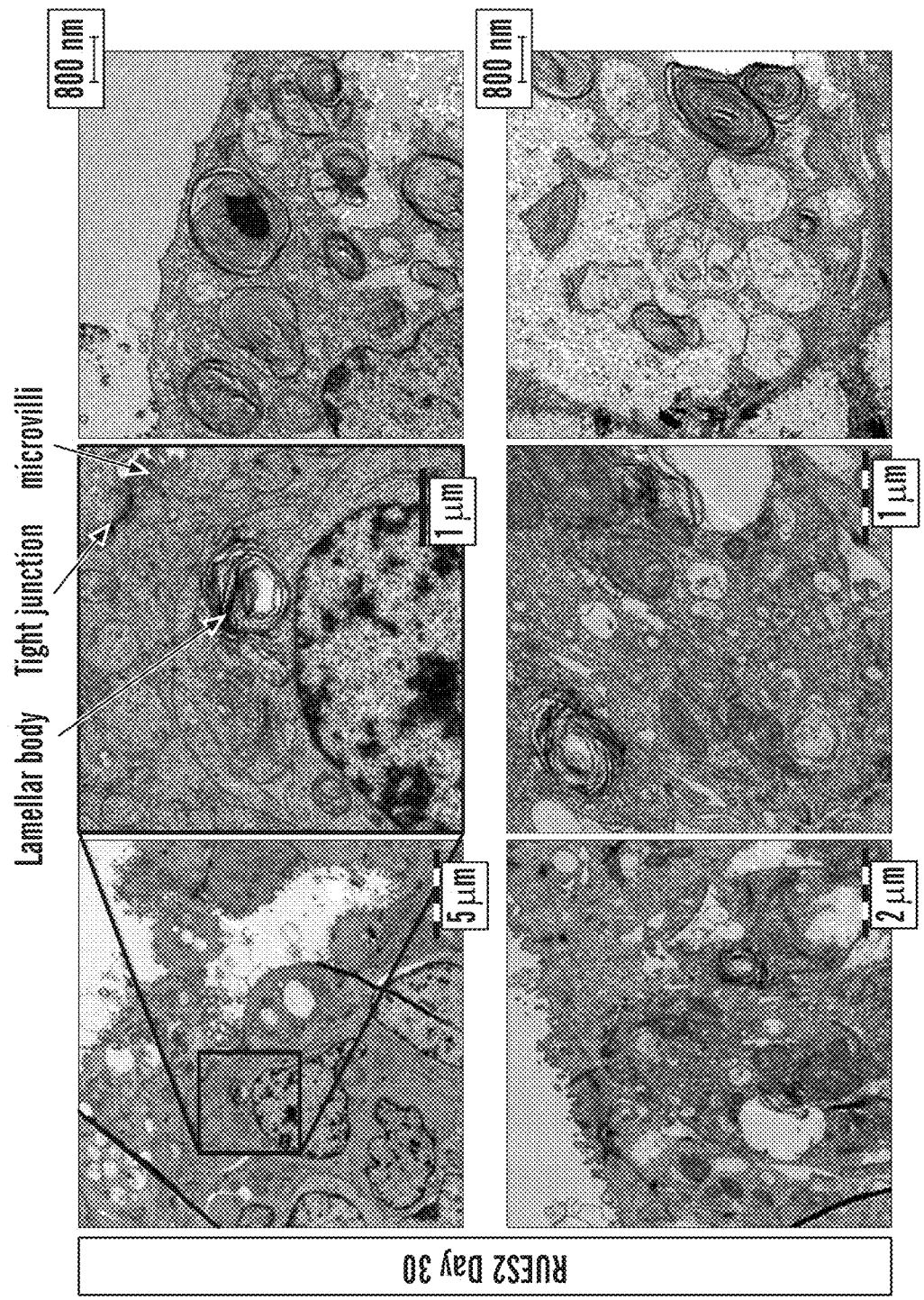

11C). As has been reported for adult AEC2 in vivo, LBLs in alveolospheres were approximately 1 micrometer in diameter, with some LBLs expressing central dense cores, a characteristic found in human but not rodent AEC2s. Even after multiple passages, Day 70 alveolospheres contained LBLs (FIG. 11A), further supporting the self-renewing capacity of putative iAEC2s. Within the cytoplasm of most cells, regardless of the presence of LBLs, large areas reminiscent of the glycogen rich regions (FIGS. 3B, 3C and 11A-11C) known to be expressed in fetal AEC2s just prior to birth were observed (Ridsdale & Post 2004), (Have-Opbroek et al. 1990). PAS staining confirmed the presence of cytoplasmic glycogen in the majority of cells within CD47hi/CD26lo− alveolospheres (FIG. 11B), further indicating putative iAEC2s resemble late fetal AEC2s.

To determine whether the LBLs observed in alveolospheres were true lamellar bodies, immunogold labeling was performed to identify the intracellular location of mature SFTPB and SFTPC protein forms. Mature forms of both proteins were found to preferentially localize to LBLs and their precursor organelles, multivesicular bodies (MVBs) within alveolospheres (FIG. 3E), findings consistent with those reported for mature AEC2 in vivo (Brasch et al. 2004); (Korimilli et al. 2000).

Figure 4A:
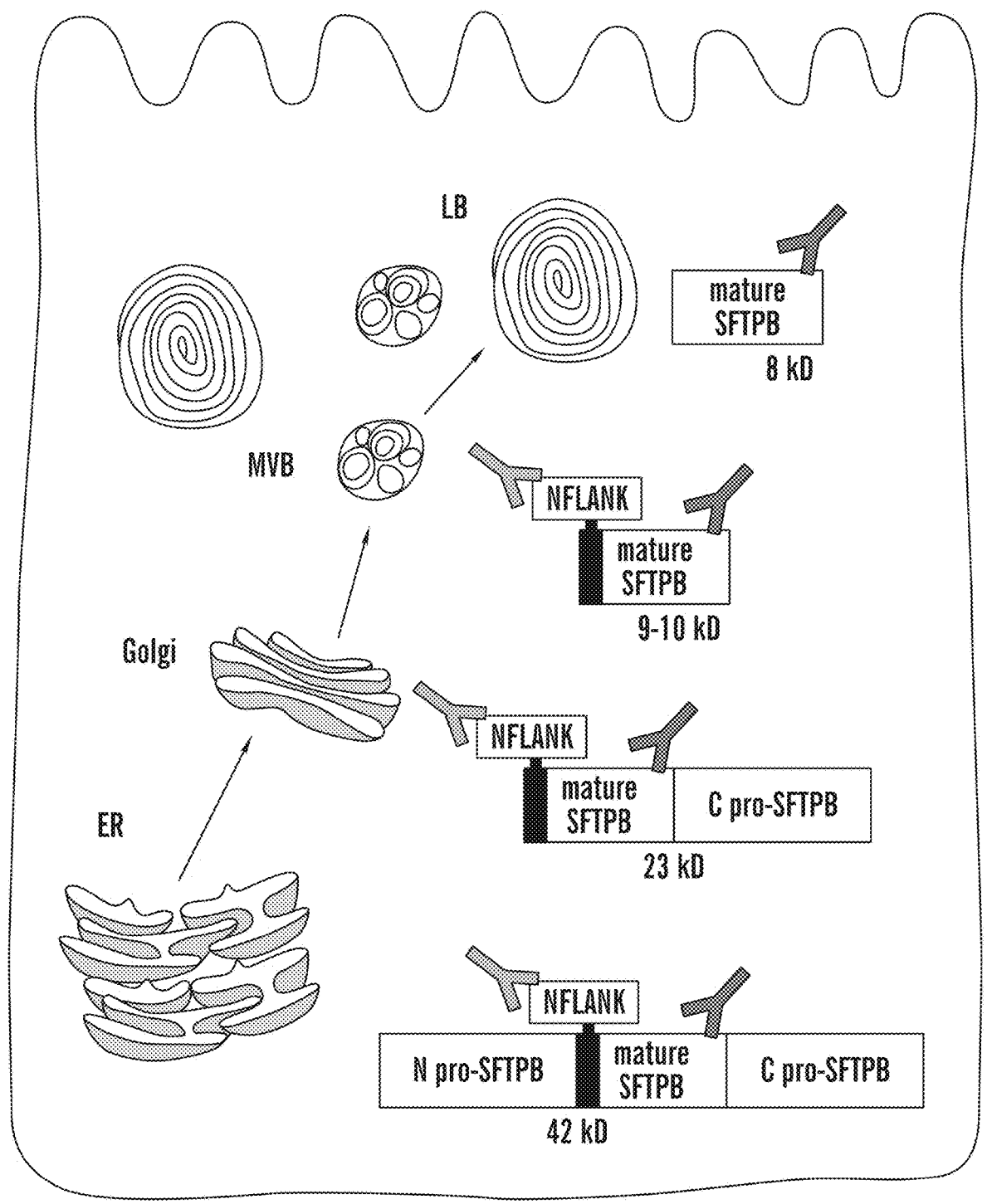
FIGS. 4A-4C demonstrate that putative iAEC2 lamellar bodies function to synthesize and secrete surfactant.
Figure 4B:
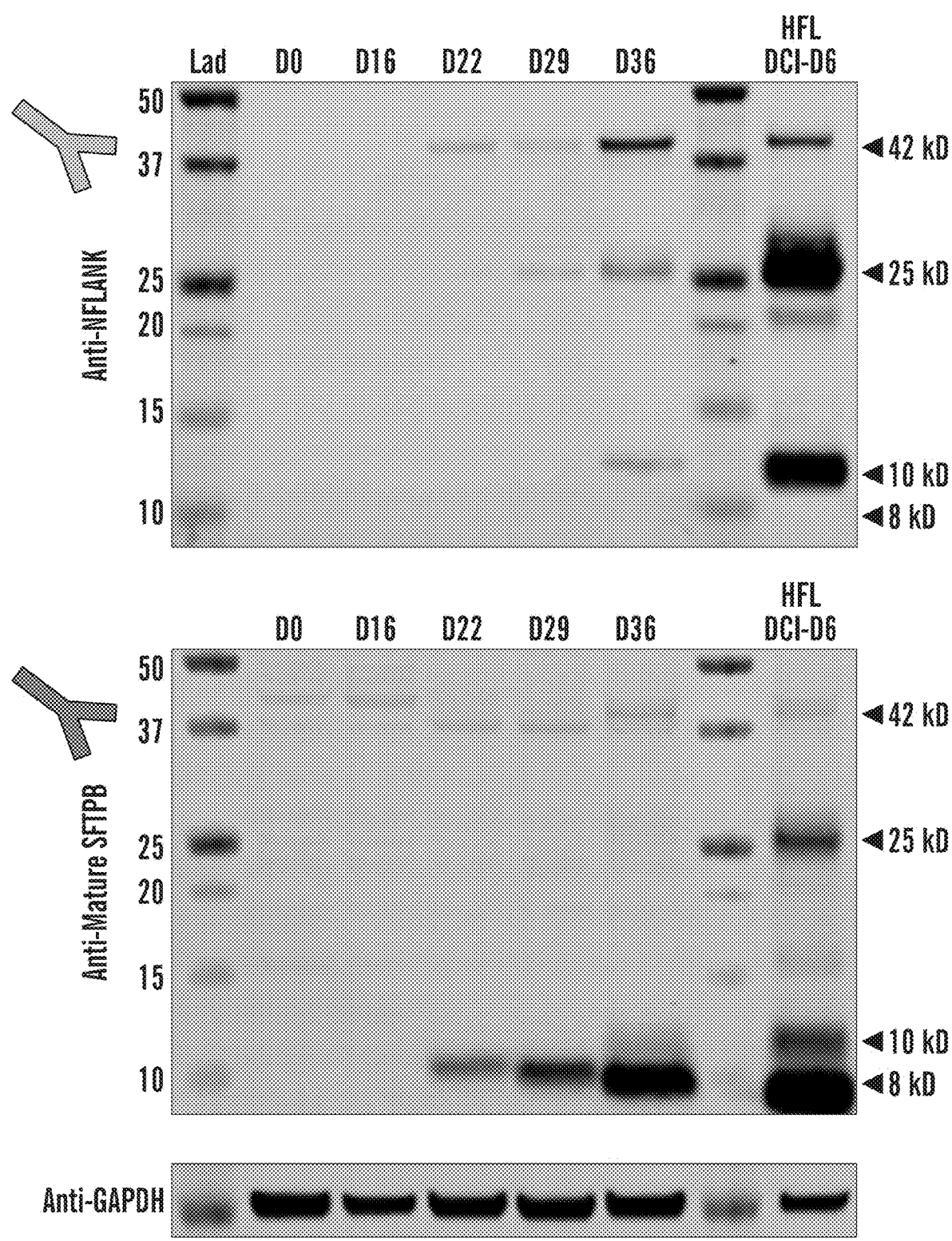

To further test the functionality of putative iAEC2s, it was asked whether the cells were able to process proSFTPB protein to its fully mature 8kD form (FIG. 4A). (Guttentag et al. 1998), because the last cleavage step in proSFTPB processing occurs in the functional MVBs and LBs of post-week 24 gestation human AEC2s (Brasch et al. 2004). Importantly, it was found that iAECs expressed high levels of the genes required for proSFTPB proteolysis (Foster et al. 2004), including PGC, Napsin A (NAPSA), and Cathepsin H (CTSH) (data not shown). Hence, a time series of protein extracts prepared from RUES2 cells during distal lung differentiation in vitro were analyzed. Western blots immunostained with antibodies able to discern fully processed mature 8 kD SFTPB (PT3 antibody) vs proSFTPB precursor forms (NFLANK antibody; FIGS. 4A,4B) revealed increasing production of both the precursor and mature forms of SFTPB beginning on day 22 of differentiation and increasing over time through day 36 (FIG. 4B). Compared to primary fetal human AEC2 controls, PSC-derived cells similarly expressed 42 kD, 23 kD, and 10 kD precursor forms as well as mature 8 kD SFTPB protein. Moreover, as with primary controls, SFTPB appeared to be efficiently processed in alveolospheres as the predominant SFTPB form detected was the mature form (FIG. 4B). The larger precursor SFTPB forms were only visible when the "NFLANK" specific antibody was used to detect the proSFTPB region that is present prior to final cleavage into the mature form.

Figure 4C:
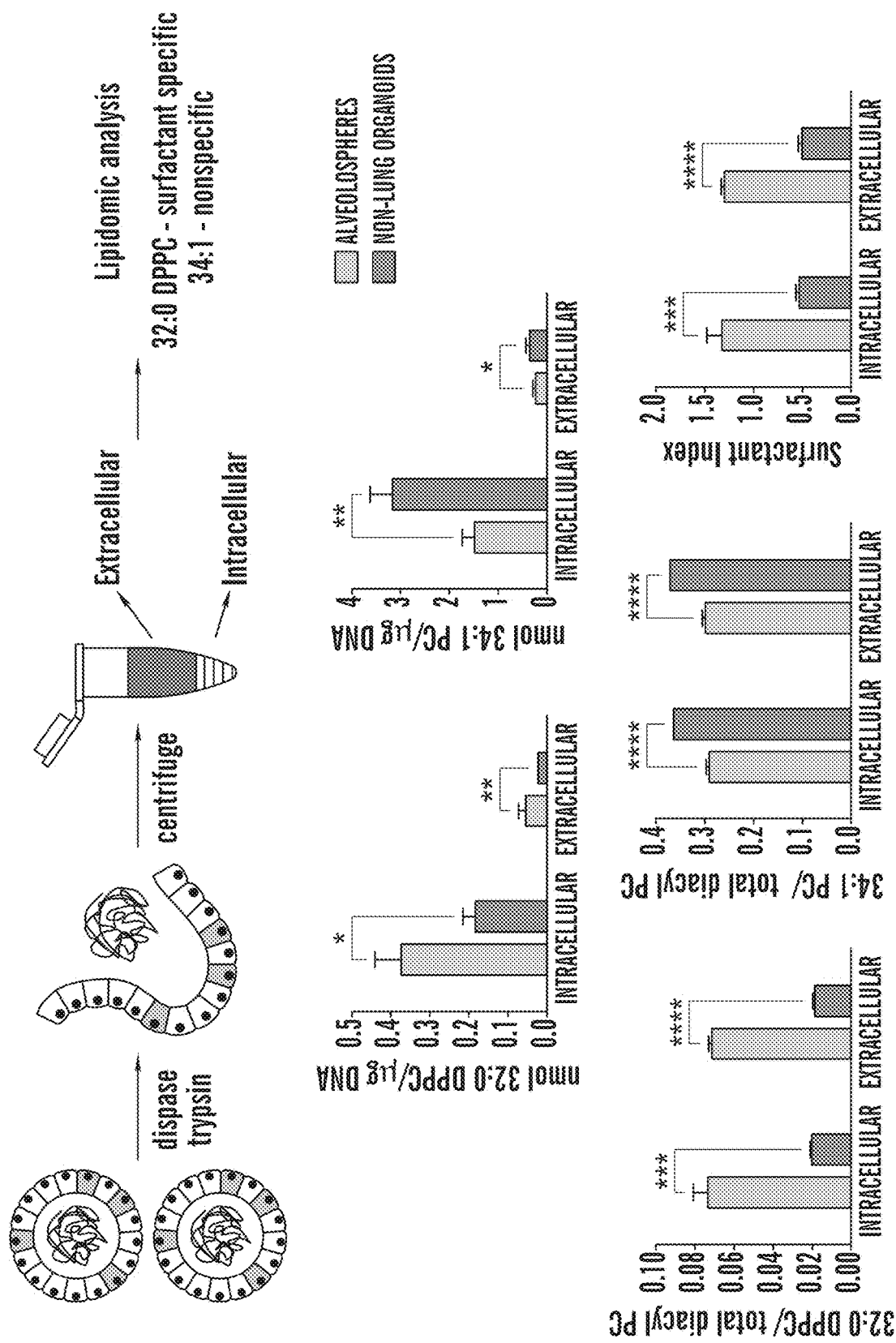

To determine whether putative iAEC2s synthesize and secrete surfactant-specific 32:0 dipalmitoyl phosphatidylcholine (DPPC), lipidomic analysis was performed on both the intracellular and extracellular material from iPSC-derived alveolospheres. Since these spheres appear to be polarized with the apical surface pointing inwards, they were dissociated with dispase and trypsin in order to free the secreted products, and then the analysis was performed on the supernatant fractions and the cells separately (FIG. 4C). Both the relative and absolute amounts of DPPC were significantly higher in the intracellular and extracellular material from the alveolospheres generated from PSCs via NKX2-1+ progenitors (isolated by CD47hi/CD26lo sorting) compared to control spheres generated from endodermal progenitors depleted of NKX2-1+ cells. Taken together, these results show that PSC-derived alveolospheres contain cells with functional lamellar bodies that synthesize, store, and secrete surfactant, indicating that they contain phenotypically mature AEC2-like cells, hereafter referred to as iAEC2.

Figure 5A:
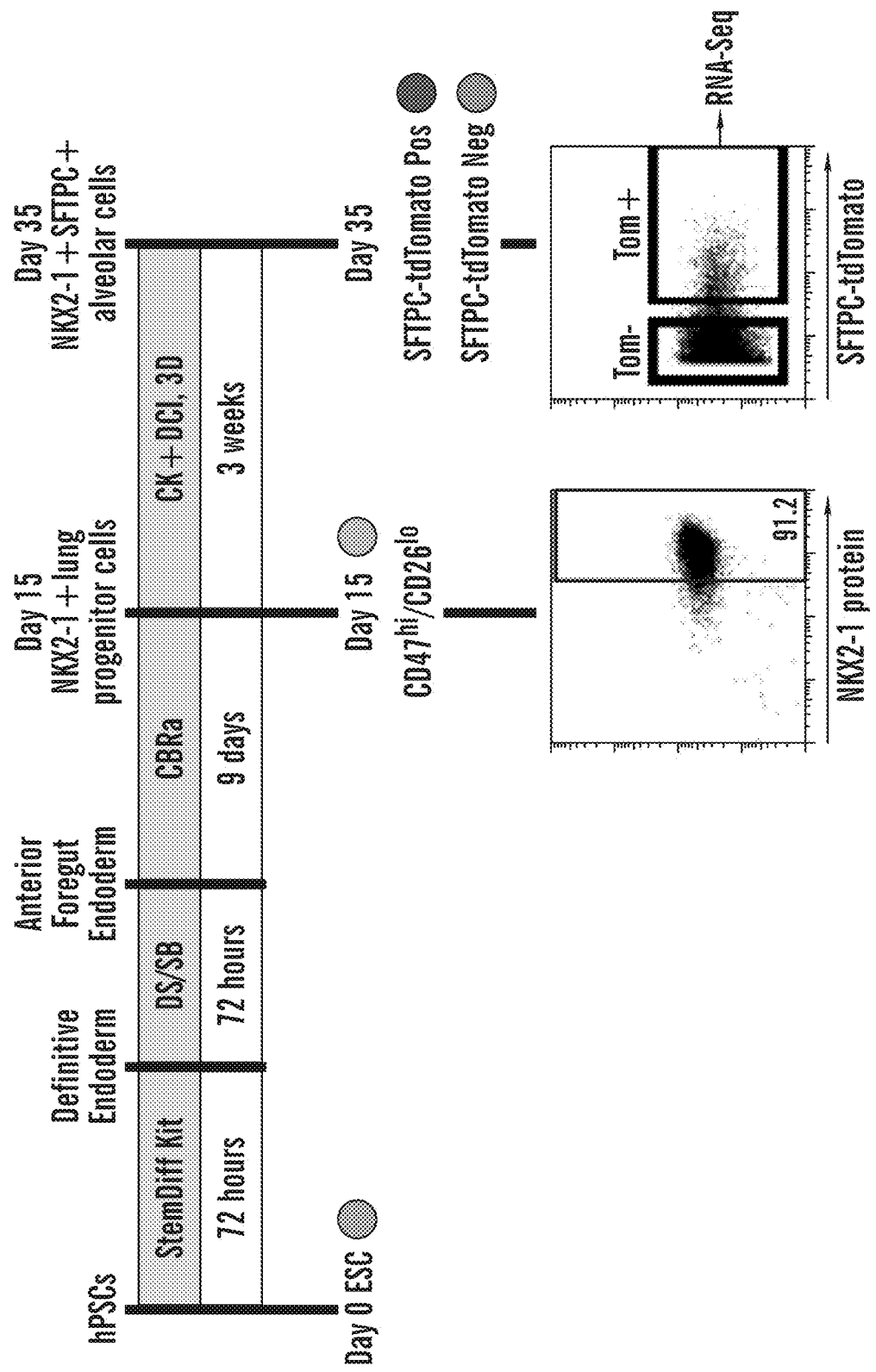
FIGS. 5A-5H demonstrate global transcriptomic profiling of PSC-derived lung progenitors and their differentiated iAEC2 progeny.

Global transcriptomic profiling of PSC-derived lung progenitors and their differentiated iAEC2 progeny. It was next sought to define the global transcriptomes of PSC-derived lung progenitors and their SFTPC+ and SFTPC− progeny in an unbiased way by performing a time-series analysis using RNA sequencing (RNA-Seq). 3 different timepoints in the RUES2 differentiation were analyzed: 1) Day 0 undifferentiated cells, 2) Day 15 lung progenitors highly enriched in NKX2-1+ cells by CD47hi/CD26lo sorting (hereafter CD47+), and 3) the outgrowth of these purified progenitors in 3D culture sorted again on Day 35 based on SFTPC$^{tdTomato+}$ (Tom+) and SFTPC$^{tdTomato-}$ (Tom−) gating (FIG. 5A). For comparison to primary cells, we simultaneously sequenced RNA from purified primary fetal (21 week gestation) distal alveolar epithelial progenitors and sorted adult human AEC2s. In order to evaluate the effect of cell culture on primary fetal alveolar cells, parallel samples of the fetal cells were also exposed to 4 days of culture in DCI media.

Figure 5B:
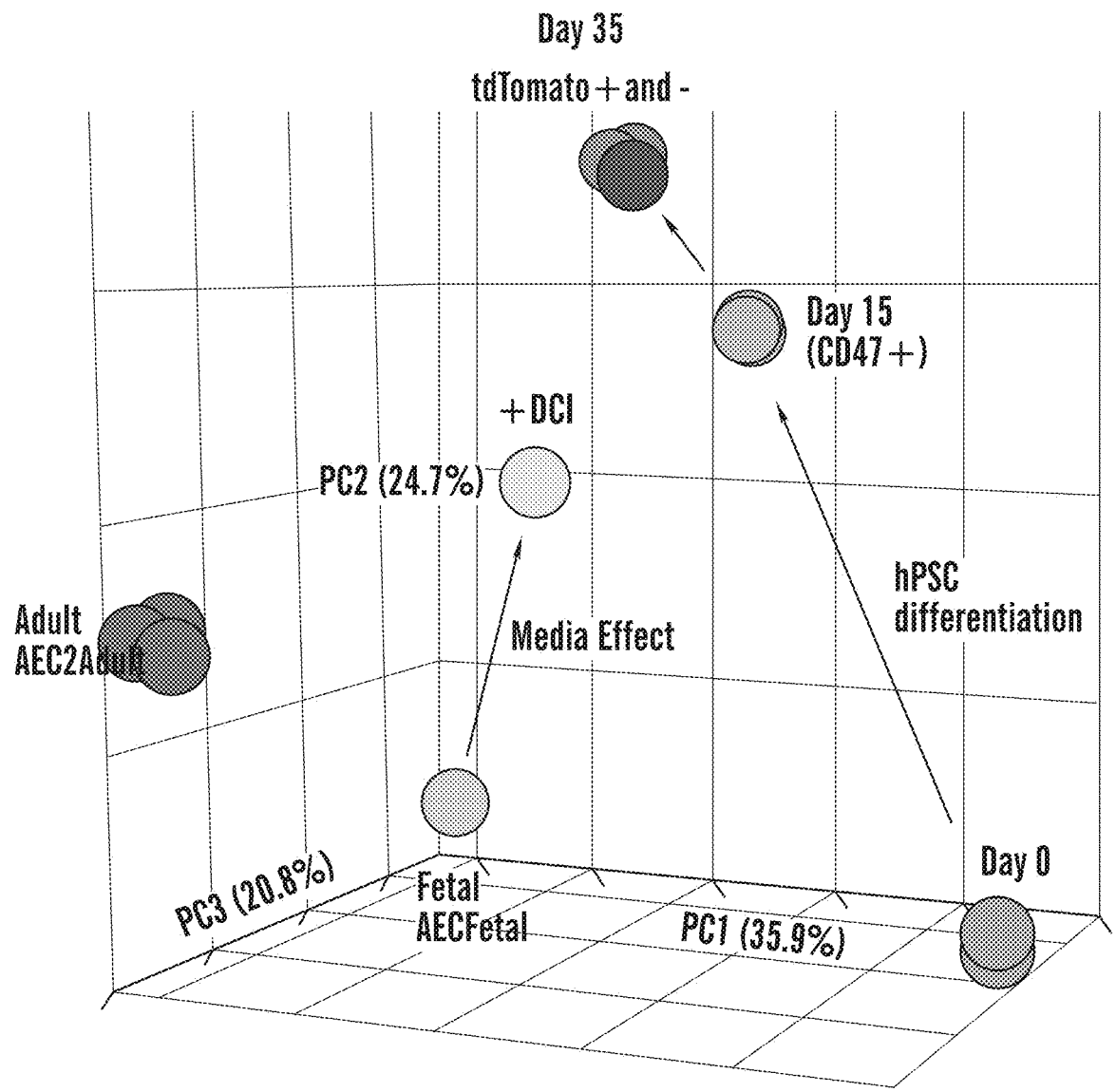
Figure 5C:
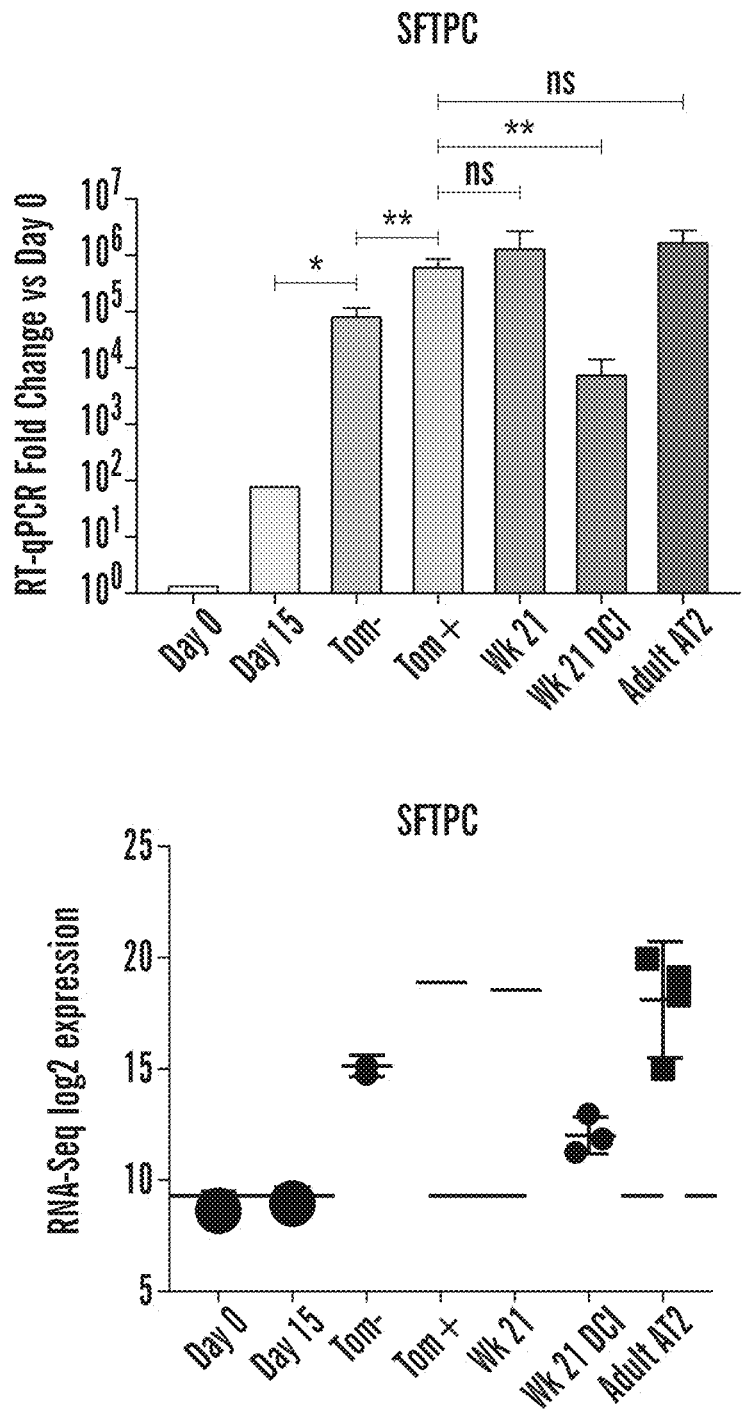
Figure 5D:
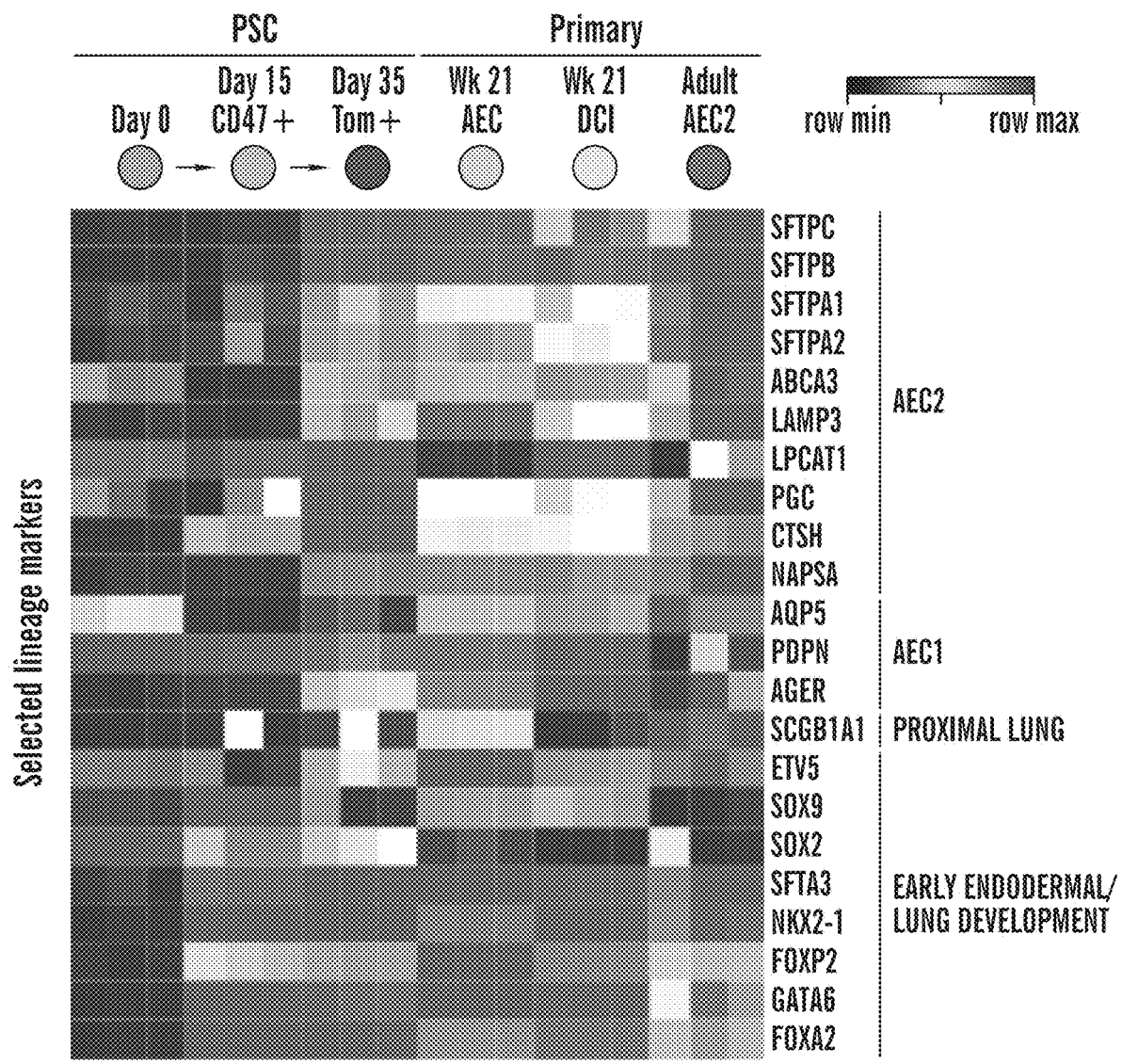
Figure 5E:
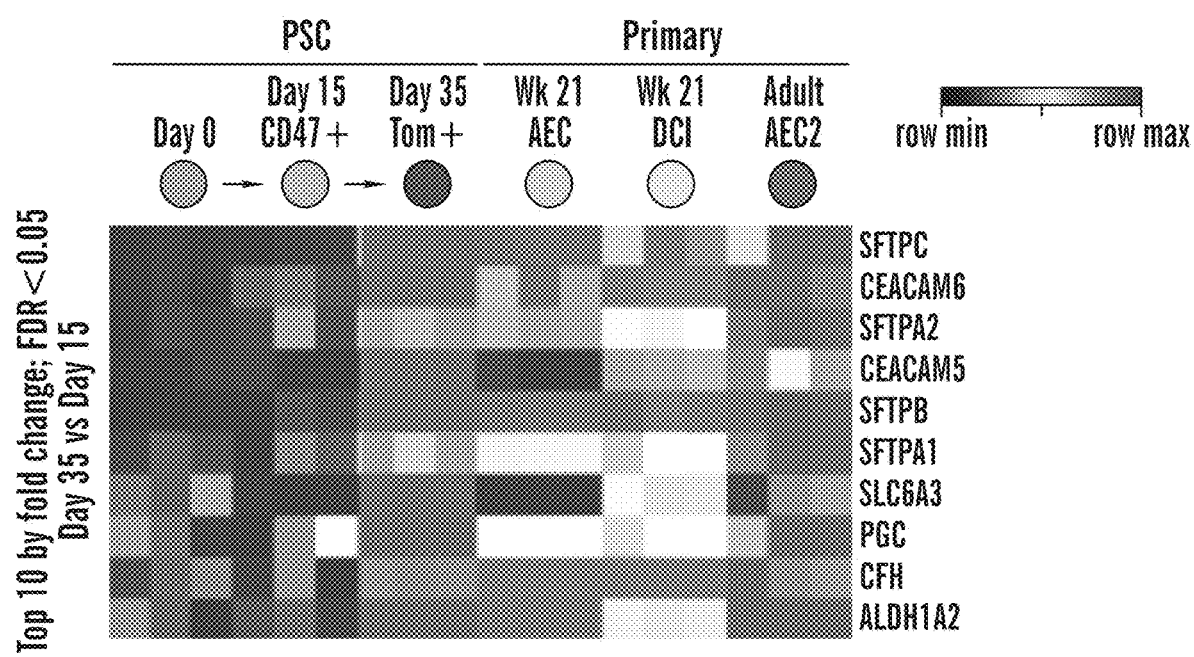
Figure 5F:
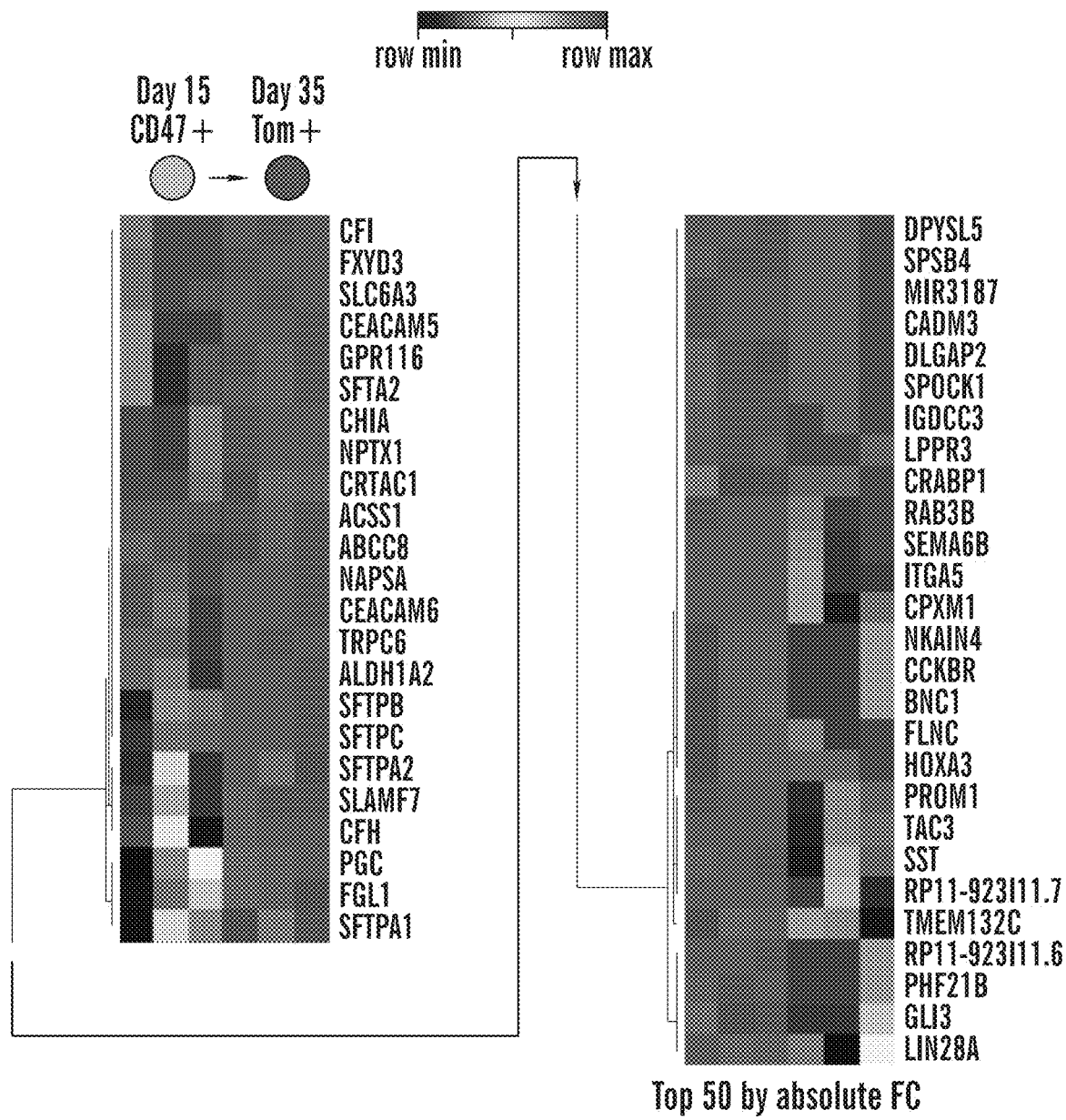
Figure 5G:
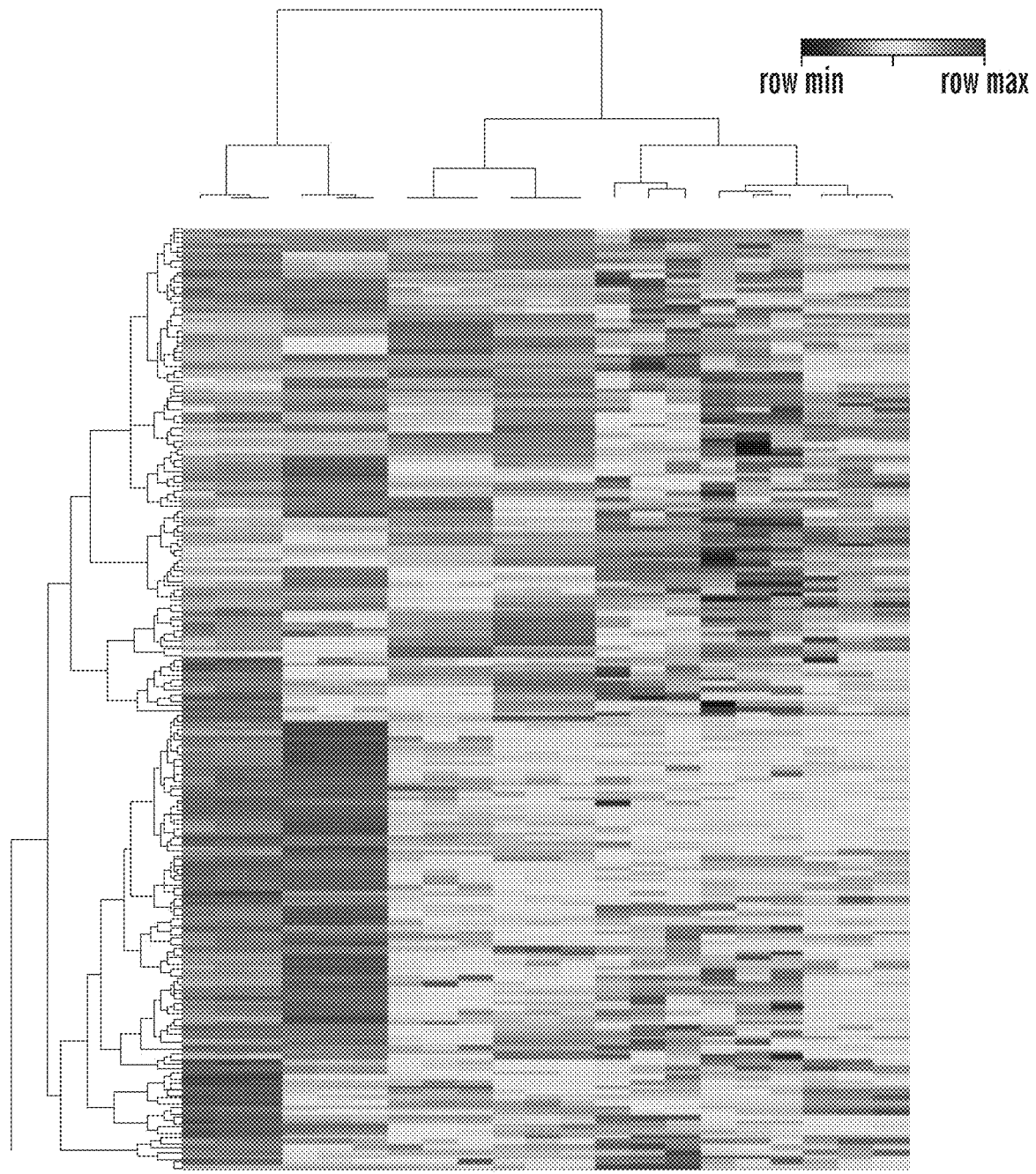
Figure 5G:
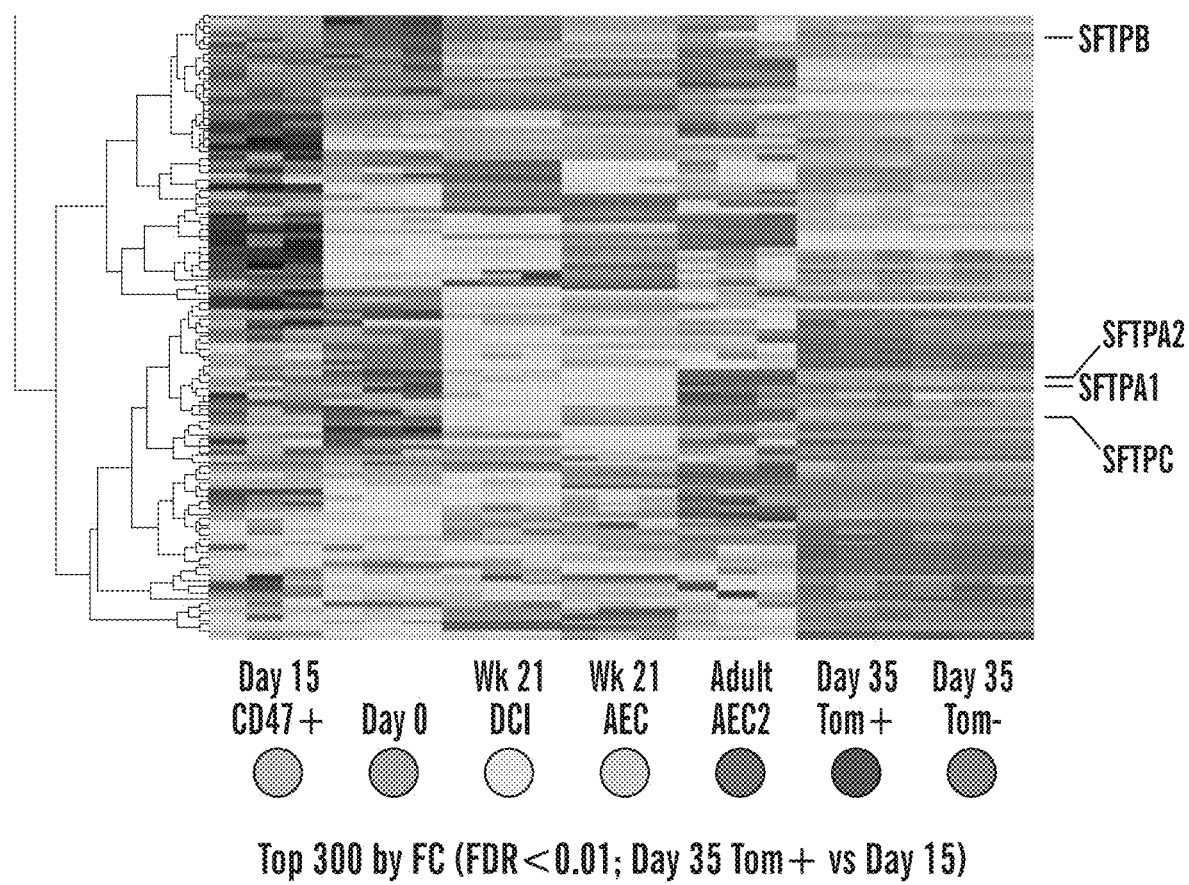
Figure 12B:
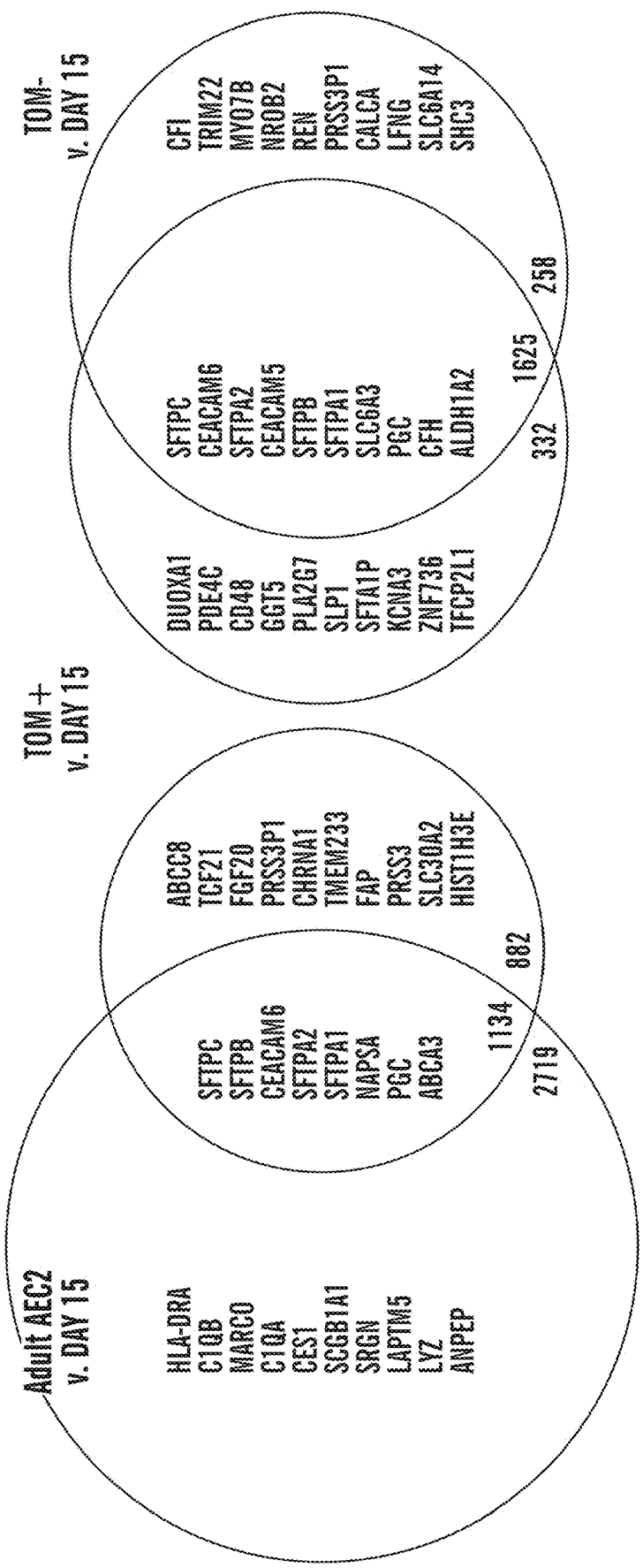
Figure 12D:
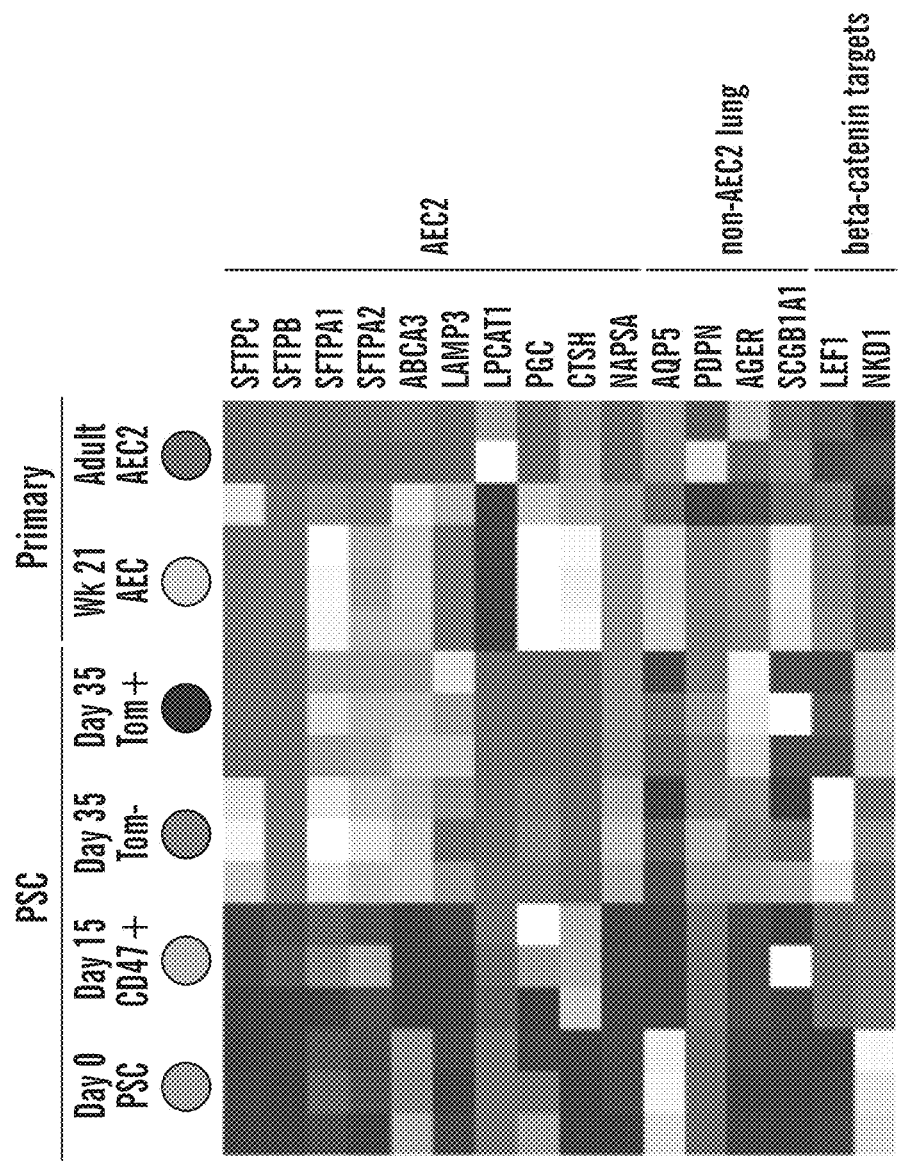

By principal component analysis (PCA) of 30,000 transcripts in each sample, it was found that PSC-derived cells after 35 days of differentiation clustered closer to primary cells on the PC1 axis (FIG. 5B). In addition, on both PC1 and PC2 axes, fetal primary cells clustered closer to PSC-derived cells after cell culture in DCI media, whereas sorted adult AEC2 clustered separately from all other samples. In keeping with this finding, profiling of both the canonical marker, SFTPC (FIG. 5C) as well as a selected set of 22 markers of AEC2s, AEC1s, and early lung endoderm (FIG. 5D), showed that expression patterns most closely resembled primary AECs in the sorted PSC-derived cells at day 35. To identify genes differentially expressed in Tom+ cells with differentiation, the sorted day 35 Tom+ cells were compared with their day 15 precursors (FIGS. 5E,5F,5G and 12C). Notably, it was found that the set of 50 most differentially expressed transcripts in day 35 Tom+ cells were highly enriched in AEC2-specific marker genes (ranked by absolute fold change and FDR≤0.01; FIG. 5F). Strikingly, 7 out of the top 10 most differentially upregulated genes in Tom+ cells encoded proteins related to surfactants or lamellar body biogenesis (FIG. 5E). Furthermore, comparing expression levels across all samples, these genes were expressed in PSC-derived Tom+ cells at levels similar to adult AEC2s (FIG. 5E). Indeed, hierarchical clustering analysis of all samples based on the top 300 differentially expressed genes in the Tom+ population indicated that these cells clustered closest to adult AEC2 (FIG. 5G). Unexpectedly, Tom+ and Tom− cells displayed similar gene expression profiles by both PCA of all 30,000 transcripts and hierarchical clustering analyses of the top 300 genes upregulated from Day 15 to 35 in Tom+ cells (FIGS. 5B, 5G and 12B, 12D), and they expressed multiple AEC2 marker genes at levels similar to adult AEC2s with the exception of SFTPC, which was significantly upregulated in the Tom+vs the Tom-population (FIGS. 5C and 12D).

Potential gene expression differences between the various samples were examined. First, the transcriptomic differences between PSC-derived Tom+ cells and primary cells were examined, expecting to see major differences in global gene expression in iAEC2s when compared to primary adult AEC2s due to the effects of accelerated development of iAEC2s outside of the alveolar niche in submerged sterile cultures vs the effects of life-long maturation of adult AEC2s in an air breathing, multilineage, non-sterile environment. Not surprisingly GSEA analysis of Tom+ cells v. adult AEC2s revealed that the gene sets differentially expressed in adult AEC2s involved upregulation of immune pathways and oxidant stress (FIG. 12A,12C).

Figure 5H:
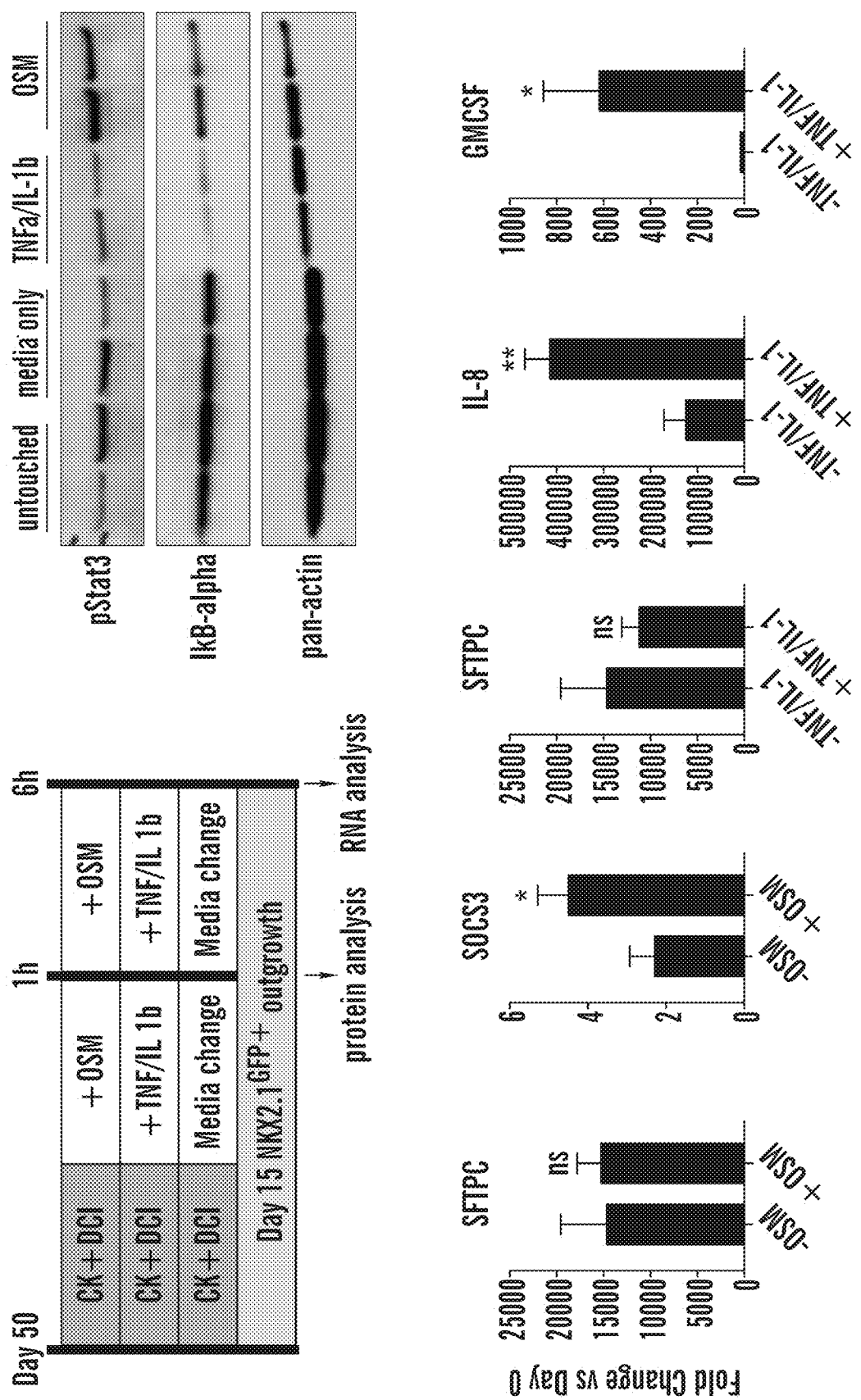

Focusing next on the gene expression differences between day 15 and day 35 Tom+ cells, GSEA revealed the JAK/STAT3/IL6 and TNFa/NFkB signaling pathways comprised the top 2 upregulated signaling pathways in the day 35 Tom+ population and were in the top 13 of all upregulated Hallmark pathways overall (FIG. 12C). To determine whether iPSC-derived day 35 cells are capable of functional signaling through these canonical pathways, PSC-derived alveolospheres were stimulated with cytokines known to activate each pathway in pulmonary epithelial cells (Quinton et al. 2007); (Quinton et al. 2008); (Traber et al. 2015): oncostatin M (OSM) for the JAK/STAT3 pathway, and TNFa/IL1b for the TNFa/NFkB pathway. Exposure to OSM ligand resulted in significant and rapid activation of STAT3 signaling, indicated by increased phosphorylated STAT3 protein and downstream SOCS3 mRNA expression, whereas exposure to TNFa and IL1b activated NFkB signaling, as evidenced by a rapid decrease in IkB protein and an increase in the expression of NFkB-dependent cytokines, IL8 and GM-CSF (FIG. 5H). Taken together, these results indicate that iAEC2s are capable of performing another important function of AEC2s: immune signaling in response to canonical ligands.

Figures 6A, 6B:
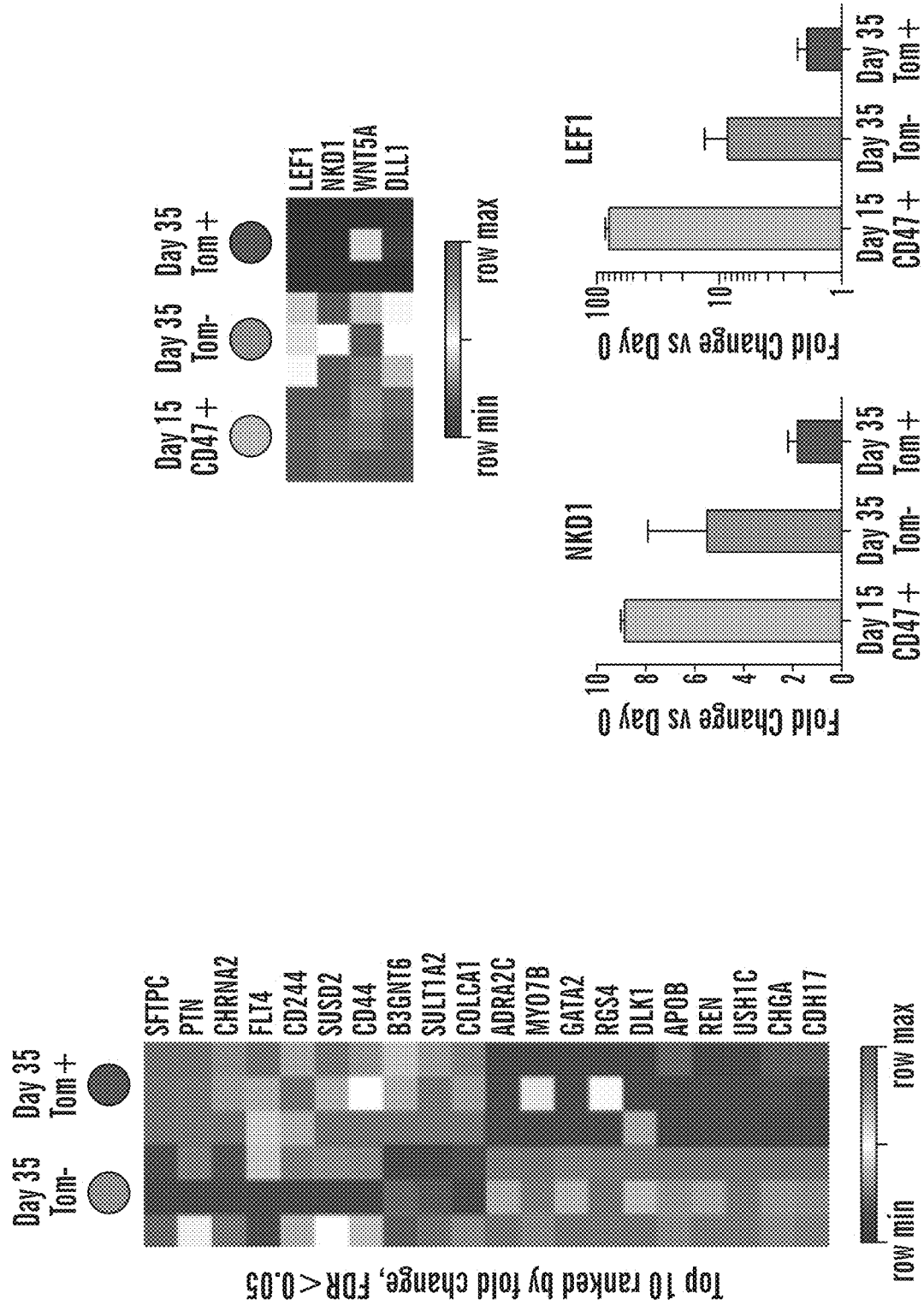
FIGS. 6A-6F demonstrate that temporal regulation of Wnt signaling promotes iAEC2 maturation and proliferation.

The few and subtle gene expression differences between PSC-derived day 35 Tom+ and Tom− cells were examined (FIG. 6A). Only 203 genes were differentially expressed between Tom+ and Tom− cells and of these only 30 were upregulated in the Tom+ population, including SFTPC (FDR≤0.05; FIG. 6A). The 173 genes downregulated in Tom+ compared to Tom− cells were enriched in transcripts encoding non-lung endodermal markers, such as hindgut marker, CDX2, stomach marker CHGA, and hepatic markers APOA2 and APOB2, implying that Tom+ sorting depleted the iAEC population of these alternative endodermal lineages. Because the global transcriptomic profiles of iPSC-derived Tom+ and Tom− cells were so similar when each population originated from sorted day 15 lung progenitors, the possibility was considered that each population was largely composed of closely related distal alveolar epithelia. Consistent with this possibility, replating each population in pure form (sorted Tom+ cells vs Tom− cells) gave rise to alveolospheres each composed of a mixture of Tom+ and Tom− cells, recreating the diversity of cells and implying a lineage relationship between the two populations.

Figure 6C:
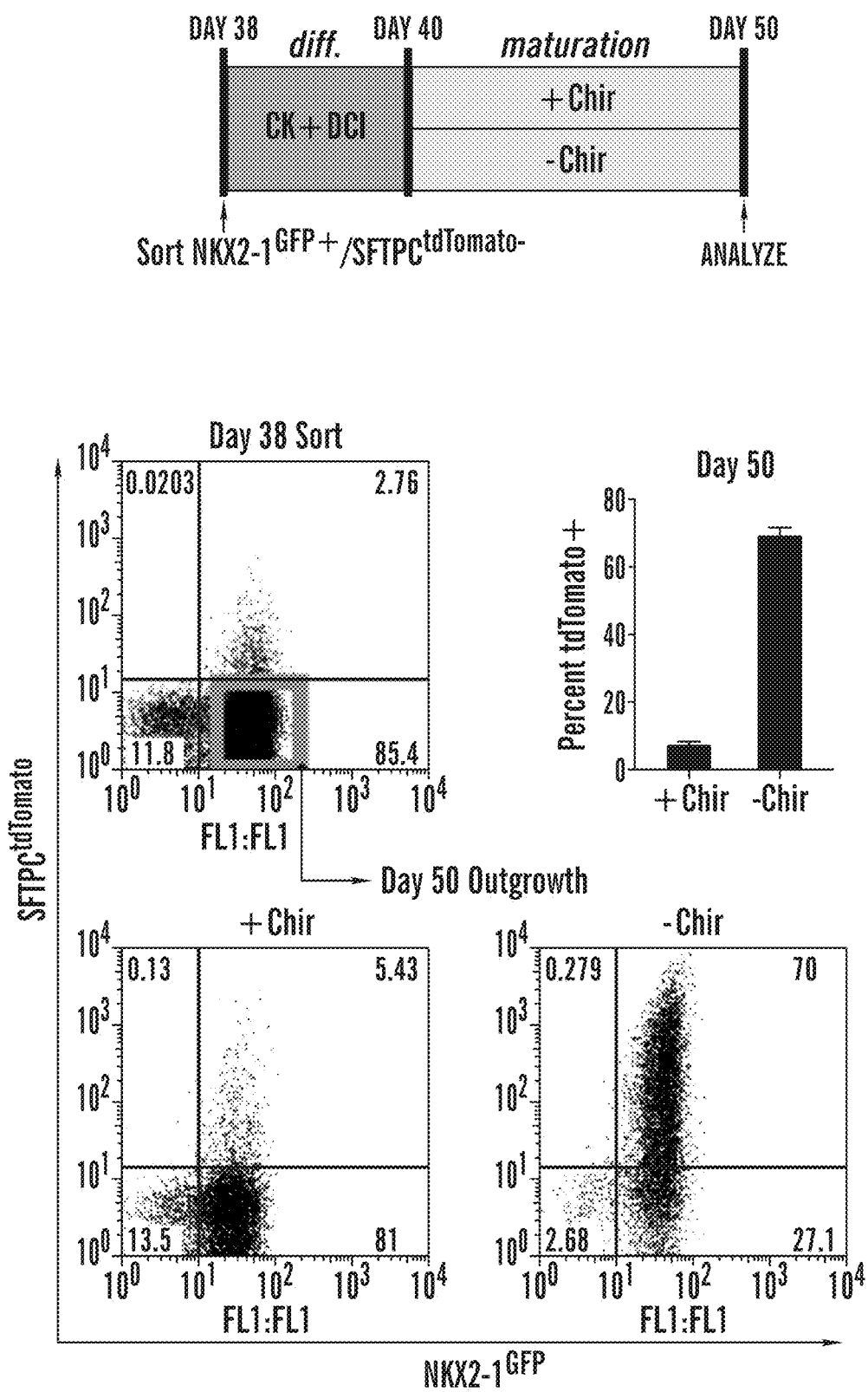
Figure 6D:
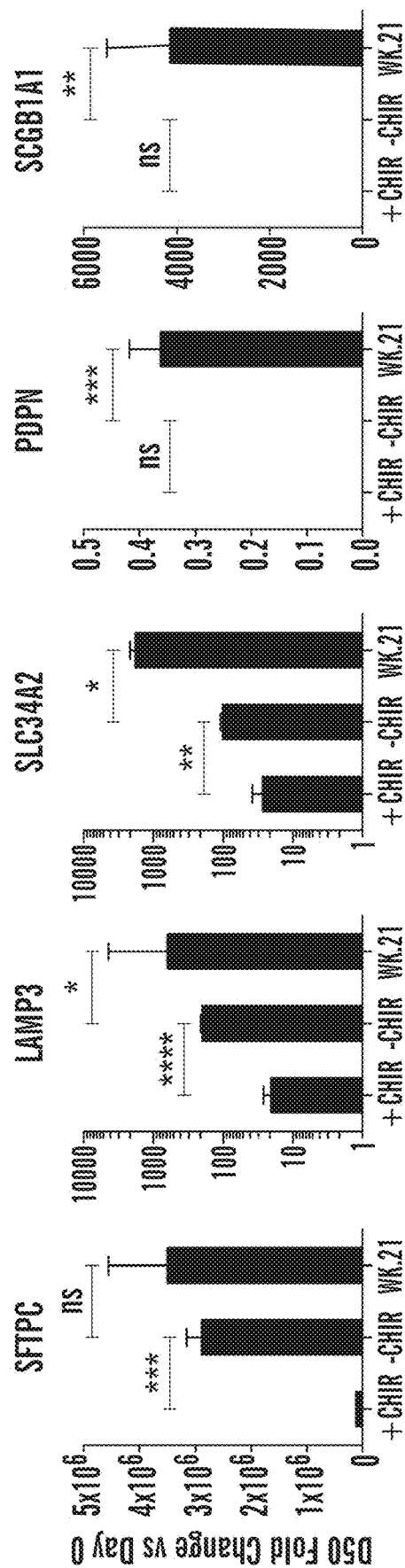

Temporal regulation of Wnt activity promotes iAEC2 maturation. Based on the significantly higher SFTPC expression in the otherwise similar Tom+vs Tom− cells on day 35, the possibility was considered that Tom+ cells might represent a more mature state of iAEC2s compared to Tom− cells. GSEA analysis to screen for developmental pathways that might distinguish the two populations revealed that Wnt signaling was the top differentially expressed developmental pathway (FIG. S12B). Although both cell populations were cultured in the presence of CHIR, Wnt signaling was unexpectedly downregulated in Tom+ cells, compared to Tom− cells, with significantly decreased expression of LEF1 and NKD1 (FIG. 6B), two Wnt targets most associated with canonical Wnt signaling levels in the PSC-lung model system (McCauley et al., in press). Hence, to test the hypothesis that decreased Wnt signaling regulates maturation of iAECs, the distalized NKX2-1GFP+/SFTPCtdTomato− population were sorted on day 38 for further 3D culture in the presence of absence of continued Wnt stimulation with CHIR (FIG. 6C). It was found that withdrawal of CHIR for 10 days (days 40-50) resulted in markedly increased efficiency of differentiation into SFTPC+ progeny (68.7%+/−2.8), with significant upregulation of SFTPC mRNA as well as other markers of AEC2 maturation, LAMP3 and SLC34A2 (FIG. 6C,6D).

Figure 6E:
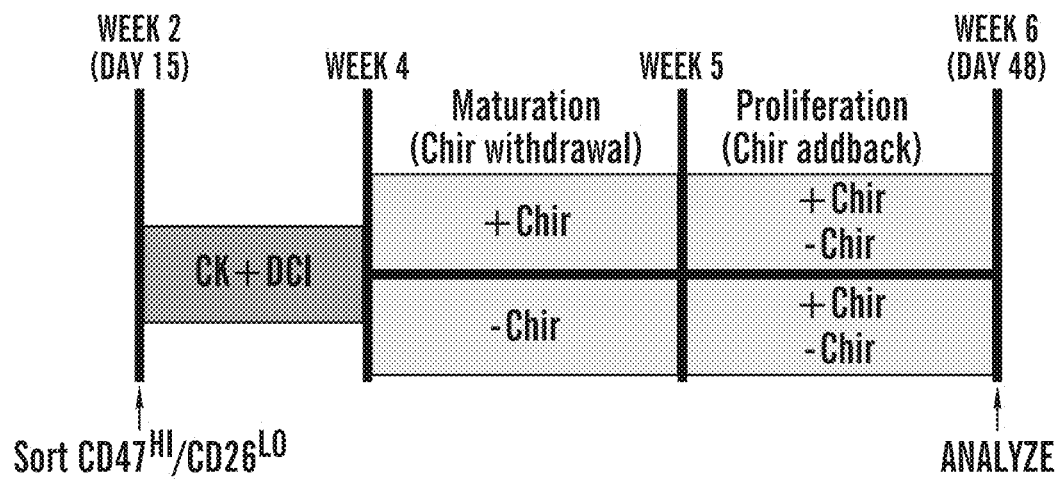
Figure 6E:
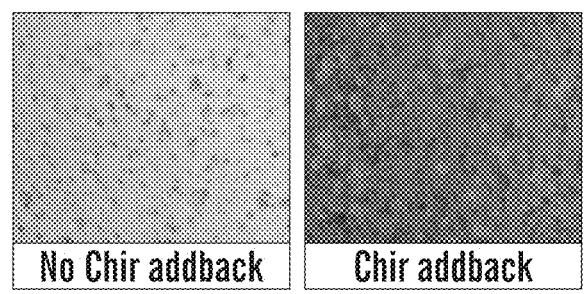
Figure 6E:
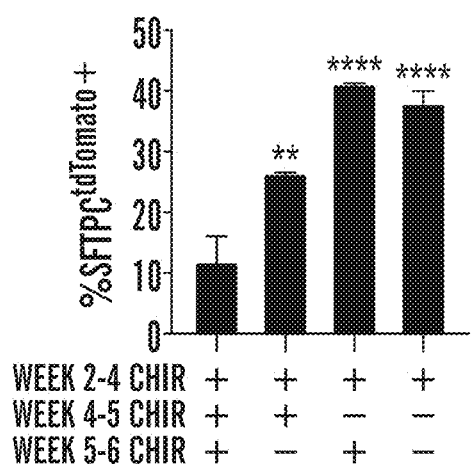
Figure 6E:
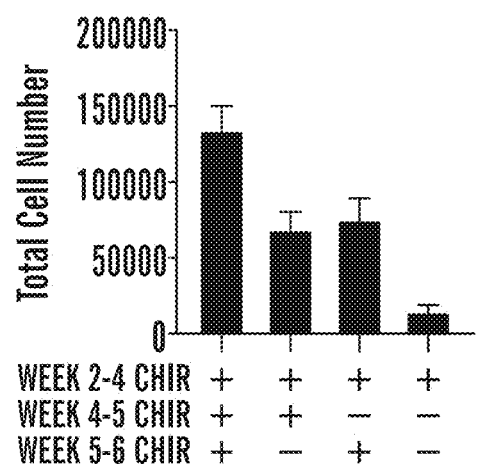
Figure 6F:
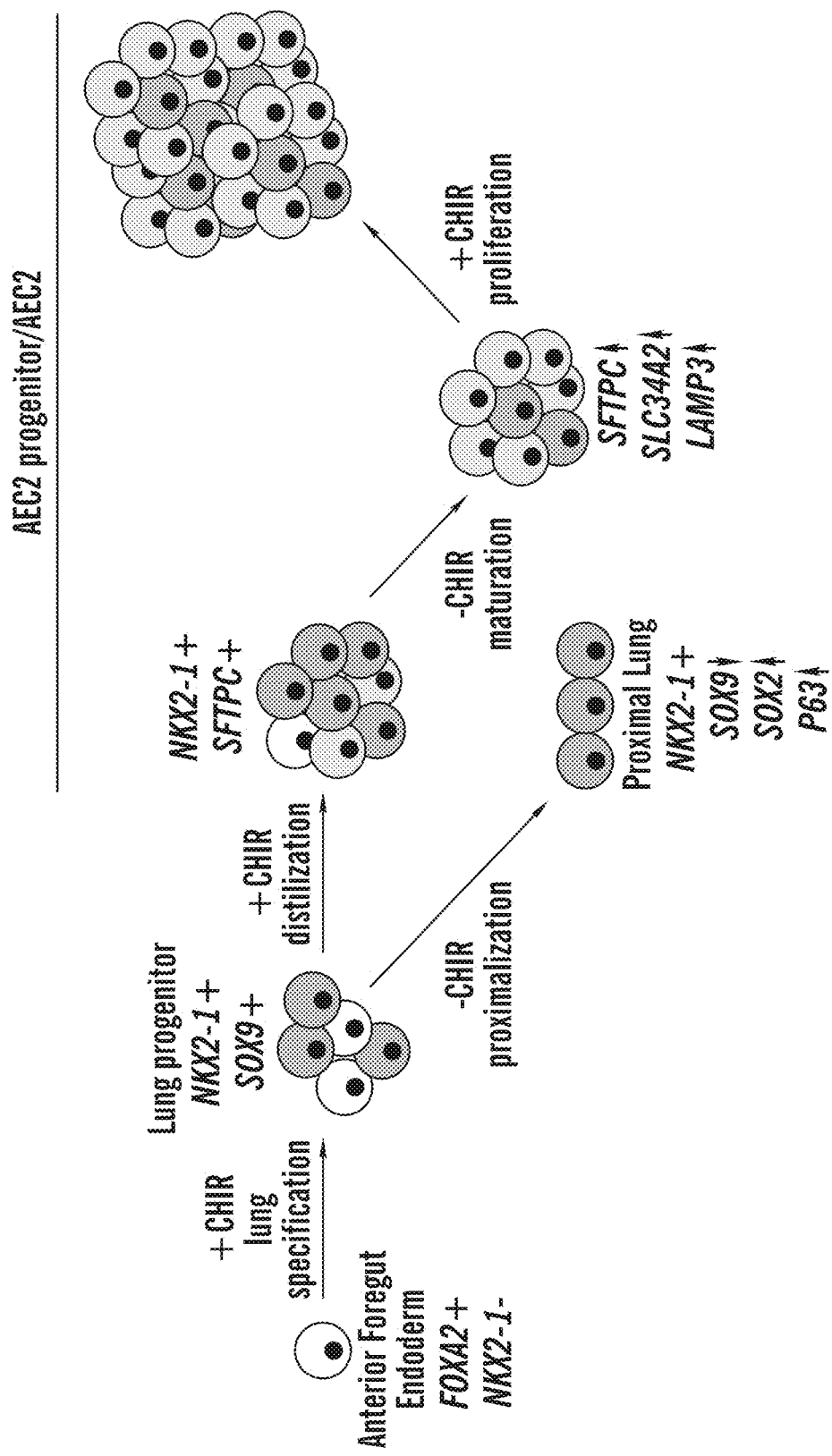
Figure 7A:
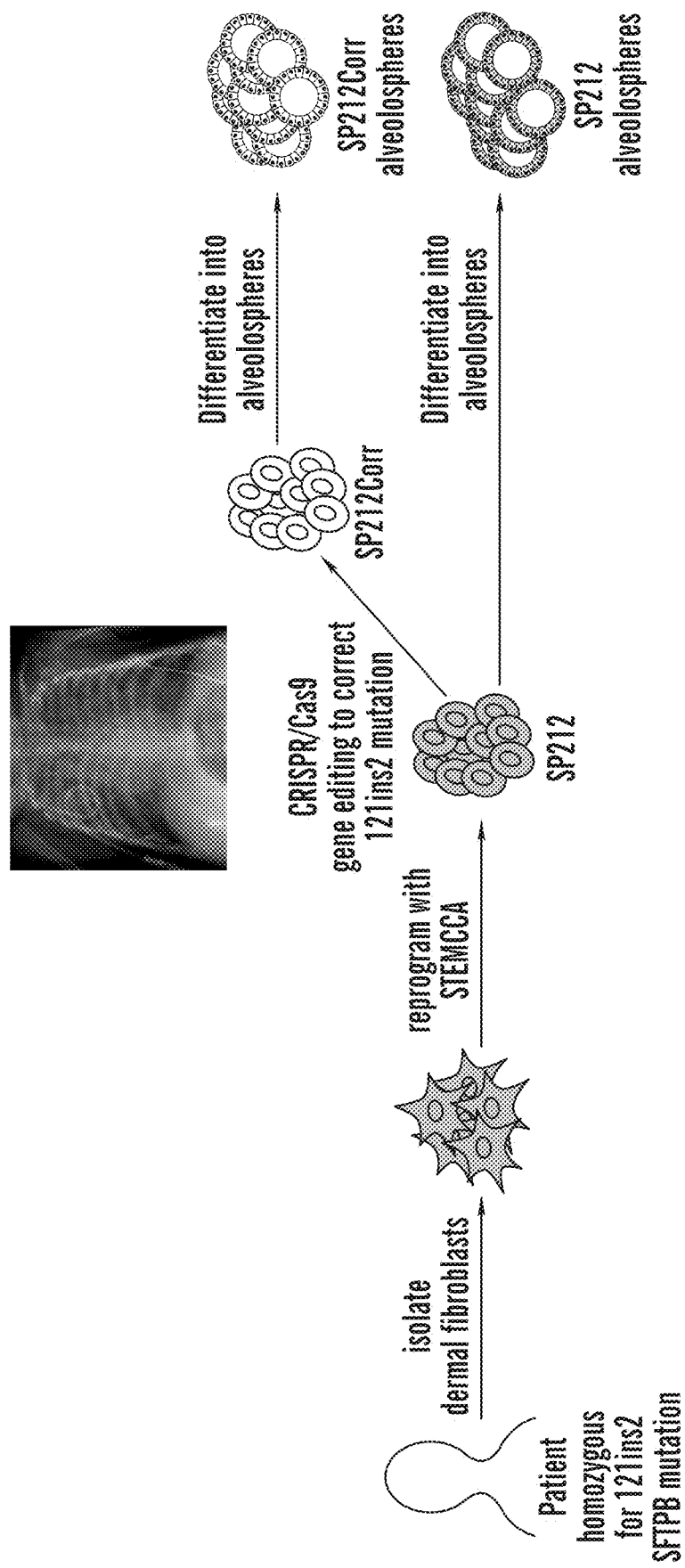
FIGS. 7A-7F demonstrate that iPSC-derived AEC2s enable in vitro modeling of genetic alveolar disease.
Figure 7B:
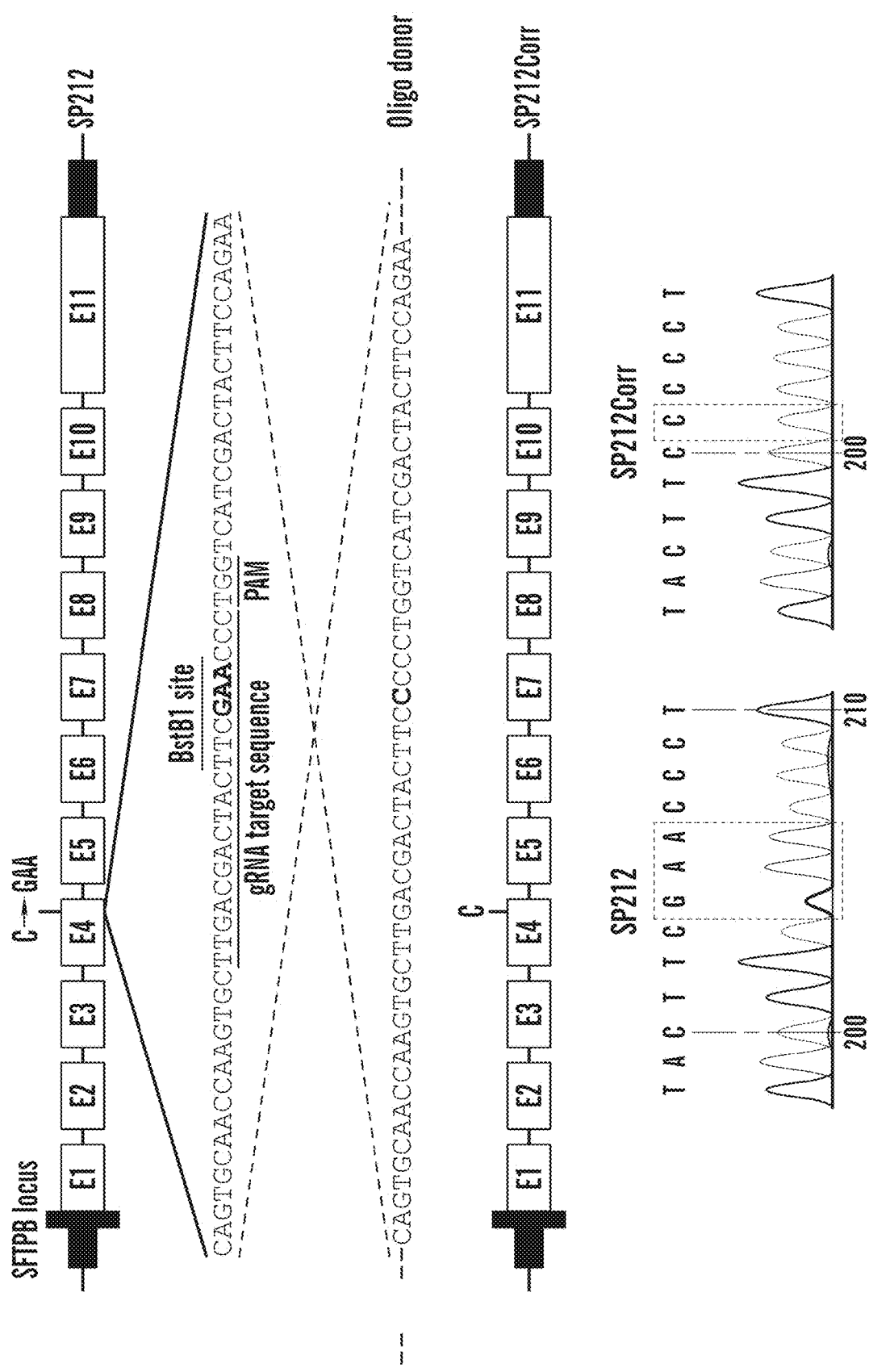
Figure 7C:
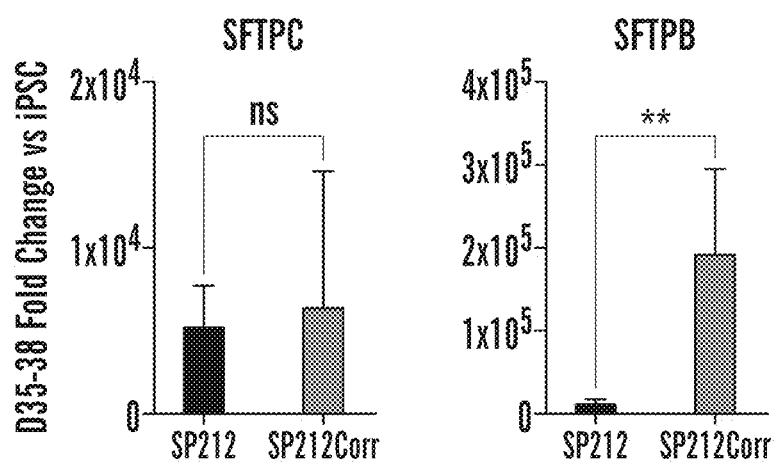
Figure 7D:
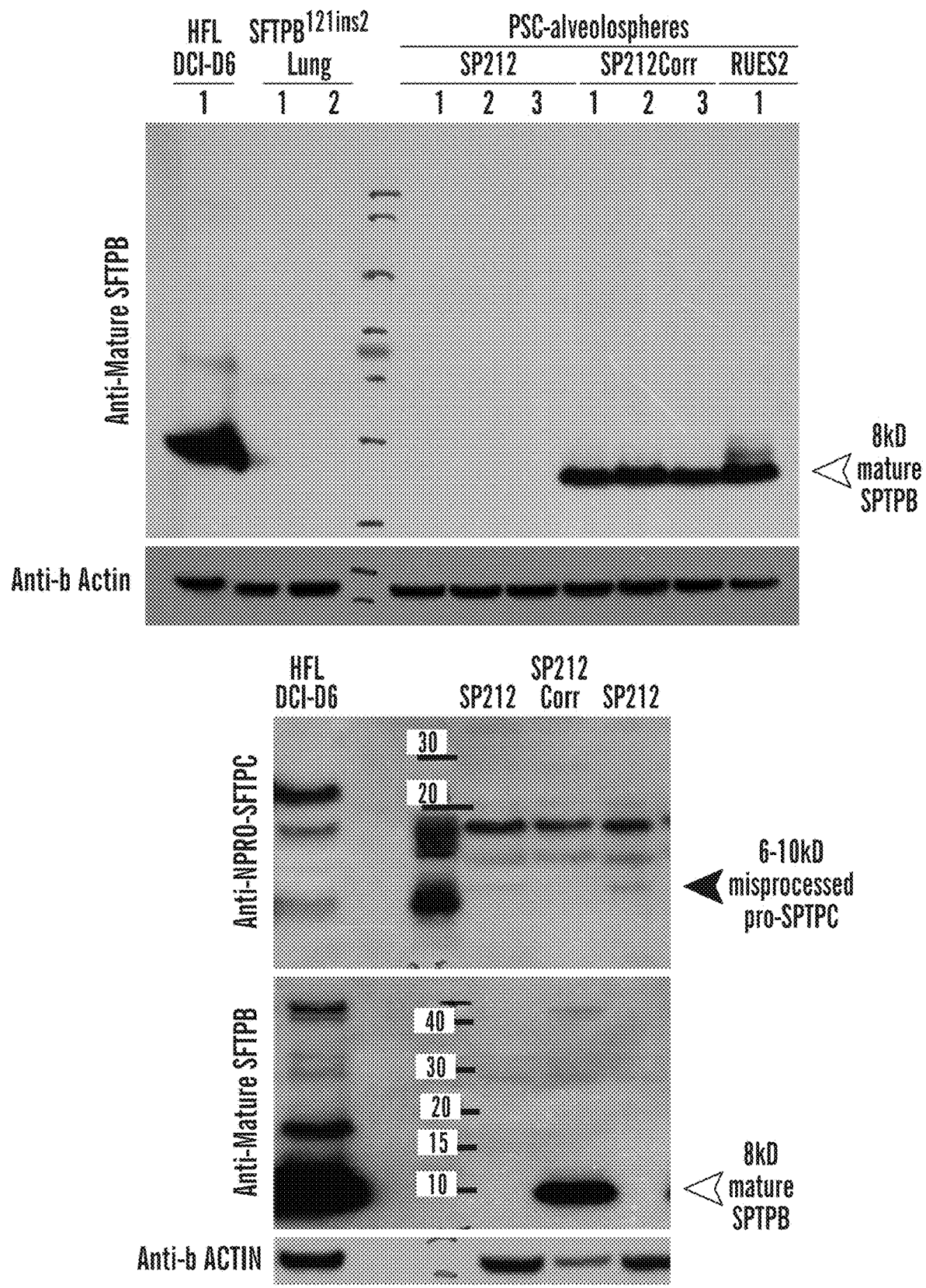
Figure 7E:
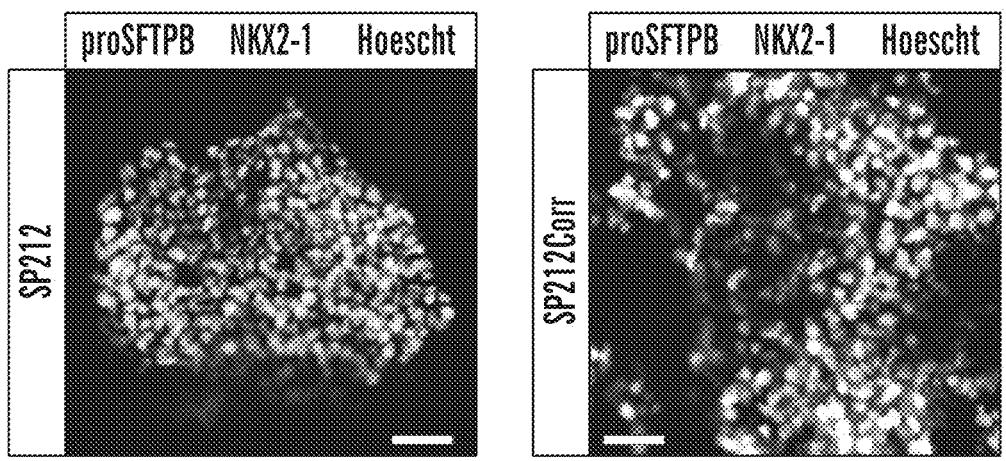
Figure 7F:
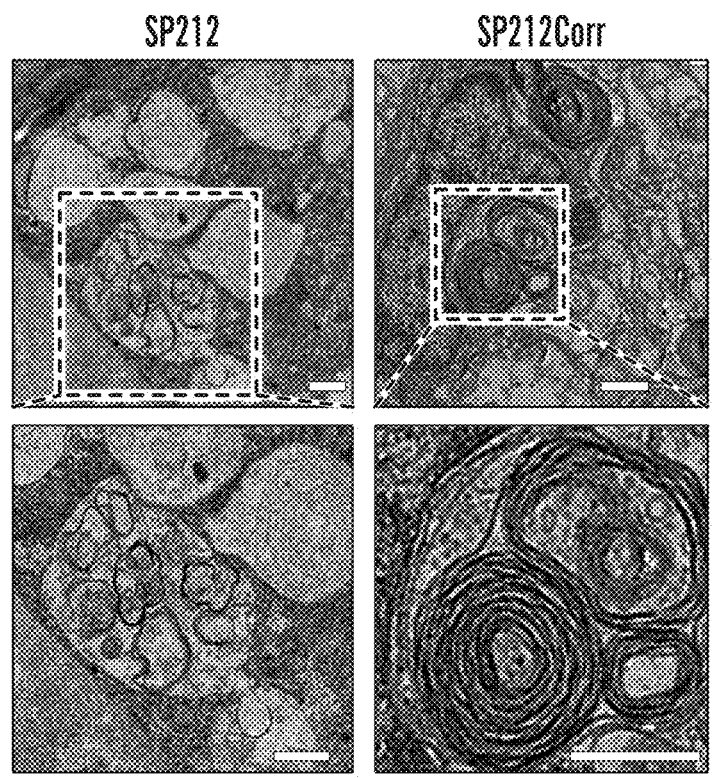
Figure 13A:
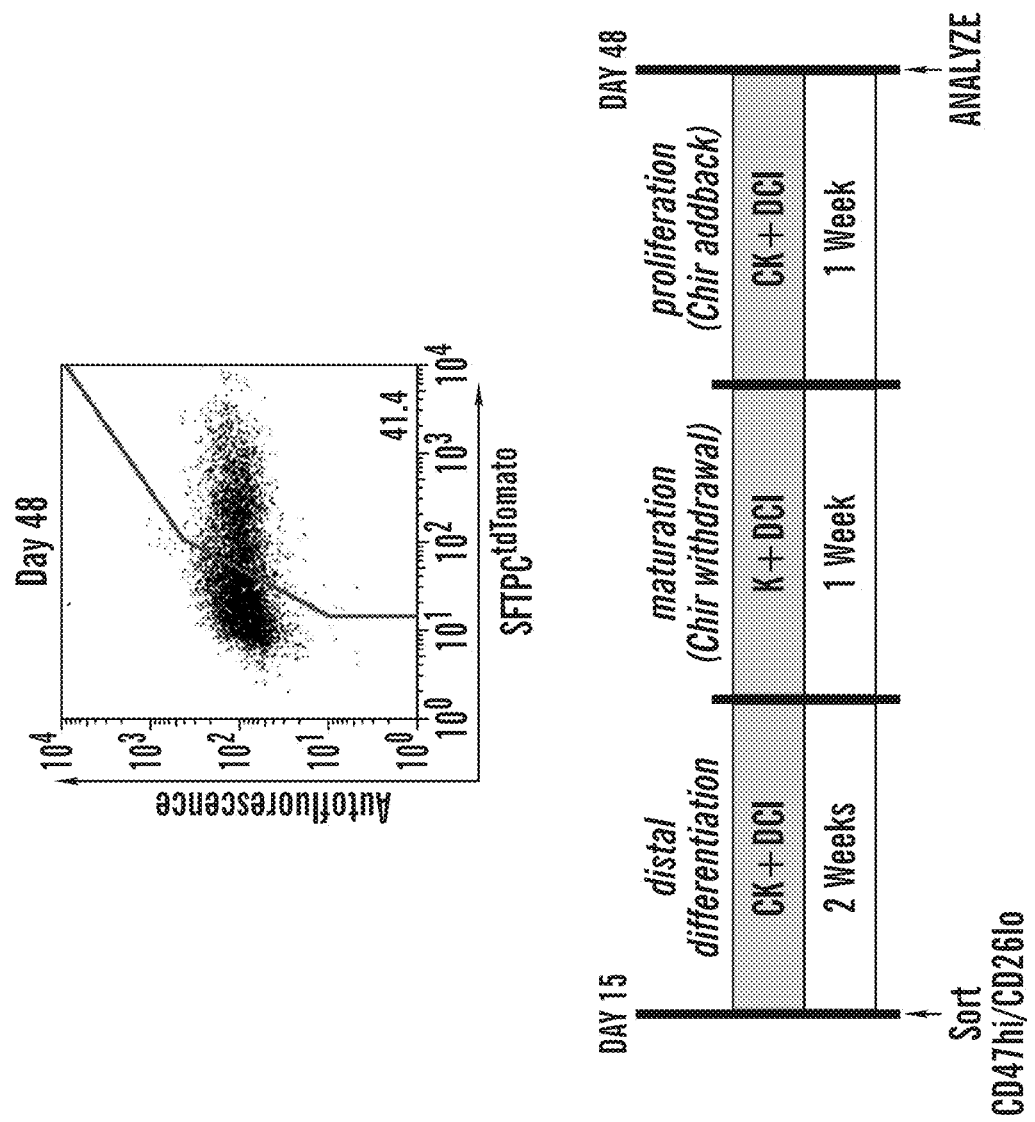
FIGS. 13A-13B depict transcript expression in whole alveolospheres after CHIR addback.
Figure 13B:
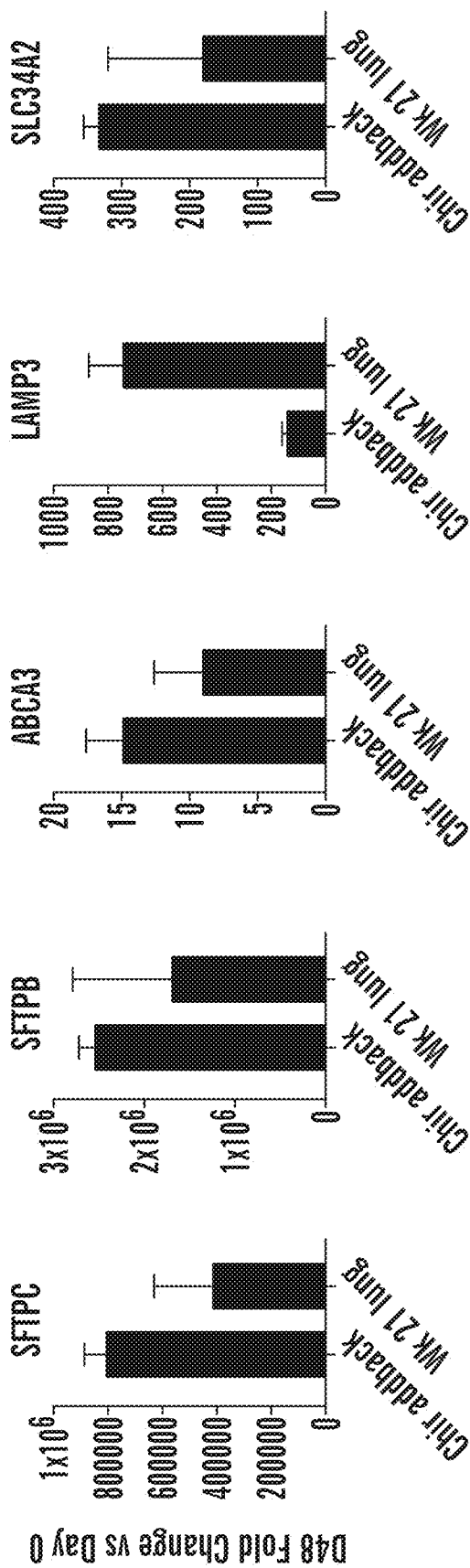
Figure 14B:
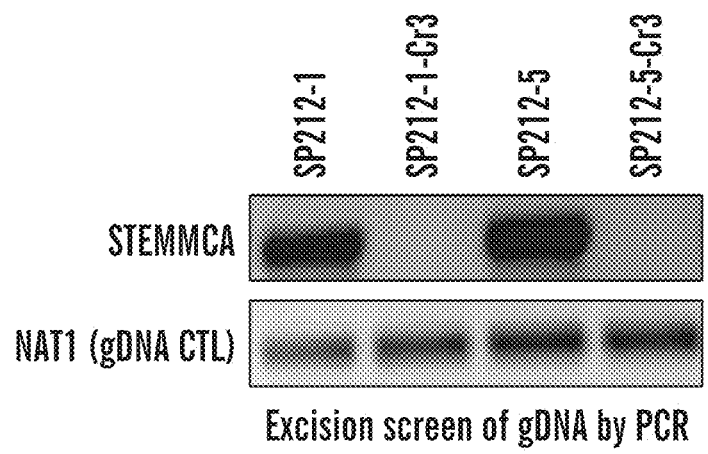
Figure 14C:
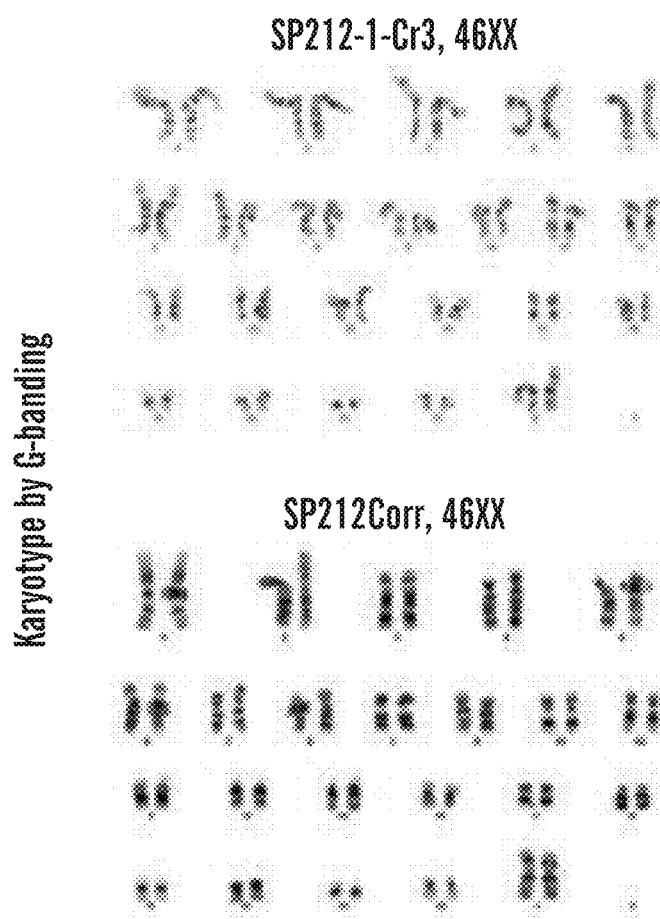
Figure 14D:
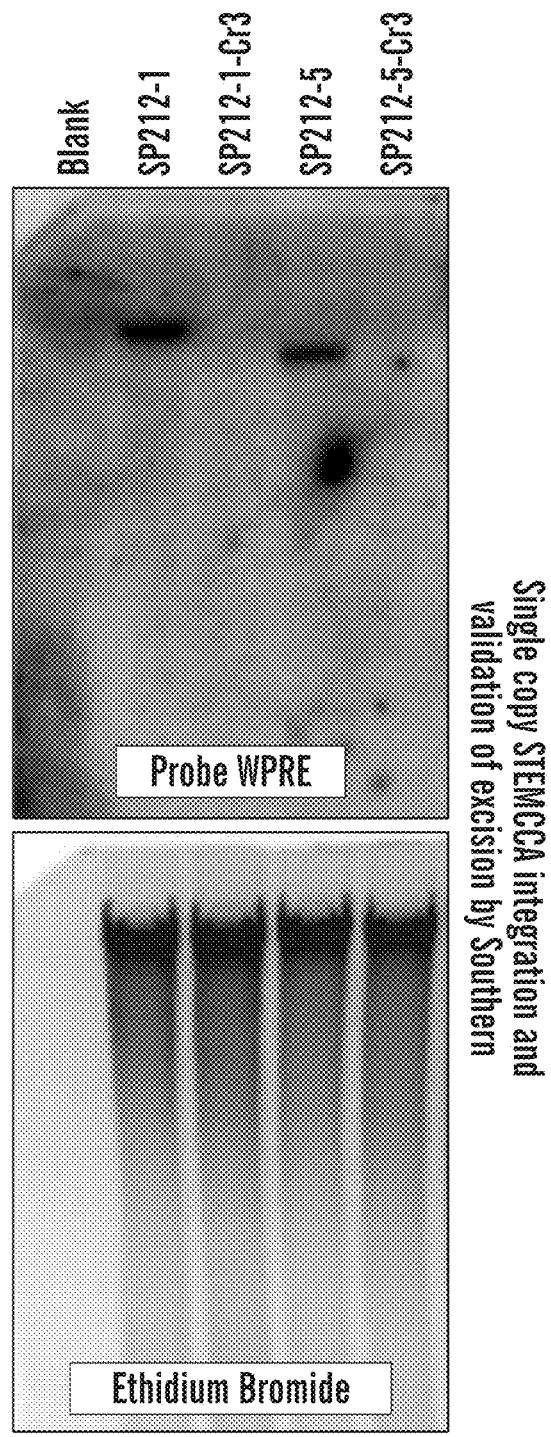
Figure 14E:
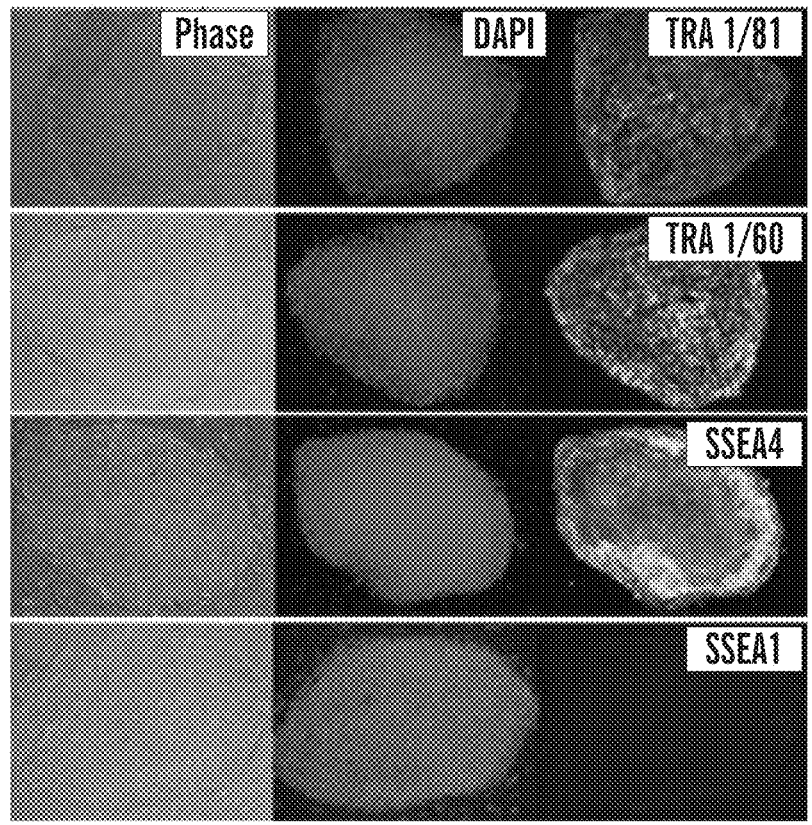

Notably, following this period of CHIR withdrawal, decreased proliferation and size of alveolospheres were observed (data not shown) and these experiments were repeated, adding back CHIR following a 1-week period of withdrawal (FIG. 6E). It was found that subsequent re-exposure to CHIR resulted in maintained expression of the SFTPCtdTomato reporter and increased proliferation, evident as increased cell numbers of the resulting SFTPC$^{tdTomato+}$ cells (FIG. 6E), findings consistent with the recently reported post-natal proliferative effects of Wnt activation in AEC2 in vivo in mouse models (Frank et al. 2016). Thus, alveolospheres (derived from sorted CD47hi/CD26lo on day 15; week 2) exposed to CK+DCI media from weeks 2-6 with CHIR withdrawn from week 4-5 and added back from week 5-6, displayed at least 40% SFTPCtdTomato+ cells and expressed high levels of alveolar transcripts SFTPC, SFTPB, ABCA3, and additional AEC2 maturation transcripts, SLC34A2 and LAMP3, with only LAMP3 being expressed at a lower level than primary (week 21) human fetal lung alveolar cell controls (FIGS. 6E and 13A-13B). Taken together, these results indicate that though Wnt stimulation is required for distal lung epithelial differentiation from primordial NKX2-1+ progenitor cells, long-term sustained Wnt stimulation may prevent these distal cells from committing to a fully mature AEC2 phenotype, and temporal modulation of Wnt signaling promotes AEC2 maturation and self-renewal.

iPSC-AEC2s enable in vitro modeling of genetic alveolar disease. Finally it was sought to derive iAEC2 from disease-specific iPSCs made from a child carrying homozygous SFTPB mutations (121ins2), a monogenic cause of neonatal respiratory distress that requires lung transplantation for survival (FIG. 7A). Based on prior work, SFTPB mutations do not perturb SFTPB locus transcription, but the unstable mutant mRNA in patients is only detectable at 8% of normal levels and carries a premature stop codon with consequent loss of detectable SFTPB protein, inability to form lamellar bodies, misprocessing of SFTPC protein, failure to synthesize or secrete surfactant, and, ultimately, neonatal respiratory distress (Nogee et al. 1994); (Beers et al. 2000). To date it has not been possible to correct the mutation in primary AEC2s from patients to definitively prove that all changes result intrinsically in human AEC2s as the direct consequence of the mutation rather than from additional or downstream secondary effects from diseased bystander cells within the lung. To develop a novel in vitro model of this disease, based on patient-specific cells, dermal fibroblasts from a patient homozygous for the 121ins2 SFTPB mutation were reprogrammed employing a single integrated copy of Cre-excisable STEMCCA-loxP lentiviral vector (Somers et al. 2010) (FIG. 14A). Following excision of the STEMCCA cassette, the resulting "transgene-free" iPSC line (SP212) underwent footprint-free correction by gene editing both mutant SFTPB alleles using CRISPR/Cas9 technology together with a short oligo donor to replace the mutant 2 bp insertion in exon 4, resulting in a corrected line with two normal SFTPB alleles (hereafter SP212Corr) (FIGS. 7B and 14B-14E). Both lines were differentiated via CD47hi/CD26lo sorted progenitors into alveolospheres expressing similar levels of SFTPC mRNA (FIG. 7C) in order to perform head-to-head comparisons of the pre- vs post-gene corrected cells (SP212 vs SP212Corr). It was observed that SP212 alveolospheres expressed lower levels of SFTPB transcript than SP212Corr alveolospheres (FIG. 7C), no detectable SFTPB protein, and no detectable lamellar bodies by TEM (FIGS. 7D-7F). Notably, in 2/3 differentiations, we observed the appearance of an aberrant, misprocessed 6-10 kD proSFTPC protein form in SP212 alveolospheres, a form resulting from the residual N terminal flanking dodecapeptide that cannot be cleaved from proSFTPC in the absence of lamellar bodies (FIG. 7F). In SP212Corr alveolospheres, correction of the SFTPB mutation resulted in increased SFTPB mRNA, the appearance of detectable lamellar bodies, reconstitution of the mature 8kD form of SFTPB protein, and disappearance of the aberrant proSFTPC protein form, verifying that all deficiencies were the direct result of the SFTPB121ins2 mutation (FIGS. 7C-7F).

Discussion

The results described herein demonstrate the differentiation of phenotypically mature AEC2-like cells, referred to as iAEC2s, from human ESCs as well as from patient-specific iPSCs. Formed in 3D cultures via an NKX2-1+ endodermal lung progenitor intermediate, the resulting cells express distal lung alveolar epithelial mRNAs and proteins, as well as functional lamellar bodies that process, store, and secrete surfactant. Contrary to prior reports of the necessity of feeder cells for culturing primary adult AEC2s, we were able to derive and serially passage "epithelial-only" alveolospheres without using mesenchymal feeders, differentiating populations of sorted NKX2-1+ primordial progenitors into alveolar cells. It was found that the emergence of SFTPC+ cells from NKX2-1+ precursors in culture occurred rapidly in the presence of Wnt stimulation via CHIR within 2-7 days (17-22 total differentiation days) and was augmented by the additional presence of stimulants of FGF signaling together with corticosteroids and cyclic AMP ("DCI media"). It was also found that the early-stage iPSC-derived NKX2-1+ cells represented the entire progenitor pool from which SFTPC+ cells are later derived, consistent with mouse developmental studies (Minoo 1999) and further validating our recently published human directed differentiation findings (Hawkins et al).

Though lamellated inclusions were observed in the cytoplasm of alveolospheres, lamellated inclusions that are not enriched in surfactant proteins or phospholipid can be mistakenly referred to as AEC2 lamellar bodies, and they have been known to occur in a variety of cell types that neither display an AEC2 phenotype nor package surfactant in culture, such as A549 cells (Mason & Williams 1980). Only phenotypically mature pulmonary AEC2s are known to have true lamellar bodies enriched in surfactant. Based on their functional capacity to process SFTPB protein to its 8kD isoform and produce DPPC surfactant phospholipid, it was concluded that iAEC2s express true lamellar bodies and represent a maturity level comparable to primary AEC2s post-week 24 of gestation, a benchmark that has not been demonstrated before in reports of in vitro alveolar directed differentiation. PSC-derived alveolospheres were found to be composed of a mixture of lung epithelial cells, likely of varying states of maturity. Despite the presence of a subset of relatively mature cells, the unsorted alveolospheres as well as their sorted SFTPC high or low components can be sequentially passaged and maintain proliferative capacity over weeks to months. Though AEC1 markers were not generally detected within 3D alveolospheres, when $SFTPC^{tdTomato+}$ iAEC2s are plated in 2D culture they down-regulated SFTPC and upregulated the AEC1 markers PDPN and AGER, as has been shown in primary AEC2 culture. These capacities of self-renewal and differentiation are key features that have defined primary AEC2 in vivo as the progenitors of the distal lung and are required for the survival of air breathing mammals.

On a whole transcriptome level, iAEC2s clustered closer to cultured primary fetal AECs than to adult or fetal AEC2s. Although iAEC2s are more similar to adult AEC2 when compared based on supervised hierarchical clustering using AEC2 specific gene sets, still these similarities should not be overstated. Not surprisingly there are many ways in which iAEC2s, differentiated in submerged culture over only 30-35 days in vitro are not identical to primary AEC2s exposed to a lifetime of air breathing in adults. Several of the gene sets enriched in primary adult AEC2s compared to iAEC2s appeared to involve immune responses and oxidant stress pathways, and it is expected that these transcriptomic networks would be underrepresented in iAEC2s. However, it was found that iAECs treated with immune cytokines do respond by activating the IL6/JAK/STAT3 and TNF/NFkB pathways. Since AEC2s are known to be important immune modulators in vivo, it is important that iAEC2s allow for studies of immune function.

Though we were surprised to find that $SFTPC^{tdTomato+}$ and $SFTPC^{tdTomato-}$ cells cluster so closely together by PCA as well as supervised hierarchical clustering analyses, it is likely that these populations, both deriving from NKX2-1+ lung endoderm in distalizing conditions, represent very similar cells, some of which have progressed to express high levels of SFTPC and others which may remain "stuck" as less mature cell types expressing significantly lower levels of SFTPC, even though most other AEC2-specific genes are expressed similarly in both populations. Though robust evidence of increased expression of AEC1 or proximal lung epithelial markers were not seen in the $SFTPC^{tdTomato-}$ cells, expression of markers of the gut, liver, and stomach were seen, suggesting that there are also some non-lung cells present in the SFTPC negative population. Since NKX2-1+/SFTPC− cells at a late timepoint in differentiation are still capable of maturation into SFTPC+ cells, there is likely still fluidity between SFTPC-expressing and non-expressing states, and there may be a higher percent of lower SFTPC-expressing AEC2-like cells in the NKX2-1+ population than the $SFTPC^{tdTomato}$ reporter indicates at any given time.

Interestingly, GSEA analysis showed that the Wnt/bCatenin signaling pathway was downregulated in $SFTPC^{tdTomato+}$ cells, and late CHIR withdrawal resulted in both a dramatic increase in percent $SFTPC^{tdTomato+}$ cells in the previously $SFTPC^{tdTomato-}$ population and an increase in expression of mature AEC2 transcripts within this population. This finding indicates that overstimulation with CHIR can actually inhibit full alveolar differentiation. Early CHIR withdrawal (Day 15) results in proximalization of NKX2-1+ lung progenitors (McCauley et al., in press), and as demonstrated herein late withdrawal of CHIR, following distalization, promotes alveolar differentiation, consistent with the low-Wnt pre-alveologenesis stage of AEC2 development recently reported in mice by Frank and colleagues (Frank et al. 2016). Furthermore, as predicted by these mouse studies, adding back Wnt stimulation following maturation stimulates proliferation of the resulting human iAEC2s.

Finally, the ultimate test of iAEC2s as a clinically relevant surrogate for primary AEC2s is whether they can recapitulate human alveolar disease in vitro. Primary cells from patients with alveolar disease are difficult to access and do not proliferate well in culture, severely limiting studies into the pathogenesis of these diseases. Despite this, the pathogenesis of SFTPB deficiency has been documented as resulting in unstable SFTPB mRNA, lack of production of SFTPB protein and lamellar body agenesis (Nogee et al. 1993); (Beers et al. 2000). Indeed, herein, iAEC2s generated from a child with severe lung disease due to homozygous 121ins2 SFTPB mutations recapitulated known aspects of this disease, which were rescued in gene-corrected iAEC2s from the same patient. This finding shows that iAEC2s can provide a robust model for human alveolar disease that avoids the issues of patient access and safety, the low proliferative capacity of primary AEC2s, and the barriers to efficient gene editing of primary cells. Now, 24 years after Nogee et al.'s original report of two brothers with neonatal respiratory distress and SFTPB deficiency suggestive of a genetic cause of the disease (Nogee et al. 1994), patient-specific iAEC2s and their gene-corrected progeny provide a sophisticated in vitro disease model, carrying each patient's own genetic background. This new model both recapitulates the original observations, demonstrates their reversal with gene editing technologies, and now facilitates delineation of the disease-causing mechanisms previously studied by our community using heterologous systems and mouse genetic models (Clark et al. 1995; Melton et al. 2003). Thus the work described herein shows generation of phenotypically mature iPSC-derived alveolar organoids that represent a robust in vitro model of both human alveolar development and disease, providing a platform by which new insights can be made into the effects of genetic and environmental insults on AEC2 biology.

REFERENCES

Ballard, P. L. et al., 2010. Regulated gene expression in cultured type II cells of adult human lung. American journal of physiology. Lung cellular and molecular physiology, 299(1), pp. L36-50.

Barkauskas, C. E. et al., 2013. Type 2 alveolar cells are stem cells in adult lung. The Journal of Clinical Investigation, 123(123(7)), pp. 3025-3036.

Beers, M. F., Bates, S. R. & Fisher, A. B., 1992. Differential extraction for the rapid purification of bovine surfactant protein B. The American journal of physiology, 262(6 Pt 1), pp. L773-8.

Beers, M. F. et al., 1994. Localization, synthesis, and processing of surfactant protein SP-C in rat lung analyzed by epitope-specific antipeptide antibodies. The Journal of biological chemistry, 269(32), pp. 20318-20328.

Beers, M. F. et al., 2000. Pulmonary surfactant metabolism in infants lacking surfactant protein B. American journal of respiratory cell and molecular biology, 22(3), pp. 380-391.

Boggaram, V., 2009. Thyroid transcription factor-1 (TTF-1/Nkx2.1/TITF1) gene regulation in the lung. Clinical Science, 116(1), pp. 27-35.

Borok, Z. et al., 1998. Modulation of t1alpha expression with alveolar epithelial cell phenotype in vitro. The American journal of physiology, 275(1 Pt 1), pp. L155-64.

Brasch, F. et al., 2004. Surfactant protein B in type II pneumocytes and intra-alveolar surfactant forms of human lungs. American journal of respiratory cell and molecular biology, 30(4), pp. 449-458.

Clark, J. C. et al., 1995. Targeted disruption of the surfactant protein B gene disrupts surfactant homeostasis, causing respiratory failure in newborn mice. Proceedings of the National Academy of Sciences of the United States of America, 92(17), pp. 7794-7798.

Crane, A. et al., 2015. Targeted correction and restored function of the CFTR gene in cystic fibrosis induced pluripotent stem cells. Stem Cell Reports, 4(4), pp. 569-577.

Desai, T. J., Brownfield, D. G. & Krasnow, M. A., 2014. Alveolar progenitor and stem cells in lung development, renewal and cancer. Nature, pp. 1-16.

Dobbs, L. G., Williams, M. C. & Gonzalez, R., 1988. Monoclonal antibodies specific to apical surfaces of rat alveolar type I cells bind to surfaces of cultured, but not freshly isolated, type II cells. Biochimica et biophysica acta, 970(2), pp. 146-156.

Dobin, A. et al., 2013. STAR: ultrafast universal RNA-seq aligner. Bioinformatics (Oxford, England), 29(1), pp. 15-21.

Dye, B. R. et al., 2015. In vitro generation of human pluripotent stem cell derived lung organoids. eLife, 4, p. 1999.

Foster, C. et al., 2004. Pepsinogen C: a type 2 cell-specific protease. American journal of physiology. Lung cellular and molecular physiology, 286(2), pp. L382-7.

Foster, C. D. et al., 2007. In Vitro Transdifferentiation of Human Fetal Type II Cells Toward a Type 1-like Cell. Pediatric Research, 61(4), pp. 404-409.

Frank, D. B. et al., 2016. Emergence of a Wave of Wnt Signaling that Regulates Lung Alveologenesis by Controlling Epithelial Self-Renewal and Differentiation. Cell-Reports, 17(9), pp. 2312-2325.

Gonzales, L. W. et al., 2002. Differentiation of human pulmonary type II cells in vitro by glucocorticoid plus cAMP. American journal of physiology. Lung cellular and molecular physiology, 283(5), pp. L940-51.

Gotoh, S. et al., 2014. Generation of Alveolar Epithelial Spheroids via Isolated Progenitor Cells from Human Pluripotent Stem Cells. Stem cell reports, 3(3), pp. 394-403.

Guttentag, S. H. et al., 1998. Surfactant protein B processing in human fetal lung. The American journal of physiology, 275(3 Pt 1), pp. L559-66.

Have-Opbroek, Ten, A. A., Otto-Verberne, C. J. & Dubbeldam, J. A., 1990. Ultrastructural characteristics of inclusion bodies of type II cells in late embryonic mouse lung. Anatomy and embryology, 181(4), pp. 317-323.

Hawkins et al. 2017 Prosepective isolation of NKX2-expressing human lung progenitors derived from pluripotent stem cells. JCI 127:2277-2294.

Huang, S. X. L. et al., 2013. efficient generation of lung and airway epithelial cells from human pluripotent stem cells. Nature biotechnology, 32(1), pp. 84-91.

Juers, J. A. et al., 1976. Enhancement of bactericidal capacity of alveolar macrophages by human alveolar lining material. The Journal of Clinical Investigation, 58(2), pp. 271-275.

Kalina, M., Mason, R. J. & Shannon, J. M., 1992. Surfactant protein C is expressed in alveolar type II cells but not in Clara cells of rat lung. American journal of respiratory cell and molecular biology, 6(6), pp. 594-600.

Khoor, A. et al., 1994. Temporal-spatial distribution of SP-B and SP-C proteins and mRNAs in developing respiratory epithelium of human lung. The journal of histochemistry and cytochemistry: official journal of the Histochemistry Society, 42(9), pp. 1187-1199.

Kikkawa, Y. et al., 1975. The type II epithelial cells of the lung. II. Chemical composition and phospholipid synthesis. Laboratory investigation; a journal of technical methods and pathology, 32(3), pp. 295-302.

Korimilli, A., Gonzales, L. W. & Guttentag, S. H., 2000. Intracellular localization of processing events in human surfactant protein B biosynthesis. The Journal of biological chemistry, 275(12), pp. 8672-8679.

Kurmann, A. A. et al., 2015. Regeneration of Thyroid Function by Transplantation of Differentiated Pluripotent Stem Cells. Cell stem cell, 17(5), pp. 527-542.

Law, C. W. et al., 2014. voom: Precision weights unlock linear model analysis tools for RNA-seq read counts. Genome biology, 15(2), p. R29.

Lawson, W. E. et al., 2005. Increased and prolonged pulmonary fibrosis in surfactant protein C-deficient mice following intratracheal bleomycin. The American journal of pathology, 167(5), pp. 1267-1277.

Lin, S. et al., 1996. Structural requirements for targeting of surfactant protein B (SP-B) to secretory granules in vitro and in vivo. The Journal of biological chemistry, 271(33), pp. 19689-19695.

Liu, Y. & Hogan, B. L. M., 2002. Differential gene expression in the distal tip endoderm of the embryonic mouse lung. Gene expression patterns: GEP, 2(3-4), pp. 229-233.

Mason, R. J. & Williams, M. C., 1980. Phospholipid composition and ultrastructure of A549 cells and other cultured pulmonary epithelial cells of presumed type II cell origin. Biochimica et biophysica acta, 617(1), pp. 36-50.

Mason, R. J. & Williams, M. C., 1977. Type II alveolar cell. Defender of the alveolus. The American review of respiratory disease, 115(6 Pt 2), pp. 81-91.

Mayhew, T. M., 2011. Quantifying immunogold localization on electron microscopic thin sections: a compendium of new approaches for plant cell biologists. Journal of experimental botany, 62(12), pp. 4101-4113.

Melton, K. R. et al., 2003. SP-B deficiency causes respiratory failure in adult mice. American journal of physiology. Lung cellular and molecular physiology, 285(3), pp. L543-9.

Minoo, P. E. A., 1999. Defects in Tracheoesophageal and Lung Morphogenesis in Nkx2.1(−/−) Mouse Embryos. pp. 1-12.

Mucenski, M. L. et al., 2005. Beta-catenin regulates differentiation of respiratory epithelial cells in vivo. American journal of physiology. Lung cellular and molecular physiology, 289(6), pp. L971-9.

Mulugeta, S., Nureki, S.-I. & Beers, M. F., 2015. Lost after translation: insights from pulmonary surfactant for understanding the role of alveolar epithelial dysfunction and cellular quality control in fibrotic lung disease. American journal of physiology. Lung cellular and molecular physiology, 309(6), pp. L507-25.

Nogee, L. M. et al., 1994. A mutation in the surfactant protein B gene responsible for fatal neonatal respiratory disease in multiple kindreds. The Journal of Clinical Investigation, 93(4), pp. 1860-1863.

Nogee, L. M. et al., 1993. Brief report: deficiency of pulmonary surfactant protein B in congenital alveolar proteinosis. The New England journal of medicine, 328 (6), pp. 406-410.

O'Brien, A. D. et al., 1998. Chemotaxis of alveolar macrophages in response to signals derived from alveolar epithelial cells. The Journal of laboratory and clinical medicine, 131(5), pp. 417-424.

Otto-Verberne, C. J. et al., 1988. Detection of the type II cell or its precursor before week 20 of human gestation, using antibodies against surfactant-associated proteins. Anatomy and embryology, 178(1), pp. 29-39.

Quinton, L. J. et al., 2008. Alveolar Epithelial STAT3, IL-6 Family Cytokines, and Host Defense during *Escherichia coli* Pneumonia. American journal of respiratory cell and molecular biology, 38(6), pp. 699-706.

Quinton, L. J. et al., 2007. Functions and regulation of NF-kappaB RelA during pneumococcal pneumonia. The Journal of Immunology, 178(3), pp. 1896-1903.

Rankin, S. A. et al., 2016. A Retinoic Acid-Hedgehog Cascade Coordinates Mesoderm-Inducing Signals and Endoderm Competence during Lung Specification. CellReports, 16(1), pp. 66-78.

Ridsdale, R. & Post, M., 2004. Surfactant lipid synthesis and lamellar body formation in glycogen-laden type II cells. American journal of physiology. Lung cellular and molecular physiology, 287(4), pp. L743-51.

Ridsdale, R. et al., 2011. Comparative proteomic analysis of lung lamellar bodies and lysosome-related organelles. PLoS ONE, 6(1), p. e16482.

Ross, G. F. et al., 1999. Surfactant protein C in fetal and ventilated preterm rabbit lungs. The American journal of physiology, 277(6 Pt 1), pp. L1104-8.

Shu, W. et al., 2005. Wnt/beta-catenin signaling acts upstream of N-myc, BMP4, and FGF signaling to regulate proximal-distal patterning in the lung. Developmental biology, 283(1), pp. 226-239.

Somers, A. et al., 2010. Generation of transgene-free lung disease-specific human induced pluripotent stem cells using a single excisable lentiviral stem cell cassette. Stem Cells, 28(10), pp. 1728-1740.

Sorokin, S. P., 1966. A morphologic and cytochemical study on the great alveolar cell. The journal of histochemistry and cytochemistry: official journal of the Histochemistry Society, 14(12), pp. 884-897.

Traber, K. E. et al., 2015. Induction of STAT3-Dependent CXCL5 Expression and Neutrophil Recruitment by Oncostatin-M during Pneumonia. American journal of respiratory cell and molecular biology, 53(4), pp. 479-488.

van Moorsel, C. H. M. et al., 2010. Surfactant Protein C Mutations Are the Basis of a Significant Portion of Adult Familial Pulmonary Fibrosis in a Dutch Cohort. American journal of respiratory and critical care medicine, 182(11), pp. 1419-1425.

Wade, K. C. et al., 2006. Gene Induction during Differentiation of Human Pulmonary Type II Cells In Vitro. American journal of respiratory cell and molecular biology, 34(6), pp. 727-737.

Wert, S. E. et al., 1993. Transcriptional elements from the human SP-C gene direct expression in the primordial respiratory epithelium of transgenic mice. Developmental biology, 156(2), pp. 426-443.

Whitsett, J. A., Wert, S. E. & Weaver, T. E., 2015. Diseases of Pulmonary Surfactant Homeostasis. Annual Review of Pathology: Mechanisms of Disease, 10(1), pp. 371-393.

Williams, M. C. & Mason, R. J., 1977. Development of the type II cell in the fetal rat lung. The American review of respiratory disease, 115(6 Pt 2), pp. 37-47.

Wohlford-Lenane, C. L., Durham, P. L. & Snyder, J. M., 1992. Localization of surfactant-associated protein C (SP-C) mRNA in fetal rabbit lung tissue by in situ hybridization. American journal of respiratory cell and molecular biology, 6(2), pp. 225-234.

Experimental Model and Subject Details

ESC/iPSC Line Generation and Maintenance. All experiments involving the differentiation of human iPSC lines were performed with the approval of the Institutional Review Board of Boston University (protocol H33122). BU3 and C17 iPSC lines carrying the NKX2-1GFP reporter were obtained from our prior studies (Hawkins et al. 2017).

These lines were derived from a normal donor (BU3) (Kurmann et al. 2015) and an individual with cystic fibrosis (C17) carrying a published compound heterozygous CFTR genotype (Crane et. al. 2015), respectively. The iPSC line SP212 was derived by reprogramming dermal fibroblasts (see below) of a patient with respiratory distress syndrome resulting from documented homozygous 121ins2 mutations (c.397delinsGAA (p.P133Efs*95), hg19) in the surfactant protein B (SFTPB) locus. The Institutional Review Board of Washington University, St. Louis, Mo., approved procurement of fibroblasts with documented informed consent.

All PSC lines used in this study (BU3, C17, RUES2, SP212 and SP212Corr) displayed a normal karyotype when analyzed by G-banding both before and after gene-editing (Cell Line Genetics, Madison, Wis.). Culture conditions used for maintenance and editing of undifferentiated PSCs were as follows: for TALENs targeting, PSC lines were maintained on mitomycin C-inactivated MEFs in human iPSC media (WiCell feeder dependent protocol). For CRISPR targeting and prior to directed differentiation, all PSC lines were maintained in feeder-free conditions, on growth factor reduced matrigel (Corning, Corning, N.Y.) in 6-well tissue culture dishes (Corning), in mTeSR1 medium (StemCell Technologies, Vancouver, Canada) using gentle cell dissociation reagent for passaging. Further details of iPSC derivation, characterization, and culture are available for free download at bu.edu/dbin/stemcells/protocols.php.

Reprogramming to generate SFTPB 121ins2 iPSCs. Reprogramming of patient-specific dermal fibroblasts (FIGS. 7A-7F, 13A-13B) was performed with a single-integrated excisable copy of the floxed hSTEMCCA lentiviral reprogramming vector (Somers, et. al., 2010) followed by excision with transient Cre recombinase-exposure. Ten iPSC colonies were mechanically isolated 30 days after lentiviral transduction and expanded on MEF feeders in human "iPSC media" (Somers et al., 2010), composed of DMEM/F12 (Sigma-Aldrich) with 20% KnockOut™ Serum Replacement (Invitrogen), 1 mM nonanimal L-glutamine (Sigma-Aldrich), 0.1 mM B-mercaptoethanol, and 10 ng/ml FGF2 (R&D Systems) on 0.1% gelatin (Sigma-Aldrich) coated plates preseeded with mitomycin C-inactivated or irradiated mouse embryonic fibroblast (MEF) feeder cells. Integrated hSTEMCCA copy number was assessed by Southern blot of BamHI-digested gDNA extracts probed for the lentiviral WPRE cassette (Somers, et. al. 2010), and only iPSC clones with single copy hSTEMCCA integrations were selected for vector excision and further study. The single copy hSTEMCCA lentiviral cassette was removed from two iPSC clones (SP212-1 and SP212-5) via transient transfection of pHAGE2-Cre-IRES-PuroR plasmid DNA (Somers et al. 2010; Addgene #30205) using Hela Monster™ transfection reagent (Mirus, Madison, Wis., mirusbio.com) according to the manufacturer's instructions (Somers, et al. 2010). Approximately 11-14 days later, colonies were picked and gDNA from each subclone was screened for vector excision by PCR using the following primers and conditions: cMYC F5'-GGA ACT CTT GTG CGT AAG TCG ATA G-3' (SEQ ID NO: 1); WPRE R5'-GGA GGC GGC CCA AAG GGA GAT CCG-3' (SEQ ID NO: 2); 95° C. for 3 minutes; followed by 33 cycles of 94° C. for 30 seconds, 60° C. for 30 seconds, and 72° C. for 1 minute; followed by a single cycle of 72° C. for 5 minutes. Vector excision was then confirmed by Southern blot using BamHI digested gDNA probed for the WPRE element (Somers, et. al. 2010) to identify two iPSC lines (each generated from the two separately picked clones (renamed SP212-1-Cr3 and SP212-5-Cr3 to reflect successful vector excision; FIG. 13A-13B).

SFTPCtdTomato Reporter ESC/iPSC Line Generation. To generate $SFTPC^{tdTomato}$ knock-in reporter ESCs, TALENs were designed to target the sequences close to the translation initiation (ATG) site of the human SFTPC gene. The SFTPC TALEN recognition sequences are: left TALEN 5'-TAG CAC CTG CAG CAA GAT GG-3' (SEQ ID NO: 3) and right TALEN 5'-TCA CCG GCG GGC TCT CCA TC-3' (SEQ ID NO: 4). Between the two binding sites is a 22 bp spacer (ATG TGG GCA GCA AAG AGG TCC T (SEQ ID NO: 5)). TALENs were constructed using EZ-TAL™ TALE Assembly Kit (System Bioscience, Palo Alto, Calif.), according to manufacturer's instruction, and the resulting SFTPC TALENS encoding plasmids were named: EF1a-TALEN_NN (SPC left) and EF1a-TALEN_HD (SPC right), respectively.

To deliver the donor template to the SFTPC locus, a donor vector was generated (p1303 DV-SFTPC-tdTomato; map and sequence available at kottonlab.com) containing the tdTomato coding sequence and a floxed PGK promoter-driven puromycin resistance cassette, flanked by left and right arms of homology to the human endogenous SFTPC locus, as follows: the CReM's targeting vector, TVGIP-eGFP-puro was first modified (CReM of Boston University and Boston Medical Center; bumc.bu.edu/stemcells). The GIP-eGFP sequence was replaced with the tdTomato coding sequence. 5' and 3' arms of homology to the SFTPC locus were generated by PCR cloning using gDNA extracts of human ES cells (RUES2) as templates. The 5' arm of homology extends 750 base pairs upstream of the SFTPC ATG start site, and the 3' arm of homology extends 750 base pairs downstream of the ATG start site.

The TALENs and donor vector plasmids were co-transfected into the following PSC lines: RUES2, C17 NKX2-1GFP, and BU3 NKX2-1GFP (Hawkins et al. 2017,) using a lipofectamine based transfection protocol. Each line was plated onto a mitomycin C-inactivated DR4 mouse embryonic fibroblast (MEF) feeder layer and cultured in human iPSC media (WiCell) in a 6 well plate. After the cells reached 50% confluence, they were transfected with the two TALENs and tdTomato donor vector as follows: 3 ug of donor vector and 1.2 ug of each TALEN were added to 275 ul of IMDM and 4 ul of Plus reagent from the Lipofectamine LTX kit (Thermo Fisher), and this mixture was incubated at room temperature for 5 minutes. 16 ul of lipofectmine LTX from the same kit was added to another 275 ul of IMDM. 275 ul of the DNA mixture was added to 275 ul of the LTX mixture and incubated at room temperature for 30 minutes.

550 ul of the total mixture was added drop by drop to 1 well of a 6 well plate. 5 hours later, the media was changed, and 48 hours later, 0.7 ug/ml puromycin (Fisher Scientific) was added to the media for 4 days to select antibiotic resistant colonies. After 10 days individual colonies from each line were picked and screened for targeting using the following primer pairs (Figure S1): GGG TGA GTG AGC TGA TTC GAG (SEQ ID NO: 6), TGA CCT CCT CGC CCT TGC TCA CCA TG (SEQ ID NO: 7). To confirm heterozygous targeting, colonies were screened for a remaining intact SFTPC gene using the following primers: CTA CGG ACA CAT ATA AGA CCC TGG TC (SEQ ID NO: 8), GCT GTG CAT CCC ACA CCT (SEQ ID NO: 9). DNA sequencing using a primer binding in the genome outside any regions included in targeting plasmids confirmed targeting into the endogenous SFTPC locus (GGG TGA GTG AGC TGA TTC GAG (SEQ ID NO: 6)).

Cre-mediated excision of the foxed puromycin resistance cassette was performed using a plasmid containing Cre-recombinase and neomycin resistance (PHAGE2 EF1a-Cre-IRES-NeoR-W; kottonlab.com) using the same lipofectamine-based protocol described above, with 4 days of 200 ng/ul geneticin-based (Life Tech) selection for clones that were transfected with Cre-containing plasmid. Excision of the puromycin cassette was confirmed by PCR using the following primers: ATG ACC GAG TAC AAG CCC ACG (SEQ ID NO: 10), TCA GGC ACC GGG CCT GC (SEQ ID NO: 11).

CRISPR-based gene correction of SFTPB 121ins2 mutation. CRISPR/Cas9 technology was used to target the region adjacent to the 121ins2 mutation (also known as c.397delinsGAA (p.P133Efs*95), hg19) in the human SFTPB gene locus (FIG. 7) with a guide RNA (specifically recognizing the 121ins2 mutation but not wild-type) that had the following sequence: 5' TTG ACG ACT ACT TCG AAC CCT GG 3' (SEQ ID NO: 12). gRNA sequences were commercially cloned into the pD1321-AD plasmid backbone (DNA 2.0 ATUM) that contains a M-dasher-GFP sequence fused to Cas9. Delivery of this plasmid to iPSCs enabled co-expression of Cas9, gRNA, and a GFP reporter. To accomplish footprint-free correction of the SFTPB mutation, a short single stranded DNA oligo (sequence 5'-GAA GCT GCT CAT GCC CCA GTG CAA CCA AGT GCT TGA CGA CTA CTT CCC CCT GGT CAT CGA CTA CTT CCA GAA CCA GAT TGT GAG GCT G-3' (SEQ ID NO: 13)) was used as a donor template containing the wild type SFTPB sequence. SP212 cells maintained in feeder-free conditions in mTeSR1 media were treated with 10 μM Y-27632 (Tocris) for 3 hours, dissociated in Gentle Cell Dissociation Reagent (GCDR, StemCell Technologies) for 10 minutes at 37° C. and counted using a Luna-II Automated Cell counter (Logos Biosystems, Annandale, Va.). Approximately 5×106 cells were centrifuged at 200g×5 minutes, resuspended in a mixture containing P3 solution and supplement (Lonza, Basel, Switzerland) as well as 5 ug CRISPR/Cas9 plasmid and 5 ug oligo donor, and nucleofected using program code CB-150 in the 4-D nucleofector system (Lonza). Nulceofected cells were replated on 2 wells of a matrigel-coated 6 well plate in mTeSR1 media, and 10 uM Y-27632 was added for 24 hours. After 48 hours, cells were prepared for sorting. They were treated with 10 uM Y-27632 for 3 hours, dissociated into single cell suspension with GCDR for 10-15 minutes at 37° C., centrifuged at 200g×5 minutes, resuspended in mTeSR1 media+10 uM Y-27632, and filtered through a 30 uM filter (Falcon). GFP+ cells were sorted into recovery media (1 part mTeSR1 and 1 part conditioned mTeSR1 supplemented with 0.7 ng/ml FGF2, plus 10 uM Y-27632) using a high-speed cell sorter (MoFlo Legacy, Beckman Coulter, Brea, Calif.). 1×104 cells GFP+ sorted cells were plated into a 10 cm tissue culture treated dish pre-coated with growth factor-reduced matrigel. Recovery media was changed every other day for the first 5 days, with 10 uM Y-27632 added for the first 24 hours. After 5 days, mTeSR1 was used to feed the cells, and after 10 days, colonies that emerged were of sufficient size for picking for clonal expansion and screening. Individual colonies were picked and screened for correction using the following primers: ACT CCT TGG CAC TCG TGA AC (SEQ ID NO: 14), GGG TGC TGT GTG TTT GTG TC (SEQ ID NO: 15). In pre-correction SP212, there is a BstB1 restriction site created by the 121ins2 mutation, and after enzyme digestion, 2 bands at 230 bp and 191 bp appear. Post-correction, the BstB1 site disappears, and only the uncut 430 bp band is seen on a gel. After PCR screening, colonies with the uncut band were further analyzed for correction, which was confirmed by DNA sequencing, resulting in the SP212Corr line.

Method Details

Directed Differentiation of PSCs into NKX2-1+ lung progenitors. PSC directed differentiation into NKX2-1 lung progenitors was performed as described previously (Hawkins, et al. 2017; Rankin et al. 2016). Briefly, cells maintained on mTESR1 media were differentiated into definitive endoderm using the STEMdiff Definitive Endoderm Kit (StemCell Technologies), with 1 day addition of supplement A only, and 2 days addition of supplements A and B (Day 4 in the STEMdiff kit protocol). After the endoderm-induction stage, cells were dissociated using GCDR and passaged at a ratio between 1:2 to 1:6 into 6 well plates coated with growth factor reduced matrigel in "DS/SB" anteriorization media, consisting of complete serum-free differentiation medium (cSFDM) base, including IMDM (ThermoFisher, Waltham, Mass.) and Ham's F12 (ThermoFisher) with B27 Supplement with retinoic acid (Invitrogen, Waltham, Mass.), N2 Supplement (Invitrogen), 0.1% bovine serum albumin Fraction V (Invitrogen), monothioglycerol (Sigma, St. Louis, Mo.), Glutamax (ThermoFisher), ascorbic acid (Sigma), and primocin with supplements of 10 μM SB431542 ("SB"; Tocris, Bristol, United Kingdom) and 2 μM Dorsomorphin ("DS"; Stemgent, Lexington, Mass.). For the first 24 hours after passaging, 10 μM Y-27632 was added to the media. After anteriorization for 3 days (72 hours), cells were cultured in "CBRa" lung progenitor-induction media for 9-11 days. "CBRa" media consists of cSFDM containing CHIR99021 (Tocris), 10 ng/mL recombinant human BMP4 (rhBMP4, R&D Systems), and 50 nM retinoid acid (RA, Sigma), as previously described (Rankin, et al., 2016). On Day 15 of differentiaton, efficiency of specification of NKX2-1+ lung progenitors was evaluated either by flow cytometry for intracellular NKX2-1 protein, NKX2-1GFP reporter expression, or by expression of surrogate cell surface markers CD47hi/CD26 based on the method of Hawkins and Kotton (Hawkins et al., 2017).

Purification of NKX2-1+ Lung Progenitors by Cell Sorting. On day 15 of differentiation, cells were incubated at 37° C. in 0.05% trypsin-EDTA (Invitrogen) for 7-15 minutes, until they reached single cell suspension. Cells were then washed in media containing 10% fetal bovine serum (FBS, ThermoFisher), centrifuged at 300g×5 minutes, and resuspended in sort buffer containing Hank's Balanced Salt Solution (ThermoFisher), 2% FBS, 10 μM Y-27632, and 10 uM calcein blue AM (Life Technologies) for dead cell exclusion. Cells not containing the NKX2-1GFP reporter were subsequently stained with CD47-PerCPCy5.5 and CD26-PE antibodies (mouse monoclonal; Biolegend 1:200; 1×106 cells in 100 ul) for 30 minutes at 4° C., washed with PBS, and resuspended in sort buffer. Cells were passed through a 40 um strainer prior to sorting (Falcon). Various live cell populations indicated in the text (i.e. GFP+, GFP−, CD47hi/CD26−,CD47lo) were sorted on a high-speed cell sorter (MoFlo Legacy). Directed Differentiation of NKX2-1+ Lung Progenitor Outgrowth into iAEC2s Day 15 cells, either sorted (as described above) or unsorted (dissociated as described above), were resuspended in undiluted growth factor-reduced matrigel (Corning) at a dilution of 50-100 cells/ul, with droplets ranging in size from 20 ul in 96 well plates to 1 ml in 10 cm tissue culture-treated dishes (Corning). Cells in matrigel suspension were incubated at 37° C. for 20-30 minutes, then warm media was added to the plates.

Where indicated in the text, outgrowth and distal/alveolar differentiation of cells after day 15 was performed in "CK+DCI" medium, consisting of cSFDM base, with 3 μM CHIR99021, 10 ng/mL rhKGF, and 50 nM dexamethasone (Sigma), 0.1 mM 8-Bromoadenosine 3',5'-cyclic monophosphate sodium salt (Sigma) and 0.1 mM 3-Isobutyl-1-methylxanthine (IBMX) (Sigma) (DCI). Immediately after replating cells on Day 15 10 μM Y-27632 was added to the medium for 24 hours. Additional growth factors or cytokines were added or withdrawn as indicated in the text, including FGF10, TGFb, EGF, OSM (20 ng/ml), TNFa (10 ng/ml), and IL-1b (10 ng/ml) with other concentrations listed in figure legends (FIGS. 9A, 9B).

Alveolosphere Long Term Culture, Dissociation, and Differentiation. Alveolospheres developed in 3D matrigel culture outgrowths within 3-7 days after day 15 replating, and were maintained in CK+DCI media for weeks to months, as indicated in the text. These spheres were analyzed as follows: Z-stack images of live alveolospheres were taken and processed on a Keyence (Osaka, Japan) BZ-X700 fluorescence microscope. For some analyses (RT-qPCR, Western blot, lipidomic analysis) alveolospheres were released from matrigel droplets, and for other techniques (flow cytometry, cell sorting), they were dissociated into single cell suspension. To release alveolospheres from matrigel, droplets were incubated in dispase (2 mg/ml, Fisher) at 37° C. for 1 hour, centrifuged at 300g×1 minute, washed in 1x PBS, then centrifuged again at 300g×1 minute. To generate single cell suspensions, cell pellets were incubated in 0.05% trypsin and continued through the trypsin-based dissociation protocol described above, after which they could be passaged into fresh matrigel, analyzed by flow cytometry, or sorted as described above. Sorted cells from alveolospheres were replated into matrigel droplets for serial passaging where indicated in the text. For AEC1 differentiation experiments approximately 20,000 sorted SFTPCtdTomato+ cells were plated in 96 well tissue culture plates in Dulbecco's Modified Eagle Medium (DMEM), 10% FBS, glutamax, and primocin for 4-7 days, then harvested for analysis. For EdU labeling, alveolospheres in 3D culture were incubated in CK+DCI media with 5 uM EdU for 24 hours, then dissociated as described above, fixed, and processed according to the manufacturer's instructions (Click-iT® EdU Alexa Fluor® 488 Imaging Kit, Thermo Fisher).

Electron Microscopy of Alveolospheres. Alveolospheres were fixed for 3 hours total in 2.5% glutaraldehyde (Ladd Research, Williston, Vt.) in 0.1% cacodylate buffer pH 7.4 at room temperature. An equal volume of 5% glutaraldehyde/0.1M cacodylate was added to the Eppendorf tube with alveolospheres in known volume of media, fixed for 1.5 hours, and spun down gently (300g×1 minute). Fresh 2.5% glutaraldehyde/0.1M cacodylate was added, and the sample was fixed for an additional 1.5 hours at room temperature. The sample was then washed in 0.1M cacodylate three times, post-fixed in 1% Tannic Acid in cacodylate buffer for 5 minutes at room temperature, washed again 3 times in cacodylate buffer, and post fixed overnight in 1.5% osmium tetroxide (Polysciences, Warrington, Pa.) in 0.1M cacodylate buffer in dark at 4° C. The sample was washed 3-4 times in 0.05M Na Maleate buffer pH 5.2 and block stained in 1.5% Uranyl acetate (Electron Miscropscopy Sciences, (EMS), Hatfield, Pa.) in 0.025M Na Maleate buffer pH 6.0. Next, the sample was dehydrated quickly through acetone on ice, from 70% to 80% to 90%. Then, it was incubated 2 times in 100% acetone at room temperature for 10 minutes each, and in propylene oxide at room temperature for 15 minutes each. Finally, the sample was changed into EMbed 812 (EMS), left for 2 hours at RT, changed into fresh EMbed and left overnight at room temperature, after which it was embedded in fresh EMbed 812 and polymerized overnight at 60° C. Plastic embedded samples were thin sectioned at 70 nm and grids were stained in 4% aqueous Uranyl Acetate for 5 minutes at 60° C. followed by Lead Citrate for 10 mins at room temperature.

Sections on grids were imaged on a CM12 Transmission Electron Microscope (Philips, Amsterdam, Netherlands), using a TEMCAM F216 camera (TVIPS, Oslo, Norway) at an original magnification of 7875× and a Morgagni 268 (FEI, Eindhoven, Netherlands), using a Veleta camera (Olympus SIS, Münster, Germany) at original magnifications of 7200× and 14000×.

Immunogold Staining of Alveolospheres. Human iPSC-derived AEC2s were processed for immunogold labeling described previously (Ridsdale et al. 2011). Cultured iPSC were first fixed in situ with 4% paraformaldehyde (Electron Microscopy Sciences), 0.1% glularaldehyde (EMS, Hatfield, Pa.), 75 mM L-lysine (Sigma), 10 mM INaO4 (Sigma), and 0.1% $CaCl_2$) in 0.2M HEPES (Sigma), pH 7.2 at room temperature for 10 min, followed by postfixation with fresh fixative at 4° C. overnight. They were embedded with 10% gelatin, cryoprotected with 2.3M Polyvinylpyrrolidone (PVP; M.W. 10,000; Sigma)/sucrose (Sigma) in 0.2M HEPES, pH 7.2, and frozen in liquid nitrogen for cryoultramicrotomy. 70 to 80 nm frozen sections were picked up with mixture of 1.15M PVP/sucrose, 1% methyl cellulose (Sigma), 0.2% uranyl acetate (EMS, Hatfield, Pa.), and 0.1% glutatraldehyde, transferred to 200 mesh Butvar® coated nickel grids (EMS), and stored at −20° C. until they were ready for immunogold labeling. To localize SFTPB or SFTPC proteins, thawed frozen sections were stained with rabbit polyclonal Ab directed against mature SFTPB (Seven Hills; (Lin et al. 1996)) or mature SFTPC (Seven Hills; (Ross et al. 1999)),and 10 nm protein A gold (CMC, U. Utrecht, The Netherlands). Electron micrographs of labeled cells were acquired using a Hitachi TEM 7650 (Hitachi High Technologies America, Schaumburg, Ill.) with an AMT CCD camera (Advanced Microscopy Techniques, Woburn, Mass.).

Alveolosphere staining. Toluidine blue staining was performed as follows: 0.5 um sections (from EMbed plastic blocks) were collected, dried for 30 minutes on a hot plate, and stained 30-60 seconds in 0.5% Toluidine blue+0.5% Borax in dH20, rinsed in dH20, dried and coverslipped. PAS staining was performed according to manufacturer's instructions using the Sigma PAS kit.

SFTPB and SFTPC Protein Analyses by Western Blot. Cultured cells were treated with lysis buffer (RIPA buffer and 1x Roche Complete Protease Inhibitor cocktail). Buffer-treated cells were removed from the well, incubated on ice for 30 min, and cleared by centrifugation at 15,000G for 20 min. Supernatants were collected and stored at −80° C. until analysis. Protein was measured using the Bio-Rad DC Protein Assay. A total of 35 ug of alveolosphere lysate and 25 ug of lysate from AECs isolated from lung explants of 21 wk human lung cultured for 6 d in DCI were resolved on pre-cast 10% NUPAGE gels (Thermo Fisher) and transferred to PVDF membrane (Bio-Rad). Blots were incubated with the following primary antisera: surfactant protein B (PT3, a rabbit polyclonal antibody against bovine mature SP-B; Beers et al. 1992; 1:3000 dilution); NFLANK (rabbit polyclonal antibody against a synthetic peptide of Gln186-Gln200 of the human Pro-SPB amino acid sequence; dilution 1:5000; Korimilli et al. 2000; 1:2000); GAPDH (1:5000, Chemicon), NPRO-SFTPC (dilution 1:3,000, Beers et al. 1994), b-actin (dilution 1:10,000, Sigma). Species-specific secondary antisera were all conjugated to IR dyes of either 680 or 800 nm wavelengths (Rockland) at a dilution of 1:10000. Visualization was accomplished using the Odyssey Imaging System (LiCOR Biosciences, Lincoln, Neb.).

Lipidomic Analysis. Alveolospheres were dissociated from matrigel as described above, and incubated in 1 ml of trypsin for 5 minutes to break apart the alveolospheres but leave cells intact. After centrifugation, the trypsin "extracellular sample" was separated from the cell pellet "intracellular sample," the cell pellet was washed in PBS, and both samples were stored at −80 C until ready to process.

For lipid extraction, a modified Bligh & Dyer protocol was used with an internal standard of 14:0 PC (DMPC) from Avanti Polar Lipids, Alabaster, Ala.). For extracellular samples, we used 500 ng PC (0.738 nmol) per sample, and for intracellular samples, we used 2000 ng PC (2.95 nmol) PC per sample. All reagents (water, methanol, chloroform) used were HPLC grade.

Internal standard was added to each disposable glass culture tube prior to addition of a sample. Each cell pellet and extracellular supernatant was resuspended in 1 ml water, transferred to a tube, and 3 ml methanol:chloroform (2:1) was added, intracellular samples were sonicated for 30 seconds, and extracelullar samples were vortexed for 30 seconds. 1 ml chloroform and 1 ml water were added to each sample, followed by 30 seconds of vortexing. Samples were centrifuged for 5-10 minutes at 1500×g and the bottom layer was collected with a glass pasteur pipet and dried under nitrogen gas. Intracellular samples were resuspended in 300 ul methanol, and extracellular samples were resuspended in 100 ul methanol.

Electrospray ionization (ESI)/tandem mass spectrometry and gas chromatography/mass spectrometry (GC/MS) were used, respectively, to measure phosphatidylcholine (PC) composition in the samples. Results are described as "Absolute Quantification" based on alveolosphere DNA amount in ng or as "Relative Quantification" (Absolute Quant of each individual PC species, such as PC 32:0, divided by total acyl PC to get a ratio).

Isolation of primary AECs. Week 21 human lung tissues were obtained in the Guttentag laboratory under protocols originally reviewed by the Institutional Review Board at the Children's Hospital of Philadelphia and subsequently reviewed by Vanderbilt University and in the Beers laboratory under a University of Pennsylvania Institutional Review Board exemption and isolated as previously published. The cell stocks used in the present studies were donated to the Kotton laboratory for the purpose of providing reference data. "Week 21" samples were isolated by the overnight culture of lung explants in Waymouth media; a technique that generally yields 86±2% epithelial cells with the remaining cells consisting of fibroblasts with <1% endothelial cells. "Week 21 DCI" samples were prepared in a similar manner except that the lung explants were also cultured for 4 days in Waymouth's media supplemented with DCI (10 nM Dexamethasone, 0.1 mM 8-Br cAMP, and 0.1 mM 3-isobutyl-1-1methylxanthine), and "HFL DCI-D6" samples were cultured in this media for 6 days. Week 21 epithelial cells do not exhibit features of alveolar type 2 cells including lamellar bodies, whereas Week 21 DCI epithelial cells do exhibit lamellar bodies (Wade et al. 2006); (Gonzales et al. 2002).

Isolation of Adult AEC2s. For human primary lung epithelial isolation, 1×1 cm pieces of distal human lung obtained from healthy regions of the upper lobe of non-utilized human lungs donated for transplantation were dissected and all airway tissue and pleura was removed. The tissue was then digested using dispase, collagenase I, and DNase using the gentleMACS dissociator (Miltenyi) for 30 minutes at 37° C. The resulting cell suspension was passed over 70 uM and 40 uM filters to generate a single cell suspension. Purified human AEC2 cells were obtained by magnetic bead sorting using MACS LS columns (Miltenyi) and the following antibodies: HT2-280 (anti-human AEC2 antibody, IgM, Terrace Biotechnologies) and anti-IgM magnetic beads (Miltenyi). MACS-sorted cells were collected into trizol.

RNA Sequencing and Computational Analyses. The following samples were harvested from RUES2 PSCs in Qiazol (Qiagen) for RNA Sequencing analysis. (1) Day 0 samples representing undifferentiated PSCs cultured feeder-free in mTeSR1 media, as described above. (2) Day 15 samples representing CD47hi/CD2610 sorted lung progenitor. Flow cytometry analysis confirmed that this population consisted of between 85-90% NKX2-1+ cells. (3) Day 35 SFTPCtd-Tomato+(Tom+) and SFTPCtdTomato− (Tom−) samples resulting from the outgrowth of the day 15 sorted progenitors. Other samples were harvested from primary cells: (1) Week 21 human fetal distal lung cells (as described above), (2) Week 21 human fetal distal lung cells, cultured in "DCI" media for 4 days (as described above), and (3) Adult AEC2s purified by HT2-280-based sorting (as described above). Sequencing libraries were prepared from total RNA samples using Illumina TruSeq RNA Sample Preparation Kit v2. The mRNA was isolated using magnetic beads-based poly(A) selection, fragmented, and randomly primed for reverse transcription, followed by second-strand synthesis to create double-stranded cDNA fragments. These cDNA fragments were then end-repaired, added with a single 'A' base, and ligated to Illumina® Paired-End sequencing adapters. The products were purified and PCR-amplified to create the final cDNA library. The libraries from individual samples were pooled in groups of four for cluster generation on the Illumina cBot using Illumina TruSeq Paired-End Cluster Kit. Each sample was sequenced four per lane on the Illumina HiSeq 2500 to generate more than 30 million single end 100-bp reads.

Fastq files were assessed for quality control using the FastQC program. Fastq files were aligned against the human reference genome (hg19/hGRC37) using the STAR aligner (Dobin et al. 2013). Duplicate reads were flagged using the MarkDuplicates program from Picard tools. Gene counts represented as counts per million (CPM) were computed for Ensembl (v67) gene annotations using the Rsubread R package with duplicate reads removed. Genes with 10% of samples having a CPM<1 were removed and deemed low expressed. The resultant data was transformed using the VOOM method implemented in limma R package (Law, et al. 2014). Voom transformed data can now be tested for differential gene expression using standard linear models using the limma package. Multiple hypothesis test correction was performed using the Benjamini-Hochberg procedure (FDR). Heatmaps and PCA plots were generated in R. Gene Set Enrichment Analysis (GSEA) was performed using the camera method implemented on the limma package using gene sets from the Molecular Signatures database (MSigDB).

Raw fastq files and VOOM transformed gene expression files are available on line at the gene expression omnibus, GEO (accession number pending) as well as on the Kotton Lab's Bioinformatics Portal at kottonlab.com.

Reverse Transcriptase Quantitative Real Time Polymerase Chain Reaction (RT-qPCR). RT-qPCR was performed as previously described (Hawkins et al. 2017,). Briefly, RNA was isolated according to manufacturer's instructions using the Qiagen miRNeasy mini kit (Qiagen, Venlo, Netherlands). cDNA was generated by reverse transcription of up to 150 ng RNA from each sample using the Applied Biosystems High-Capacity cDNA Reverse Transcription Kit. For qPCR, technical triplicates of either 20 ul reactions (for use in Applied Biosystems StepOne 96-well System) or 12 ul reactions (for use in Applied Biosystems QuantStudio7 384-well system) were prepared with 2 ul of diluted or undiluted cDNA and run for 40 cycles. All primers were TaqMan probes from Applied Biosystems (see all in Key Resources Table). Relative gene expression was calculated based on the average cycle (Ct) value of the technical triplicates, normalized to 18S control, and reported as fold change ($2^{(-\Delta\Delta CT)}$), with a fold change of 1 being assigned to undifferentiated (day 0) iPSCs or ESCs. Undetected probes were assigned a Ct value of 40 to allow for fold change calculations.

Immunofluorescence Microscopy of Cultured Cells. Alveolospheres were dissociated as described above, washed in dPBS, and fixed with 4% paraformaldehyde. Alveolospheres were subsequently either processed for cryosectioning or whole-mount staining. For cryosectioning, fixed alveolospheres were first embedded in low melting temperature agarose (SeaPrep) and after incubation in 7.5% and 30% sucrose solution, further embedded in OCT, flash frozen, and 6 um sections were cut on a cryotome. Both whole mount alveolospheres and frozen sections were washed in dPBS, blocked in 4% normal donkey serum (NDS) with 0.5% Triton X-100 (Sigma) for 30 minutes, and incubated overnight in primary antibody (see Table 1) in 0.5% Triton X-100 and 4% NDS. Samples were then washed in 4% NDS and incubated with secondary antibody from Jackson Immunoresearch (1:300 anti rabbit IgG (H+L) or anti mouse IgG (H+L)) for 2 hours at room temperature. Nuclei were stained with Hoescht dye (Thermo Fisher, 1:500) and sections were mounted with Prolong Diamond Anti-Fade Mounting Reagent (ThermoFisher) and coverslipped, while whole mount alveolospheres were mounted on cavity slides. Both stained whole mount and cryosectioned alveolospheres were visualized with a Zeiss (Jena, Germany) confocal microscope.

Quantification and Statistical Analysis

Statistical Methods. In figures containing RT-qPCR, flow cytometry, or lipidomics data, data was presented as the mean with error bars representing the standard deviation from the mean. Unpaired, two-tailed Student's t-tests were performed on 2 groups of n≥3 replicates each, and the p-value threshold to determine significance was set at p=0.05. Replicates generally represent samples differentiated separately from the PSC stage, though in some cases they represent separate sorted populations from the same differentiation.

Immunogold Quantification. To determine if immunogold stained mature SFTPB and mature SFTPC localized to specific cellular compartments in PSC-derived cells, gold counts registered on biosynthetic and non-biosynthetic compartments were tabulated and analyzed by relative labeling index (RLI) described by Mayhew ((Mayhew 2011)). Briefly, a non-destructive counting grids generated by the grid plugin under FIJI was randomly superimposed over the acquired electron micrograph at magnification of 15,000. Gold counts and sampled grid points registered on the compartments of interest, i.e., multivesicular bodies/lamellar bodies, were collected for estimation of the expected gold counts for selected compartments after normalization to surface areas of selected compartment to total cell surface areas. To determine if gold labeling was specific to the compartments of interests, observed counts (n=1160 and 2510 total gold particles for SFTPB and SFTPC, respectively) were compared with expected counts by $\chi 2$ statistics and contingency table analyses (Conover, 1999, Practical Nonparametric Statistics, 3rd ed., p 179-268). Any cellular compartment that had RLI>1 (p-value<0.05) and significantly higher partial $\chi 2$ value compared to other compartments was considered labeled preferentially by SFTPB or SFTPC antibodies (25% of total $\chi 2$ value was arbitrarily chosen for this study).

121ins2 SFTPB deficiency patient history. Female infant twin B was born at 35 weeks gestation (birth weight 2173g, 10-50th percentile) via cesarean section due to non-reassuring antenatal surveillance of male twin A. Pregnancy was notable for diamniotic/dichorionic twin gestation and chronic hypertension for which mother received methyldopa. Apgars were 8 at 9 and 1 and 5 minutes of life, respectively. The infant developed respiratory distress and cyanosis within minutes of birth and required intubation, mechanical ventilation, and surfactant replacement therapy. Her respiratory status stabilized and she was extubated on day of life 4 to continuous positive airway pressure. However, she developed progressive respiratory failure prompting reintubation, additional surfactant replacement therapy, high frequency oscillatory ventilation with FiO2 1.0 and nitric oxide to maintain adequate arterial saturations. She was also treated with glucocorticoids (methylprednisolone, hydrocortisone) and diuretics (aldactazide and furosemide). Lung biopsy at 1 month of age demonstrated interstitial pneumonitis and type II pneumocyte hyperplasia. Genetic testing revealed homozygous, loss of function mutations (c.397delinsGAA (p.P133Efs*95), hg19; also known as "121ins2") in the surfactant protein B gene (SFTPB). The infant underwent bilateral lung transplantation at 4 months of age. Lung explant histology revealed abnormal small air space development, marked hypertrophy of smooth muscle with extension into the lung periphery, type II pneumocyte hyperplasia, evidence of alveolar proteinosis, and vascular changes consistent with pulmonary hypertension. She is alive 8 years post lung transplant and doing well at the time of manuscript submission.

TABLE 1

| REAGENT or RESOURCE | SOURCE | IDENTIFIER |
|---|---|---|
| Antibodies | | |
| Rabbit monoclonal to NKX2-1 (clone EP15847) | Abcam | Cat.# ab76013 |
| Mouse monoclonal to NKX2-1 (clone 8G7G3/1) | Abcam | Cat.# ab72876 |
| Rabbit polyclonal to Pro-SFTPB | Seven Hills | Cat.# WRAB-55522 |
| Rabbit polyclonal to Pro-SFTPC | Seven Hills | Cat.# WRAB-9337 |
| Rabbit polyclonal to Mature SFTPB | Seven Hills | Cat.# r28031 |
| Rabbit polyclonal to Mature SFTPC | Seven Hills | Cat.# r76694 |
| Mouse monoclonal to EPCAM (clone AUA1) | Abcam | Cat.# ab181853 |
| Mouse monoclonal to CD26, PE | Biolegend | Cat.# 302705 |

TABLE 1-continued

| REAGENT or RESOURCE | SOURCE | IDENTIFIER |
|---|---|---|
| conjugated (clone BA5b) | | |
| Mouse monoclonal to CD47, PerCP-Cy5.5 conjugated (clone CC2C6) | Biolgend | Cat.# 323110 |
| Mouse monoclonal to red fluorescent protein (RFP) | Abcam | Cat.# 65856 |
| Rabbit monoclonal to red fluorescent protein (RFP) | Rockland | Cat.# 600-401-379 |
| Anti-mature SFTPB (PT3) | Guttentag/Beers Lab (Beers, et al. 1992) | |
| Anti-NFLANK SFTPB | Guttentag Lab (Korimilli, et al. 2000) | |
| Anti-NPRO SFTPC | Beers Lab (Beers, et al. 1994) | |
| Anti-pan actin | Cell Signaling | Cat.# 8456 |
| Anti-GAPDH | Chemicon | Cat.# MAB374 |
| Anti-bActin | Sigma | Cat.# A1978 |
| Anti- phosphoStat3 | Cell Signaling | Cat.# 9131 |
| Anti IkB | Santa Cruz | Cat.# sc-371 |
| AffiniPure Donkey Anti-Rabbit IgG (H + L), 488 conjugated | Jackson Immunoresearch | Cat.# 711-225-152 |
| AffiniPure Donkey Anti-Rabbit IgG (H + L), Cy3 conjugated | Jackson Immunoresearch | Cat.# 711-165-152 |
| AffiniPure Donkey Anti-Rabbit IgG (H + L), AlexaFluor 647 conjugated | Jackson Immunoresearch | Cat.# 711-605-152 |
| AffiniPure Donkey Anti-Mouse IgG (H + L), AlexaFluor 647 conjugated | Jackson Immunoresearch | Cat.# 715-605-150 |
| AffiniPure Donkey Anti-Mouse IgG (H + L), AlexaFluor Cy3 conjugated | Jackson Immunoresearch | Cat.# 715-165-150 |
| AffiniPure Donkey Anti-Goat IgG (H + L), AlexaFluor 647 conjugated | Jackson Immunoresearch | Cat.# 305-605-003 |
| Biological Samples | | |
| Chemicals, Peptides, and Recombinant Proteins | | |
| Growth Factor Reduced Matrigel | Corning | Cat.# 356230 |
| SB431542 | Tocris | Cat.# 1614 |
| Dorsomorphin | Stemgent | Cat.# 04-0024 |
| CHIR99021 | Tocris | Cat.# 4423 |
| Recombinant human FGF10 | R&D Systems | Cat.# 345-FG-025 |
| Recombinant human KGF | R&D Systems | Cat.# 251-KG-010 |
| Recombinant human BMP4 | R&D Systems | Cat.#314-BP |
| Retinoic acid | Sigma | Cat.# R2625 |
| Y-27632 dihydrochloride | Tocris | Cat.# 1254 |
| Recombinant human FGF2 | R&D Systems | Cat.# 233-FB |
| Recombinant human TGF☐ | R&D Systems | Cat.# 240-B |
| DAPT | Sigma | Cat.# D5942 |
| Dexamethasone | Sigma | Cat.# D4902 |
| 8-bromoadenosine 3',5'-cyclic monophosphate sodium salt (cAMP) | Sigma | Cat.# B7880 |
| 3-Isobutyl-1-methylxanthine (IBMX) | Sigma | Cat.# I5879 |
| Recombinant mouse Noggin | R&D Systems | Cat.# 1967-NG |
| Recombinant mouse EGF | R&D Systems | Cat.# 2028-EG-200 |
| Hoechst | Thermo Fisher Scientific | Cat.# H3570 |
| Puromycin Dihydrochloride | Thermo Fisher | Cat.# A1113802 |
| Geneticin Sulfate | Life Technologies | Cat.# 11811-023 |
| 0.05% trypsin-EDTA | Invitrogen | Cat.# 25300-120 |
| Defined Fetal Bovine Serum | Thermo Fisher | Cat.# NC0652331 |
| Calcein blue | Life Technologies | Cat.# C1429 |
| Recombinant human TNFa | R&D Systems | Cat.# 210-TA-005 |
| Recombinant human IL1-b | R&D Systems | Cat.# 201-LB-005 |
| Recombinant human OSM | R&D Systems | Cat.# 295-OM-010/CF |
| Dispase | Thermo Fisher | Cat.# 354235 |
| Glutaraldehyde | Ladd Research | Cat.# 20100 |
| Osmium Tetroxide | Polysciences | Cat.# 0223D |
| Uranyl Acetate | Electron Microscopy Sciences | Cat.# 22400 |
| EMbed 812 | Electron Microscopy Sciences | Cat.# 14120 |
| 14:0 PC (DMPC) | Avanti Polar Lipids | Cat.# 850345 |
| Paraformaldehyde | Electron Microscopy Sciences | Cat.# 19208 |

TABLE 1-continued

| REAGENT or RESOURCE | SOURCE | IDENTIFIER |
|---|---|---|
| Critical Commercial Assays | | |
| RNeasy Mini Kit | Qiagen | Cat.# 74104 |
| QIAzol Lysis Reagent | Qiagen | Cat.# 79306 |
| TaqMan Fast Universal PCR Master Mix (2X), no AmpErase UNG | Thermo Fisher | Cat.# 4364103 |
| High-Capacity cDNA Reverse Transcription Kit | Applied Biosystems | Cat.# 4368814 |
| Deposited Data | | |
| RNA-Sequencing of timecourse PSC-derived lung differentiation | | GEO#: TBD |
| Experimental Models: Cell Lines | | |
| Normal donor induced pluripotent stem cell (iPSC) line (BU3) | Kotton Lab (Hawkins et al.press) | www.bumc.bu.edu/stemcells |
| Normal donor iPSC line targeted with NKX2-1$^{GFP}$ (BU3$^{GFP}$) | Kotton Lab (Hawkins et al.press) | www.bumc.bu.edu/stemcells |
| Cystic fibrosis donor iPSC line targeted with NKX2-1$^{GFP}$ (C17) | Gift from Dr. Brian Davis, Houston, TX | |
| SFTPB deficiency donor iPSC line (SP212) | This paper | |
| Corrected SFTPB deficiency donor iPSC line (SP212) | This paper | |
| RUES2 embryonic stem cell line | Gift from Dr. Ali H. Brivanlou, Rockefeller University | |
| Experimental Models: Organisms/Strains | | |
| Recombinant DNA | | |
| EF1a-TALEN_HD, EF1a-TALEN_NN | This paper | |
| p1303-DV-SFTPC-tdTomato | This paper | |
| pHAGE2 EF1a-Cre-IRES-NeoR-W | This paper | |
| pHAGE2-Cre-IRES-PuroR | Kotton Lab (Somers et al. 2010) | Addgene #30205 |
| pD1321-AD- SFTPB121ins2 | DNA 2.0 ATUM | |
| Sequence-Based Reagents | | |
| TaqMan Gene Expression Assay Primer/Probe Sets | Thermo Fisher | |
| SFTPC | Thermo Fisher | Hs00161628_m1 |
| SFTPB | Thermo Fisher | Hs01090667_m1 |
| ABCA3 | Thermo Fisher | Hs00975530_m1 |
| LAMP3 | Thermo Fisher | Hs00180880_m1 |
| NKX2-1 | Thermo Fisher | Hs00968940_m1 |
| SLC34A2 | Thermo Fisher | Hs00197519_m1 |
| LPCAT1 | Thermo Fisher | Hs00227357_m1 |
| PDPN | Thermo Fisher | Hs00366766_m1 |
| AGER | Thermo Fisher | Hs00542584_g1 |
| AQP5 | Thermo Fisher | Hs00387048_m1 |
| SCGB1A1 | Thermo Fisher | Hs00171092_m1 |
| P63 | Thermo Fisher | Hs00978340_m1 |
| SOCS3 | Thermo Fisher | Hs02330328_s1 |
| IL-8 | Thermo Fisher | Hs00174103_m1 |
| GMCSF | Thermo Fisher | Hs00531296_g1 |
| NKD1 | Thermo Fisher | Hs00263894_m1 |
| LEF1 | Thermo Fisher | Hs01547250_m1 |
| Software and Algorithms | | |
| ImageJ | National Institutes of Health | Imagej.nih.gov/ij/ |
| Other | | |
| StemDiff Definitive Endoderm Kit | StemCell Technologies | Cat.# 05110 |
| mTeSR1 | StemCell Technologies | Cat.# 05850 |
| Glutamax | Life Technologies | Cat.# 35050-061 |
| Gentle Cell Dissociation Reagent | StemCell Technologies | Cat.# 07174 |
| Click-iT ® EdU Alexa Fluor ® 488 Imaging Kit | Thermo Fisher | Cat.# C10337 |
| EZ-TAL TALE Assembly Kit | System Bioscience | Cat.# GE120A-1 |
| Lipfectamine LTX Kit | Thermo Fisher | Cat.# 15338100 |
| P3 Primary Cell 4D-Nucleofector ® X Kit S | Lonza | Cat.# V4XP-3032 |
| PAS Kit | Sigma | Cat.# 395b |
| Hela Monster transfection reagent | Mirus | Cat.# MIR 2904 |

Example 3

Alveolar type II cell (AEC2) dysfunction is a primary cause of pathogenesis in many poorly understood lung diseases that lack effective therapeutics. Patient AEC2s are very difficult to isolate and study. Childhood interstitial lung disease (chILD) is a group of monogenic AEC2 diseases which can be caused by autosomal dominant mutations in the surfactant protein C (SFTPC) gene. Generating AEC2s de novo using induced pluripotent stem cell (iPSC) technology would provide novel opportunities to study diseases of the alveolar epithelium, including SFTPC mutations. Described herein are fluorescent reporter lines that enable the first ever isolation of a pure population of live iPSC-derived AEC2s (iAEC2s) for use in disease modeling and drug screening.

Figure 15A:
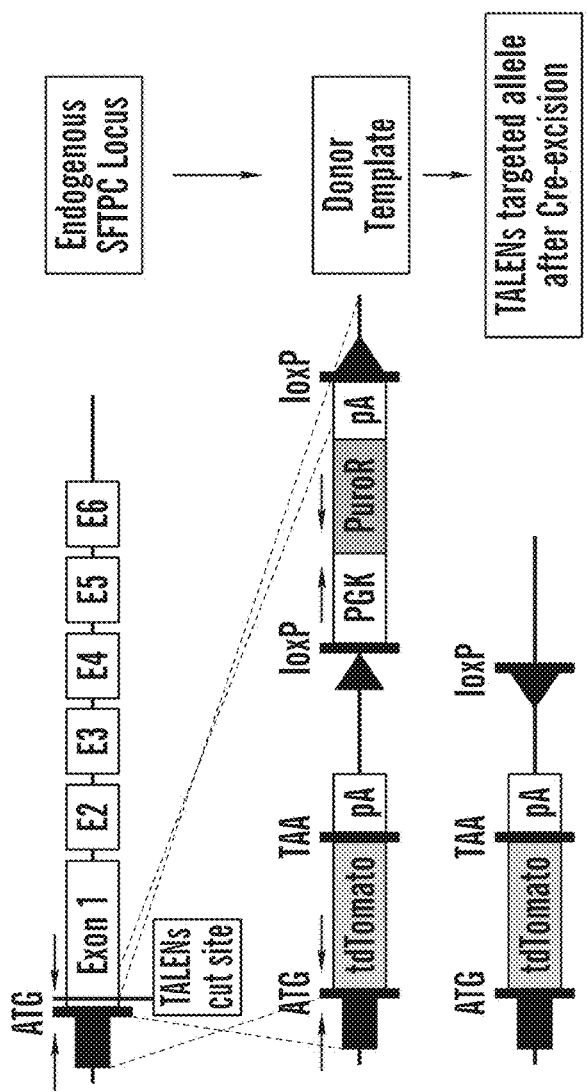
FIG. 15A depicts a summary of targeting strategy using TALENs to create a double strand break at the SFTPC start codon and inserting a tdTomato reporter cassette.
Figure 15B:
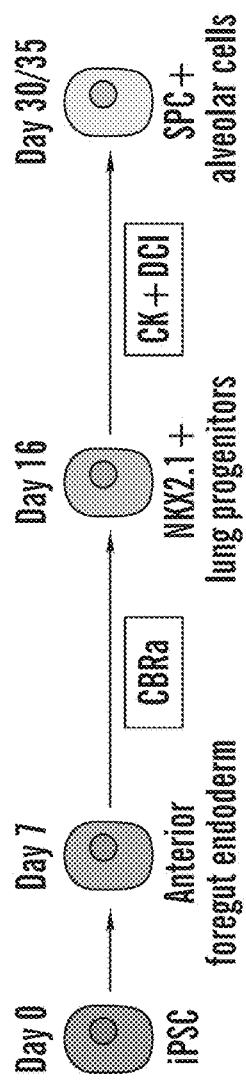
FIG. 15B depicts a schematic. iPSCs are sequentially differentiated into definitive endoderm, anterior foregut endoderm, immature lung progenitors, and finally mature lung lineages using specific combinations of exogenous signals suggested from the study of the embrygonesis.

SFTPC reporter hPSC lines allow identification of putative iAEC2s. A fluorescent reporter (GFP) was targeted into the endogenous SFTPC locus of human PSC lines. Site-specific TALE nucleases were used to create a double stranded break near the start codon of SFTPC, facilitating homologous recombination of the fluorescent reporter (FIG. 15A). A directed differentiation approach was used that recapitulates the key developmental milestones of the developing embryo to generate lung progenitors from these iPSCs (FIG. 15B).

Figure 16:
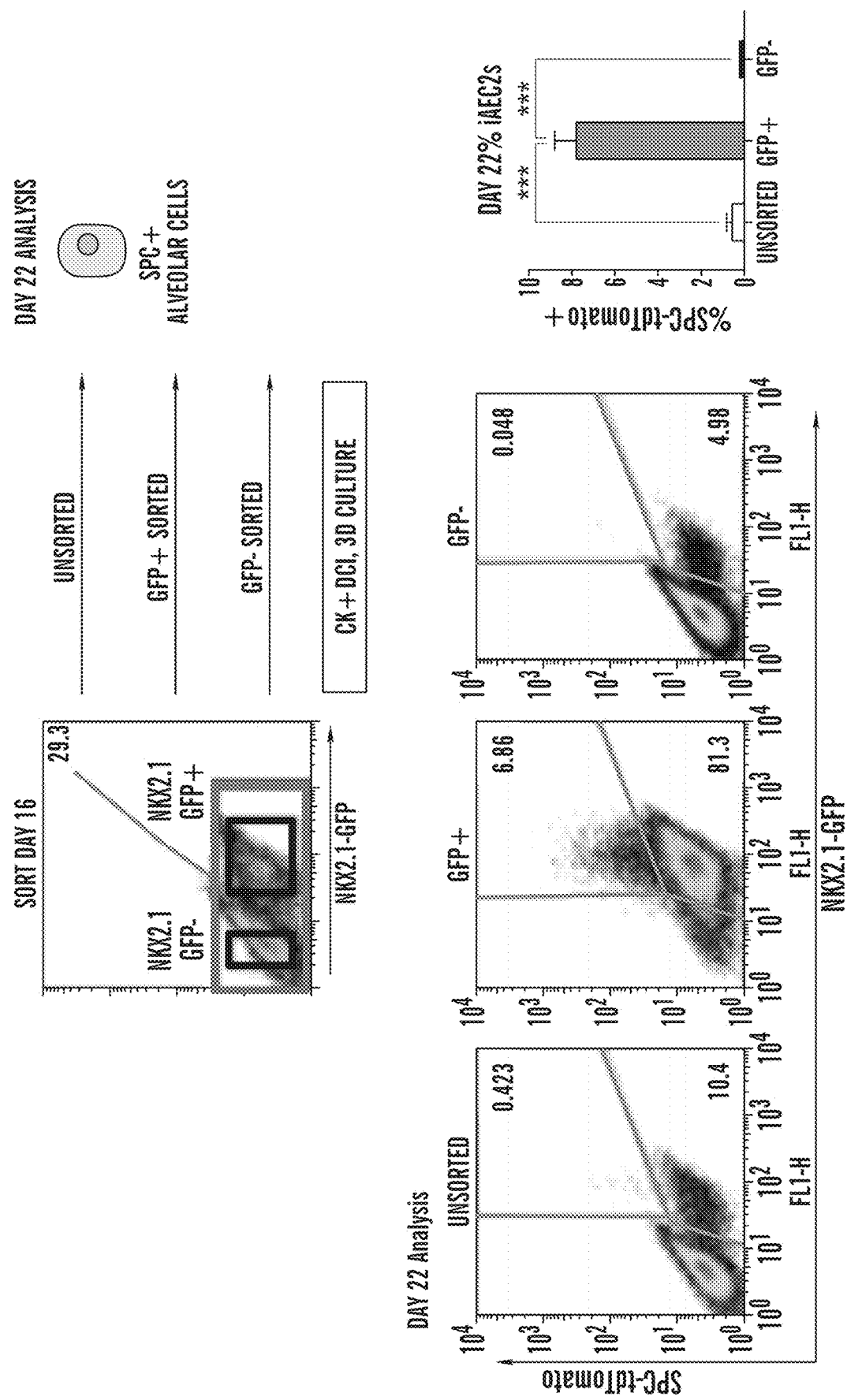
FIG. 16: After sorting early Day 15 NKX2.1+ or NKX2.1− cells and replating them in 3D culture, the entire SFTPC$^{tdTomato+}$ distal progenitor population derived from mesenchyme-depleted NKX2.1 GFP+ sorted cells, the first evidence of alveolar cells deriving from primordial NKX2.1+ progenitors in a human system.
Figure 17:
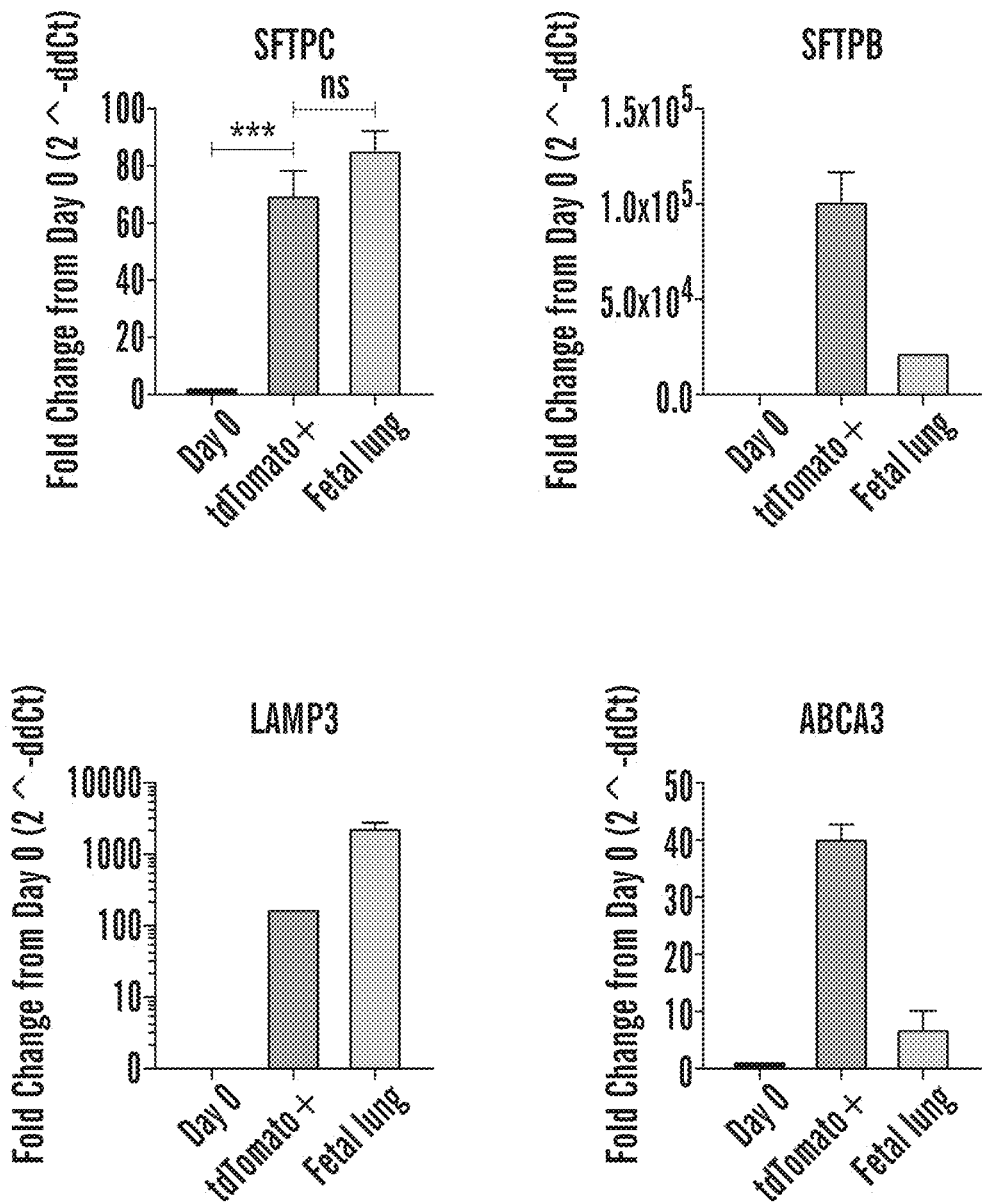
FIG. 17 depicts graphs of qRT-PCR on Day 36 SPCtd-Tomato+ compared to week 21 human fetal lung for distal lung epithelial genes showing fold change (2-ΔΔCt) normalized to day 0 undifferentiated iPSCs.

Human SFTPC+ cells derive from NKX2.1+ progenitor cells. tdTomato was targeted into the SFTPC locus of an iPSC line with an NKX2.1-GFP reporter, resulting in a dual reporter, with putative AEC2s expressing both NKX2.1-GFP and SFTPC-tdTomato, permitting the study of human developmental pathways in-vitro (FIG. 16).

iAEC2s express distal lung mRNA and protein. After NKX2.1+ progenitor cells were exposed to distalizing media for 20 days, SFTPCtdTomato+ cells were sorted to purity and analyzed by RT-qPCR, showing expression of AEC2-specific genes at levels similar to or higher than primary week 21 fetal SFTPC+ cells. They also express ABCA3, an important AEC2 lamellar body protein (FIG. 17).

Figure 18A:
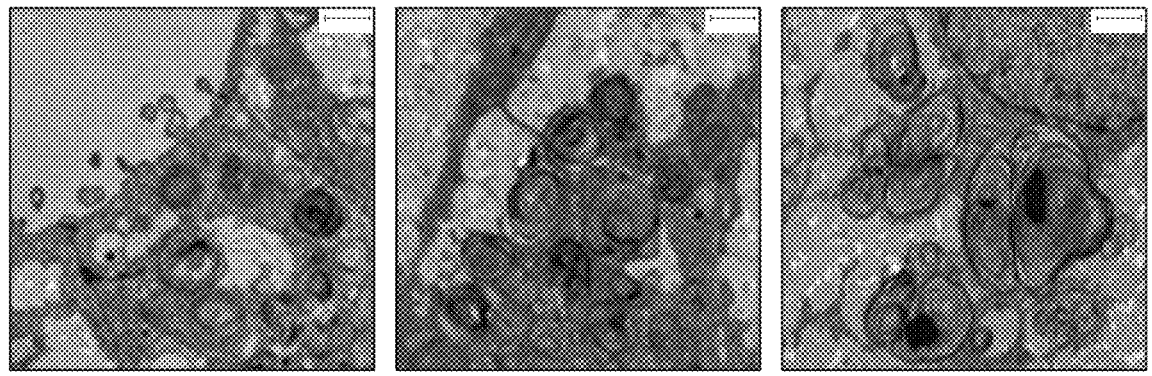
FIG. 18A depicts EM of Day 36 organoids demonstrating expression of mature lamellar bodies.
Figure 18B:
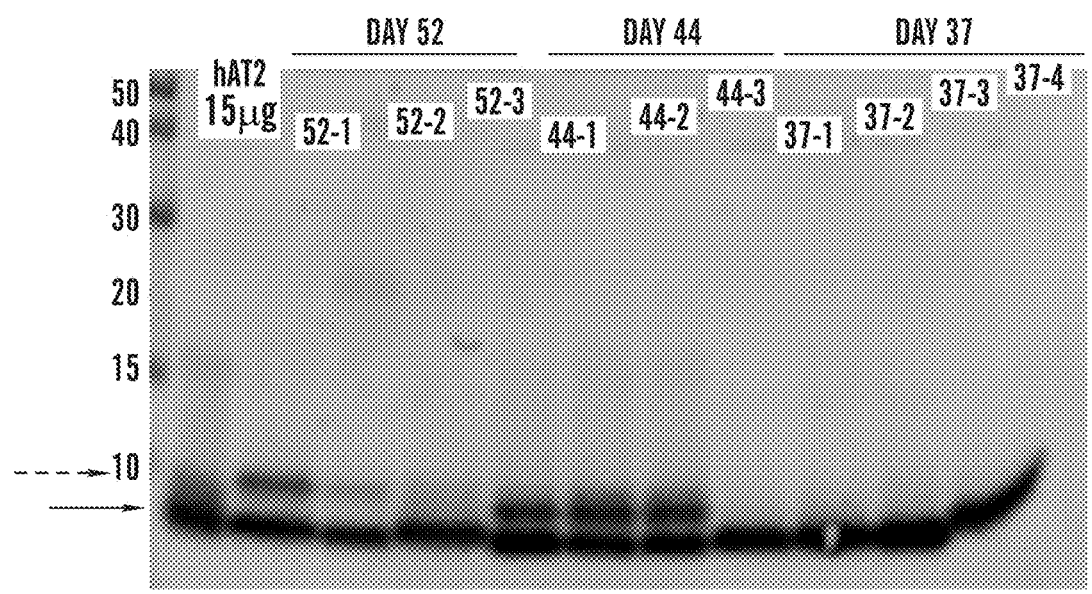
FIG. 18B depicts protein analysis demonstrating expression of mature 8kD SFTPB in organoids from Day 37, 44, and 52.
Figure 19:
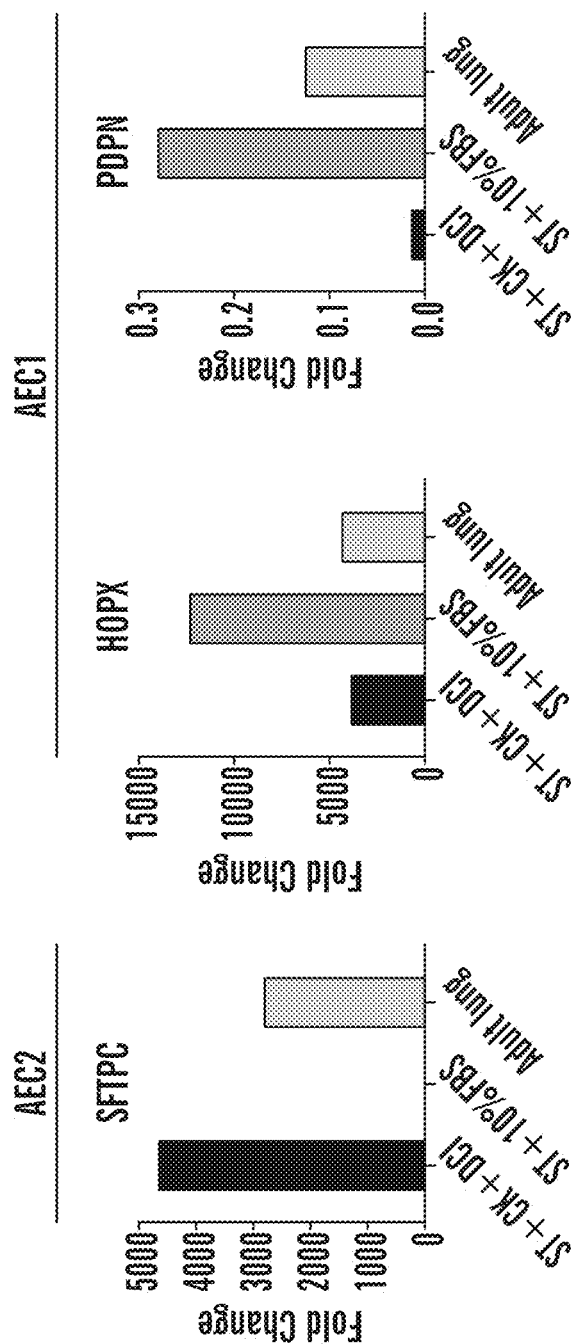
FIG. 19 demonstrates that when a pure population of Day 22 iAEC2s was cultured in CK+DCI media, SFTPC expression was maintained, whereas when they were cultured in 2D conditions, they upregulated AEC1 markers and lost SFTPC expression by RT-qPCR (fold change=(2-ΔΔCt) normalized to day 0)

Distal lung organoids are phenotypically similar to mature AEC2s. Since these SFTPCtdTomato+ cells could represent a range of alveolar developmental stages, it was next sought to assess the maturity level of these cells by evaluating whether they express lamellar bodies, a key AEC2 organelle (FIGS. 18A-18B). Expression of 8kD surfactant protein B (SFTPB) is also a marker of maturity in AEC2s. AEC2s can transdifferentiate into type I alveolar cells (AEC1s) in-vivo in response to injury as well as in-vitro after monolayer culture in DMEM+10% FBS (FIG. 19).

Discussion

Demonstrated herein is a working reporter iPSC line that facilitates identification and characterization of pure populations of iAEC2s. Human SFTPC+ distal lung cells derive from Day 15 SFTPC− NKX2.1+ cells. Distal iAEC2 organoids express both AEC2 mRNA and protein, as well as lamellar bodies and mature SFTPB protein. They can also upregulate AEC1 markers in response to monolayered culture, suggesting a relatively mature phenotype. iAEC2 organoids represent an in-vitro platform for alveolar disease modeling.

REFERENCES

Whitsett, J. A., et. al. Annu. Rev. Med. 61, 105-119 (2010).
Foster, C. D., et. al. Pediatr Res 61, 404-409 (2007).
Soares, J. J. et al. Pediatrics 132, 684-691 (2013).
Longmire, T. A. et al. Cell Stem Cell 10, 398-411 (2012).
Huang, S. X. L. et al. Nat. Biotechnol. 32, 84-91 (2013).

Example 4

It was found that after sorting SFTPC-tdTomato+ cells from the BU3 NGST iPSC line, replating them in 3D culture in CK+DCI, and passaging them multiple times (as described in FIG. 2E), that by Array Comparative Genomic Hybridization (aCGH) the cells are karyotypically normal. There was a 1.2 kb amplification not detectable by conventional karyotyping found in the passaged cells (FIG. 20), but this amplification was also found in the iPSC line in its pluripotent state (FIG. 21), indicating that there was no genetic drift in the passage-able alveolospheres despite weeks of culture and multiple rounds of cell sorting. The only other microdeletion found overlapped with a known copy number variant, indicating that it is a normal variant of the genome inherent to this iPSC line.

This is an important and novel finding because many cell lines that proliferate indefinitely in culture do so because of genetic abnormalities that give a small subclone a survival advantage. These data demonstrate that the alveolosphere differentiation protocol described herein does not result in karyotypic abnormalities and that proliferative alveolospheres are karyotypically normal after multiple passages, making them an even more valid surrogate for primary alveolar cells.

What is claimed herein is:

1. A method of making induced alveolar epithelial type 2 cells (iAEC2s) which produce surfactant and are capable of self-renewal in the absence of a mesenchymal cell, the method comprising:
   culturing in vitro a NKX2-1+ lung epithelial progenitor cell without mesenchymal co-culture, in the simultaneous presence of:
   an agonist of Wnt/beta-catenin signaling;
   a corticosteroid; and
   an agonist of cyclicAMP or the cyclicAMP pathway.

2. The method of claim 1, wherein the culturing step is continued for at least 3 days.

3. The method of claim 1, wherein the culturing step is continued for at least 15 days.

4. The method of claim 1, further comprising a second culturing step after the first culturing step, wherein the cells are cultured without being contacted with an agonist of Wnt/beta-catenin signaling.

5. The method of claim 4, wherein the second culturing step is continued for at least 5 days.

6. The method of claim 4, wherein the second culturing step is continued for at least 10 days.

7. The method of claim 4, wherein
   the first culturing step is continued for a period of about 2 weeks;

the second culturing step is continued for a period of about 1 week; and further comprising a third culturing step of culturing the cells resulting from the second culturing step in the presence of:
an agonist of Wnt/beta-catenin signaling;
a corticosteroid; and
an agonist of cyclicAMP or the cyclicAMP pathway for a period of about 1 week.

8. The method of claim 1, wherein the agonist of Wnt/beta catenin signaling is selected from the group consisting of:
CHIR99021; a recombinant Wnt polypeptide; a Wnt polypeptide; an exogenous Wnt polypeptide; BIO; WAY-316606; a (hetero) arylpyrimidine; IQ1; QS11; SB-216763; DCA; R-spondin; and an inhibitor of Axin2 and/or APC.

9. The method of claim 1, wherein the corticosteroid is selected from the group consisting of:
dexamethasone; hydrocortisone; cortisone; prednisone; prednisolone; methylprednisolone; triamncinolone; betamethasone; fludrocortisone acetate; and deoxycorticosterone acetate.

10. The method of claim 1, wherein the agonist of cyclicAMP or the cyclicAMP pathway is selected from the group consisting of:
cyclicAMP; IBMX; cholera toxin; forskolin; caffeine; theophylline; bucladesine; and pertussis toxin.

11. The method of claim 1, wherein the NKX2-1+ lung epithelial progenitor cell is further contacted or cultured with an agonist of FGF signaling.

12. The method of claim 11, wherein the agonist of FGF signaling is a polypeptide selected from the group consisting of:
KGF; a FGF receptor ligand; FGF1; FGF2; FGF3; FGF4; FGF6; FGF8; FGF9; FGF10; FGF17; FGF18; FGF22; and a small molecule agonist of FGF signaling.

13. The method of claim 11, wherein the agonist of FGF signaling is KGF polypeptide.

14. The method of claim 1, wherein the culturing further comprises culturing or contacting the cell with 3-isobutyl-1-methylxanthine (IMBX).

15. The method of claim 1, wherein the NKX2-1+ lung epithelial progenitor cell is a CD47hi/CD2610 cell.

16. The method of claim 1, wherein the iAEC2 cell is a NKX2-1+/SFTPC+ cell.

17. An isolated, in vitro induced alveolar epithelial type 2 cell (iAEC2) a) which is not in the presence of a mesenchymal cell, b) produces surfactant and, c) is capable of self-renewal in vitro in the absence of a mesenchymal cell.

18. The method of claim 1, wherein the iAEC2s are capable of being maintained in the absence of a mesenchymal cell for at least 1 month.

19. The method of claim 1, wherein the iAEC2s are capable of being maintained in the absence of a mesenchymal cell for at least 3 months.

20. The method of claim 1, wherein the iAEC2s are capable of being maintained in the absence of a mesenchymal cell for multiple passages.

21. The iAEC2 of claim 17, which is capable of being maintained in the absence of a mesenchymal cell for at least 1 month.

22. The iAEC2 of claim 17, which is capable of being maintained in the absence of a mesenchymal cell for at least 3 months.

23. The iAEC2 of claim 17, which is capable of being maintained in the absence of a mesenchymal cell for multiple passages.

24. The method of claim 1, wherein the producing of surfactant is surfactant secretion.

25. The method of claim 1, wherein the surfactant comprises protein and phospholipid.

* * * * *

UNITED STATES PATENT AND TRADEMARK OFFICE
CERTIFICATE OF CORRECTION

PATENT NO. : 10,975,357 B2  
APPLICATION NO. : 16/011809  
DATED : April 13, 2021  
INVENTOR(S) : Darrell N. Kotton and Anjali Jacob Page 1 of 1

It is certified that error appears in the above-identified patent and that said Letters Patent is hereby corrected as shown below:

In the Claims

At Column 88, Claim 15, Lines 6-7:
"The method of claim 1, wherein the NKX2-1+ lung epithelial progenitor cell is a CD47hi/CD2610 cell." should be replaced with -- The method of claim 1, wherein the NKX2-1+ lung epithelial progenitor cell is a CD47hi/CD26lo cell. --

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 19

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaactcttg tgcgtaagtc gatag                                           25

<210> SEQ ID NO 2
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
ggaggcggcc caaagggaga tccg                                            24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tagcacctgc agcaagatgg                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcaccggcgg gctctccatc                                                 20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgtgggcag caaagaggtc ct                                              22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggtgagtga gctgattcga g                                               21

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgacctcctc gcccttgctc accatg                                          26

<210> SEQ ID NO 8
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
ctacggacac atataagacc ctggtc                                              26

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgtgcatc ccacacct                                                       18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgaccgagt acaagcccac g                                                   21

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcaggcaccg ggcctgc                                                        17

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttgacgacta cttcgaaccc tgg                                                 23

<210> SEQ ID NO 13
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gaagctgctc atgccccagt gcaaccaagt gcttgacgac tacttccccc tggtcatcga         60
ctacttccag aaccagattg tgaggctg                                            88

<210> SEQ ID NO 14
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 14
actccttggc actcgtgaac                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggtgctgtg tgtttgtgtc                                                      20

<210> SEQ ID NO 16
<211> LENGTH: 58
<212> TYPE: DNA
<213> ORGANISM: Homo sapiens

<400> SEQUENCE: 16
cagtgcaacc aagtgcttga cgactacttc gaaccctggt catcgactac ttccagaa            58

<210> SEQ ID NO 17
<211> LENGTH: 56
<212> TYPE: DNA
<213> ORGANISM: Homo sapiens

<400> SEQUENCE: 17
cagtgcaacc aagtgcttga cgactacttc ccctggtca tcgactactt ccagaa               56

<210> SEQ ID NO 18
<211> LENGTH: 13
<212> TYPE: DNA
<213> ORGANISM: Homo sapiens

<400> SEQUENCE: 18
tacttcgaac cct                                                             13

<210> SEQ ID NO 19
<211> LENGTH: 11
<212> TYPE: DNA
<213> ORGANISM: Homo sapiens

<400> SEQUENCE: 19
tacttccccc t                                                               11
```